(12) United States Patent
Reynolds et al.

(10) Patent No.: US 7,384,950 B2
(45) Date of Patent: *Jun. 10, 2008

(54) THIENOPYRIMIDINEDIONES AND THEIR USE IN THE MODULATION OF AUTOIMMUNE DISEASE

(75) Inventors: Rachel Heulwen Reynolds, Loughborough (GB); Anthony Howard Ingall, Loughborough (GB); Rukhsana Tasneem Rasul, Loughborough (GB); Simon David Guile, Loughborough (GB); Martin Edward Cooper, Loughborough (GB)

(73) Assignee: AstraZeneca AB (SE)

( * ) Notice: Subject to any disclaimer, the term of this patent is extended or adjusted under 35 U.S.C. 154(b) by 174 days.

This patent is subject to a terminal disclaimer.

(21) Appl. No.: 10/483,162

(22) PCT Filed: Jul. 24, 2002

(86) PCT No.: PCT/GB02/03399

§ 371 (c)(1),
(2), (4) Date: Jul. 21, 2004

(87) PCT Pub. No.: WO03/011868

PCT Pub. Date: Feb. 13, 2003

(65) Prior Publication Data

US 2004/0254198 A1    Dec. 16, 2004

(30) Foreign Application Priority Data

Jul. 28, 2001   (GB)   ................ 0118479.5

(51) Int. Cl.
A61K 31/519   (2006.01)
C07D 495/04   (2006.01)
A61P 11/06    (2006.01)

(52) U.S. Cl. .................. 514/260.1; 544/278
(58) Field of Classification Search ................ 544/278; 514/260.1
See application file for complete search history.

(56) References Cited

U.S. PATENT DOCUMENTS

| | | | |
|---|---|---|---|
| 6,180,635 B1 | 1/2001 | Cheshire et al. |
| 6,232,320 B1 | 5/2001 | Stewart et al. |
| 6,300,334 B1 | 10/2001 | Bantick et al. |
| 6,342,502 B1 | 1/2002 | Cheshire et al. |
| 7,064,126 B2 | 6/2006 | Cooper et al. |
| 2004/0171623 A1 | 9/2004 | Reynolds et al. |
| 2006/0052400 A1 | 3/2006 | Guile |
| 2006/0135539 A1 | 6/2006 | Guile et al. |

FOREIGN PATENT DOCUMENTS

| WO | WO 98/54190 | 12/1998 |
|---|---|---|
| WO | WO 99/29695 | 6/1999 |
| WO | WO 00/12514 | 3/2000 |
| WO | WO 03/008422 | 1/2003 |
| WO | WO 2004/065393 | 8/2004 |
| WO | WO 2004/065394 | 8/2004 |
| WO | WO 2004/065395 | 8/2004 |

OTHER PUBLICATIONS

"New Drugs for Asthma, Allergy and COPD," Prog. Respir. Res. Basel, Karger, 2001, vol. 31, pp. 212-216.*
AllRefer.com Health entry for Chronic Obstructive Pulmonary Disease <<http://health.allrefer.com/health/chronic-obstructive-pulmonary-disease-prevention.html>> downloaded from the Internet Aug. 23, 2004.
BestHealth entry for ARDS (adult respiratory distress syndrome) <http://www.wfubmc.edu/besthealth/ency/article/000103prv.htm>.
Gupta et al., "Tacrolimus: a review of its use for the management of dermatoses", J. Eur. Acad. Dermatol. Venereal. 16:100-114 (2002).
MDAdvice.com entry for Asthma http://www.mdadvice.com/topics/asthma/info/1.htm downloaded from the internet Mar. 5, 2003.
Meagher et al., "Atopic dermatitis: Review of immunopathogenesis and advances in immunosuppressive therapy", Australas. J. Derm. 43:247-254 (2002).

(Continued)

Primary Examiner—Brenda L. Coleman
Assistant Examiner—Susanna Moore
(74) Attorney, Agent, or Firm—Fish & Richardson P.C.

(57) ABSTRACT

The invention relates to a compound of formula (1); wherein: $R^1$ and $R^2$ each independently represent a $C_{1-6}$alkyl, $C_{3-6}$ alkenyl, $C_{3-6}$ cycloalkyl $C_{1-3}$ alkyl or $C_{3-6}$ cycloalkyl; each of which may be optionally substituted by 1 to 3 halogen atoms; $R^3$ is isoxyzolidin-2-ylcarbonyl or tetrahydroisoxazin-2-ylcarbonyl wherein each ring is optionally substituted by one hydroxy group; Q is CO— or $C(R^4)(R^5)$-(wherein $R^4$ is a hydrogen atom or $C_{1-4}$alkyl and $R^5$ is a hydrogen atom or hydroxy group); Ar is a 5- to 10-membered aromatic ring system wherein up to 4 ring atoms may be heteroatoms independently selected from nitrogen, oxygen and sulphur, the ring system being optionally substituted by one or more substituents as defined in the specification. It also relates to methods of preparing, pharmaceutical compositions containing and methods of using the compound of the formula (1), particularly in the modulation of autoimmune disease

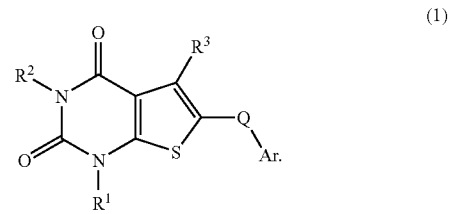

(1)

12 Claims, No Drawings

OTHER PUBLICATIONS

Perrett et al., "Cyclosporin in childhood psoriasis", *Journal of Dermatological Treatment* 14:113-118 (2003).

Tan et al., "Psoriasis", *Drugs of Today* 34(7):641-647 (1998).

Thestrup-Pedersen, "Tacrolimus treatment of atopic eczema/dermatitis syndrome", *Curr Opin Allergy Clin Immunol* 3:359-362 (2003).

Wolff et al., "Pimecrolimus for the treatment of inflammatory skin disease", *Expert Opin. Pharmacother.* 5:643-655 (2004).

Yamaguchi et al., "Novel Antiasthmatic Agents with Dual Activities of Thromboxane $A_2$ Synthetase Inhibition and Bronchodilation. V.[1])Thienopyridazinone Derivatives", *Chem. Pharm. Bull.* 43(2):236-240 (1995).

Yamamoto et al., "Topical tacrolimus: an effective therapy for facial psoriasis", *Eur J Dermatol* 13:471-473 (2003).

Yu et al., "Refractory atopic dermatitis treated with low dose cyclosporin", *Annals of Allergy, Asthma & Immunology* 89:127-131.

BestHealth entry for ARDS (adult respiratory distress syndrome) <http://www.wfubmc.edu/besthealth/ency/article/000103prv.htm> downloaded Mar. 5, 2003.

\* cited by examiner

THIENOPYRIMIDINEDIONES AND THEIR USE IN THE MODULATION OF AUTOIMMUNE DISEASE

CROSS-REFERENCE TO RELATED APPLICATIONS

This application is the national phase application under U.S.C. § 371 of PCT International Application No. PCT/GB02/03399, which has an International filing date of Jul. 24, 2002, and which designated United Kingdom Application Serial No. 0118479.5, filed Jul. 28, 2001, as priority. The contents of these applications are incorporated by reference in their entirety.

The present invention relates to thieno[2,3-d]pyrimidinediones, processes for their preparation, pharmaceutical compositions containing them and their use in therapy. In particular, in their use in the modulation of autoimmune disease.

T-cells play an important role in the immune response, however in auto-immune disease T-cells are inappropriately activated against particular tissues and proliferate, eg causing the inflammation associated with rheumatoid arthritis. Inhibition of the proliferation of T-cells is beneficial in the modulation of autoimmune disease. The present invention relates to compounds which are beneficial in the modulation of autoimmune disease.

The compounds of WO 2000/12514 and WO2001/038489 are known to be useful in modulating the immune response. These applications encompass compounds having an amidic —C—N— at the 5-position of the thienopyrimidine ring system. These compounds exist as slowly-interconverting rotamers, because of the combination of slow rotations around the amidic C—N link and around the bond from the amidic carbonyl to the thienopyrimidine core; the rate of interconversion is such that the isomers may be separated by HPLC. Such hindered rotation presents significant problems for the development of a pharmaceutical compound: long equilibration times imply that different initial rotameric mixtures may be expected to arise if the conditions of the final step of the synthesis is varied, leading to problems in assaying purity and reproducing the solid form of the raw drug. Moreover rotameric forms having lifetimes comparable to biological half lives may be expected to be handled by metabolic processes in different ways, potentially giving rise to structurally dissimilar metabolites, the biological activity and safety of all of which must be fully studied and documented. We have now found a class of compounds which have incorporate an amidic —C—N— group at the 5-position of the thienopyrimidine ring system, have interesting potency and yet do not have the problems associated with the compounds existing as separate rotamers under ambient conditions.

In accordance with the present invention, there is provided a compound of formula (1)

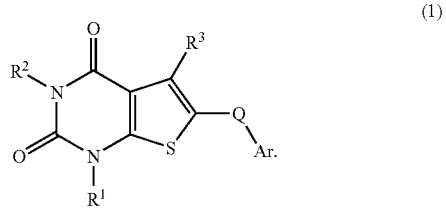

(1)

wherein:
$R^1$ and $R^2$ each independently represent a $C_{1-6}$alkyl, $C_{3-6}$alkenyl, $C_{3-6}$cycloalkyl$C_{1-3}$alkyl or $C_{3-6}$cycloalkyl; each of which may be optionally substituted by 1 to 3 halogen atoms;

$R^3$ is isoxazolidin-2-ylcarbonyl or tetrahydroisoxazin-2-ylcarbonyl wherein each ring is optionally substituted by one hydroxy group;

Q is —CO— or —C($R^4$)($R^5$)— (wherein $R^4$ is a hydrogen atom or $C_{1-4}$alkyl and $R^5$ is a hydrogen atom or hydroxy group);

Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —(CH$_2$)$_p$N($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from nitrogen, oxygen and sulphur;

p is 1 to 4

$R^6$ and $R^7$ each independently represent a hydrogen atom, $C_{1-4}$alkanoyl or $C_{1-4}$alkyl, or together with the nitrogen atom to which they are attached form a 5- to 7-membered saturated heterocyclic ring;

$R^8$ and $R^9$ each independently represent a hydrogen atom, $C_{1-4}$alkanoyl or $C_{1-4}$alkyl, or together with the nitrogen atom to which they are attached form a 5- to 7-membered saturated heterocyclic ring;

or a pharmaceutically acceptable salt or prodrug thereof.

In another aspect the invention relates to a compound of the formula (1) as hereinabove defined or to a pharmaceutically acceptable salt thereof.

Within the present invention it is to be understood that a compound of the formula (1) or a salt thereof may exhibit the phenomenon of tautomerism and that the formulae drawings within this specification can represent only one of the possible tautomeric forms. It is to be understood that the invention encompasses any tautomeric form and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

The present invention relates to the compounds of formula (1) as hereinbefore defined as well as to the salts thereof. Salts for use in pharmaceutical compositions will be pharmaceutically acceptable salts, but other salts may be useful in the production of the compounds of formula (1) and their pharmaceutically acceptable salts. Pharmaceutically acceptable salts of the invention may, for example, include acid addition salts of the compounds of formula (1) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula (1) are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

Preferred salts include an acid addition salt such as a hydrochloride, hydrobromide, phosphate, acetate, fumarate, maleate, tartrate, citrate, oxalate, methanesulfonate or p-toluenesulfonate, or an alkali metal salt such as a sodium or potassium salt.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, *Advanced Drug Delivery Reviews*, 8, 1-38 (1992);
d) H. Bundgaard, et al., *Journal of Pharmaceutical Sciences*, 77, 285 (1988); and
e) N. Kakeya, et al., *Chem. Pharm. Bull.*, 32, 692 (1984).

Examples of such pro-drugs may be used to form in-vivo-cleavable esters of a compound of the formula 1. An in vivo hydrolysable ester of a compound of the formula (I) containing a hydroxy group is, for example, a pharmaceutically acceptable ester, which is hydrolysed in the human or animal body to produce the parent alcohol. The term includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

It is also to be understood that certain compounds of the formula (1) can exist in solvated forms as well as unsolvated forms, for example, hydrated forms. It is to be understood that the invention encompasses all such solvated forms, which are useful in therapy, in particular for the particular therapeutic purposes mentioned hereinafter.

In the present specification, unless otherwise indicated, an alkyl, alkenyl or alkynyl group or an alkyl, alkenyl or alkynyl moiety in a substituent group may be linear or branched.

Ar may be bonded to the —$C(R^4)(R^5)$— group by a ring carbon or a ring nitrogen providing this does not lead to quaternisation.

It will be appreciated that in a group —$C(R^4)(R^5)$Ar, $R^5$ may represent a hydroxy group only when Ar is bonded to —$C(R^4)(R^5)$ through a carbon atom and not a heteroatom. Furthermore, it should be understood that in —C(O)Ar, Ar is bonded through a carbon atom and not a heteroatom to the moiety —C(O). A hydroxyalkyl may contain more than one hydroxy group but a single hydroxy group is preferred.

For the avoidance of doubt, when Ar is substituted by an oxo or thioxo group, it is intended that Ar includes the dihydro-versions of aromatic ring systems. For example, it encompasses thiazolyl and 2,3-dihydrothiazolyl(when the latter is substituted by an oxo or thioxo group). Similarly Ar encompasses, for example, 2,3-dihydrobenzoxazolyl, 2,3-dihydrobenzothiazolyl, 2,3-dihydropyrazinyl and 2,3-dihydrobenzimidazolyl (when these are substituted by an oxo or thioxo group).

Ar is a 5- to 10-membered aromatic ring system wherein up to 4 ring atoms may be heteroatoms independently selected from nitrogen, oxygen and sulphur, the ring system being optionally substituted by one, two, three or four substituents independently selected from $C_{1-4}$alkyl (optionally substituted by 1, 2 or 3 hydroxy groups) (e.g. methyl, ethyl, n-propyl, n-butyl, hydroxymethyl, 2-hydroxyethyl, 1-hydroxyethyl or 3-hydroxypropyl), $C_{1-4}$alkoxy (e.g. methoxy, ethoxy, n-propoxy or n-butoxy), halogen (e.g. fluorine, chlorine, bromine or iodine), haloalkyl, (e.g. fluoromethyl, chloromethyl, bromomethyl, 2-fluoroethyl, 2-fluoropropyl or 3-fluoropropyl), dihaloalkyl, (e.g. difluoromethyl, dichloromethyl, chlorofluoromethyl, dibromomethyl, 2,2-difluoroethyl, 2,2-difluoropropyl or 2,3-difluoropropyl), trihaloalkyl, (e.g. trifluoromethyl, trichloromethyl, 2,2,2-trifluoroethyl, 2,2,2-trifluoropropyl or 2,2,3-trifluoropropyl), $C_{1-4}$alkoxy$C_{1-4}$alkyl, (e.g. methoxymethyl, ethoxymethyl, 2-methoxyethyl, 2-methoxypropyl or 3-methoxypropyl), $C_{1-4}$alkylthio (e.g. methylthio, ethylthio, n-propylthio or n-butylthio), $C_{1-4}$alkoxycarbonyl (e.g. methoxycarbonyl, ethoxycarbonyl, n-propoxycarbonyl, isopropoxycarbonyl or n-butoxycarbonyl), $C_{2-4}$alkanoyl (e.g. acetyl or propionyl), oxo, thioxo, nitro, cyano, —$N(R^6)R^7$ (e.g. amino, N-methylamino, N-ethylamino, di-N,N-methylamino or N-ethyl-N-methylamino), —$(CH_2)_pN(R^8)R^9$ [e.g. —$CH_2N(R^8)R^9$, —$CH_2CH_2N(R^8)R^9$ or $CH_2CH_2CH_2N(R^8)R^9$], hydroxy, $C_{1-4}$alkylsulphonyl (e.g. methylsulphonyl, ethylsulphonyl or propylsulphonyl), $C_{1-4}$alkylsulphinyl (methylsulphinyl, ethylsulphinyl or propylsulphinyl), carbamoyl, $C_{1-4}$alkylcarbamoyl (e.g. methylcarbamoyl, ethylcarbamoyl and propylcarbamoyl) di-$C_{1-4}$alkylcarbamoyl (e.g. di-N,N-methylcarbamoyl, N-ethyl-N-methylcarbamoyl or di-N,N-ethylcarbamoyl), carboxy and or a 5 or 6 membered aromatic ring containing up to 4 heteroatoms independently selected from nitrogen, oxygen and sulphur (e.g. phenyl, pyrimidyl, thienyl and furanyl).

The aromatic ring system may be monocyclic or polycyclic (e.g. bicyclic), examples of which include phenyl, naphthyl, quinolyl, pyrazolyl, thienyl, oxazolyl, imidazolyl, pyridinyl, pyrrolo[2,3-b]pyridyl, benzimidazolyl, indazolyl, benzothiazolyl, 2,3-dihydrobenzothiazolyl, benzoxazolyl, thiazolyl, 2,3-dihydrothiazolyl, 2,3-dihydrobenzimidazolyl, 2,3-dihydrobenzoxazolyl, thiazolo[5,4-b]pyridyl and benzotriazolyl.

Further values of $R^1$, $R^2$, $R^3$, $R^4$, $R^5$, $R^6$, $R^7$, $R^8$, $R^9$, p, Q and Ar and substituents on Ar are further defined hereinafter. Such values may be used where appropriate with any of the definitions, claims or embodiments defined hereinafter or hereinbefore.

In one aspect Ar is a 5 or 6 membered monocyclic ring.
In another aspect Ar is a 8, 9 or 10 bicyclic ring.
In yet another aspect Ar is a 9 or 10 bicyclic ring.
In one aspect the invention relates to compounds of the formula 1 wherein Ar is a 5- to 10-membered aromatic ring system containing up to 4 ring heteroatoms selected from nitrogen, oxygen and sulphur providing that there is at least 1 ring nitrogen, the ring being optionally substituted as defined above. These compound have been found to be advantageous.

In another aspect Ar is a 5- to 10-membered aromatic ring system containing 1 or 2 ring nitrogen atoms and optionally one ring sulphur or oxygen atom or containing 3 ring nitrogen atoms, the ring being optionally substituted as defined above.

In another aspect Ar is a 5- to 10-membered aromatic ring system containing 1 or 2 ring nitrogen atoms and optionally one ring sulphur atom, the ring being optionally substituted as defined above.

In another aspect Ar is a 5- to 10-membered aromatic ring system containing 2 ring nitrogen, the ring being optionally substituted as defined above.

In yet another aspect Ar is selected from imidazolyl, pyrazolyl, pyrrolyl, isoxazolyl, phenyl, quinolyl, indolyl, benzimidazolyl, indazolyl, benztriazolyl, 2,3-dihydrothiazolyl, 2,3-dihydrobenzoxazolyl, pyrrolo [2,3-b]pyridyl, imidazo[1,2-a]pyridyl, imidazo[4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl.

In yet another aspect Ar is selected from imidazolyl, pyrazolyl, pyrrolyl, isoxazolyl, quinolyl, indolyl, benzimidazolyl, indazolyl, benztriazolyl, 2,3-dihydrothiazolyl, 2,3-dihydrobenzoxazolyl, pyrrolo [2,3-b]pyridyl, imidazo[1,2-a]pyridyl, imidazo[4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl.

In yet another aspect Ar is selected from imidazolyl, pyrazolyl, benzimidazolyl, indazolyl, benztriazolyl, 2,3-dihydrobenzoxazolyl, pyrrolo [2,3-b]pyridyl, imidazo[1,2-a]pyridyl, imidazo[4,5-b]pyridyl, 2,3-dihydrothiazolo[5,4-b]pyridyl, 2,3-dihydropyrazinyl and 2,3-dihydrobenzimidazolyl.

More particularly Ar is selected from imidazolyl, quinolyl, indolyl, benzimidazolyl, indazolyl, pyrazolyl, benztriazolyl, 2,3-dihydrothiazolyl, 2,3-dihydrobenzoxazolyl, pyrrolo [2,3-b]pyridyl, thiazolo[5,4-b]pyridyl, 2,3-dihydrobenzothiazolyl and 2,3-dihydrobenzimidazolyl.

In yet another aspect Ar is selected from imidazolyl, pyrazolyl, pyrrolyl, isoxazolyl, henyl and 2,3-dihydropyrazinyl.

In yet another aspect Ar is selected from quinolyl, indolyl, benzimidazolyl, indazolyl, benztriazolyl, 2,3-dihydrothiazolyl, 2,3-dihydrobenzoxazolyl, pyrrolo [2,3-b]pyridyl, imidazo[1,2-a]pyridyl, imidazo[4,5-b]pyridyl, 2,3-dihydrothiazolo[5,4-b]pyridyl, 2,3-dihydrobenzothiazolyl and 2,3-dihydrobenzimidazolyl.

In another aspect, when the substituent on Ar is a 5 or 6 membered aromatic ring, this substituent on Ar contains up to 2 heteroatoms independently selected from nitrogen, oxygen and sulphur. In one aspect it is selected from furanyl, thienyl, phenyl and pyrimidinyl. In another aspect, it is selected from pyrimidyl and phenyl. In yet another aspect, it is phenyl.

Examples of the type of ring formed by $R^6$ and $R^7$ together with the nitrogen atom to which they attached include pyrrolidino, piperidino, morpholino, pierazino, azepano, 1,4-oxepano and 1,4 diazepano. In another aspect, the ring is selected from pyrrolidino, piperidino or morpholino.

Examples of the type of ring formed by $R^8$ and $R^9$ together with the nitrogen atom to which they attached include pyrrolidino, piperidino, morpholino, pierazino, azepano, 1,4-oxepano and 1,4 diazepano. In another aspect, the ring is selected from pyrrolidino, piperidino or morpholino.

$R^1$ and $R^2$ each independently represent $C_{1-6}$alkyl, such as $C_{1-5}$alkyl (e.g. methyl, ethyl, n-propyl, 1-methylethyl, n-butyl, 2-methylpropyl, 2,2-dimethylpropyl, n-pentyl or n-hexyl), $C_{3-6}$alkenyl, such as $C_{3-4}$alkenyl (e.g. 1-propenyl, 1-butenyl, 1-pentenyl or 1-hexenyl), $C_{3-6}$cycloalkyl$C_{1-3}$alkyl (cyclopropylmethyl, cyclobutylmethyl, cyclopentylmethyl, 2-(cyclopropyl)ethyl, 2-(cyclobutyl)ethyl or 2-(cyclopentyl)ethyl) or $C_{3-6}$cycloalkyl, such as $C_{5-6}$cycloalkyl (cyclopropyl, cyclobutyl, cyclopentyl or cyclohexyl) each of which may be optionally substituted by 1 to 3 halogen atoms (e.g. trifluoromethyl 2,2,2-trifluoroethyl, 2-chloroethyl, 2-chloropropyl or 3,3,3-trifluoropropyl).

In another aspect $R^1$ and $R^2$ each independently represent $C_{1-5}$alkyl or $C_{3-6}$cycloalkylmethyl, each optionally substituted by 1 to 3 halogen atoms.

In yet another aspect, $R^1$ is ethyl, n-propyl, 1-methylethyl, 2-methylpropyl, 2,2-dimethylpropyl, cyclopropylmethyl, trifluoromethyl 2,2,2-trifluoroethyl, 2-chloroethyl, 2-chloropropyl or 3,3,3-trifluoropropyl.

In yet another aspect, $R^1$ is ethyl, n-propyl, isopropyl or 2-methylpropyl.

In yet another aspect, $R^1$ is 2-methylpropyl.

In one aspect $R^2$ is methyl or trifluoromethyl.

In yet another aspect, $R^2$ is methyl.

In yet another aspect, $R^3$ is hydroxyisoxazolidin-2-ylcarbonyl, tetrahydroisoxazin-2-yl or hydroxytetrahydroisoxazin-2-ylcarbonyl.

In yet another aspect, $R^3$ is hydroxyisoxazolidin-2-ylcarbonyl or hydroxytetrahydroisoxazin-2-ylcarbonyl.

In yet another aspect, $R^3$ is hydroxyisoxazolidin-2-yl carbonyl.

In yet another aspect, $R^3$ is 4-hydroxyisoxazolidin-2-yl.

In yet another aspect, $R^3$ is 4S-hydroxyisoxazolidin-2-yl.

In another aspect, $R^4$ and $R^5$ are independently hydrogen or methyl.

In another aspect, Q is —CO— or —CH$_2$—.

In one aspect Q is —CO—.

In another aspect Q is —CH$_2$—.

In another aspect, Ar is unsubstituted or substituted by 1, 2 or 3 substituents.

In yet another aspect, Ar is unsubstituted or substituted by 1 or 2 substituents.

In yet another aspect, substituents for Ar include $C_{1-4}$alkyl (optionally substituted by 1 or 2 hydroxy groups), $C_{1-4}$alkoxy, halogen, trihaloalkyl, $C_{1-4}$alkylthio, $C_{2-4}$alkanoyl, oxo, thioxo, cyano and —(CH$_2$)pN($R^8$)$R^9$ (wherein p is 1 or 2), hydroxy, $C_{1-4}$alkylsulphonyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from nitrogen, oxygen and sulphur.

In a particular aspect, substituents for Ar are selected from $C_{1-4}$alkyl, halogen, $C_{2-4}$alkanoyl, trifluoromethyl, oxo, thioxo, hydroxy$C_{1-4}$alkyl, amino, $C_{1-4}$alkylamino and $C_{1-4}$alkylthio.

In yet another aspect, substituents for Ar include methyl, ethyl, n-propyl, iso-propyl, tert-butyl, 1-methylethyl, trifluoromethyl, chloro, fluoro, bromo, hydroxymethyl, acetyl, methylthio, amino, methylamino, furanyl, thienyl, pyrimidyl, phenyl, cyano, thioxo and oxo.

In yet another aspect, substituents for Ar include methyl, propyl, isopropyl, tert-butyl, 1-methylethyl, trifluoromethyl, chloro, fluoro, bromo, methylthio, amino, methylamino, phenyl, pyrimidyl, cyano, thioxo and oxo.

Yet further particular substituents for Ar are selected from methyl, ethyl, propyl, tert-butyl, 1-methylethyl, chloro, fluoro, bromo, hydroxymethyl, acetyl, methylthio, amino, methylamino, thioxo and oxo.

Yet further particular substituents for Ar are selected from methyl, ethyl, propyl, tert-butyl, fluoro, chloro, oxo, thioxo, hydroxymethyl, amino, methylamino and methylthio.

Yet further particular substituents for Ar are selected from methyl, propyl, tert-butyl, 1-methylethyl, chloro, fluoro, methylthio, amino, methylamino, thioxo and oxo.

Particular values for Ar include 4,5-dichloro-2-methylimidazol-1-yl, 4,5-dichloro-2-hydroxymethylimidazol-1-yl, 2,4,5-trichloro-2-methylimidazol-1-yl, 4,5-dichloroimidazol-2-yl, 2-bromo-4,5-dichloroimidazol-2-yl, 2-methylthio-imidazoly-1-yl, 3,5-dimethylpyrazol-4-yl, 1,3,5-trimethylpyrazoly-4-yl, 3,5-dimethylpyrazol-4-yl, 3-tert-butyl-5-methylpyrazol-4-yl, 3,5-dimethylpyrazol-1-yl, 5-methyl-3-phenylpyrazol-4-yl, 5-methyl-3-(trifluoromethyl)pyrazol-4-yl, 5-methyl-3-(prop-2-yl)pyrazol-4-yl, 3,5-methyl-1-phenylpyrazol-4-yl, 5-dichloro-2,3-dihydro-2-oxothiazol-3-yl, 4-chloro-2,3-dihydro-2-oxothiazol-3-yl, 3,5-dimethylisoxazol-4-yl, 2,4-dimethyl-1-(prop-2-yl)pyrrol-3-yl, 2-trifluorophenyl, 2,3-dihydro-6-methyl-3-oxopyrazinyl, quinol-4-yl, quinol-5-yl, 6-fluoroquinol-4-yl, 8-fluoroquinol-4-yl, 2-methylquinol-4-yl, 2-methylindol-3-yl, 7-methylindol-3-yl, 5-cyanoindol-1-yl, 2-methylbenzimidazol-1-yl, 2-ethylbenzimidazol-1-yl, 2-propylbenzimidazol-1-yl, 2-methylthiobenzimidazol-1-yl, 2-hydroxymethylbenzimidazol-1-yl, 2-methylaminobenzimidazol-1-yl, 2-aminobenzimidazol-1-yl, pyrrolo[2,3-b]pyridin-3-yl, 2-methylpyrrolo[2,3-b]pyridin-1-yl, 2-methylpyrrolo[2,3-b]pyridin-3-yl, imidazo[1,2-a]pyrid-3-yl, 2-(methylthio)imidazo[4,5-b]pyrid-1-yl, 2-(methylthio)imidazo[4,5-b]pyrid-3-yl, 1H-1,2,3-benzotriazol-1-yl, 2-oxo-2,3-dihydrobenzothiazol-3-yl, 2-thioxo-2,3-dihydrobenzothiazol-3-yl, 2-oxo-2,3-dihydrobenzoxazol-1-yl, 2-oxo-2,3-dihydrobenzimidazol-3-yl, 2-oxo-2,3-dihydrobenzimidazol-1-yl, 5,6-difluoro-2-oxo-2,3-dihydrobenzimidazol-1-yl and 2-oxo-1,3-thiazolo[5,4-b]pyridin-3-yl.

Further particular values for Ar include 4,5-dichloro-2-methylimidazol-1-yl, 2,4,5-trichloro-2-methylimidazol-1-yl, 4,5-dichloroimidazol-2-yl, 3,5-dimethylpyrazol-4-yl, 1,3,5-trimethylpyrazol-4-yl, 3,5-dimethylpyrazol-4-yl, 3-tert-butyl-5-methylpyrazol-4-yl, 5-dichloro-2,3-dihydro-2-oxothiazol-3-yl, 4-chloro-2,3-dihydro-2-oxothiazol-3-yl, quinol-4-yl, quinol-5-yl, 6-fluoroquinol-4-yl, 8-fluoroquinol-4-yl, 2-methylquinol-4-yl, 2-methylindol-3-yl, 7-methylindol-3-yl, 5-cyanoindol-1-yl, 2-methylbenzimidazol-1-yl, 2-ethylbenzimidazol-1-yl, 2-propylbenzimidazol-1-yl, 2-methylthiobenzimidazol-1-yl, 2-hydroxymethylbenzimidazol-1-yl, 2-methylaminobenzimidazol-1-yl, 2-aminobenzimidazol-1-yl, pyrrolo[2,3-b]pyridin-3-yl, 2-methylpyrrolo[2,3-b]pyridin-1-yl, 2-methylpyrrolo[2,3-b]pyridin-3-yl, 1H-1,2,3-benzotriazol-1-yl, 2-oxo-2,3-dihydrobenzothiazol-3-yl, 2-thioxo-2,3-dihydrobenzothiazol-3-yl, 2-oxo-2,3-dihydrobenzoxazol-1-yl, 6-methyl-3-oxo-2,3-dihydropyrazin-2-yl and 2-oxo-1,3-thiazolo[5,4-b]pyridin-3-yl.

In one aspect, $R^6$ and $R^7$ each independently represent a hydrogen atom, $C_{1-4}$alkanoyl (e.g. formyl, acetyl or propionyl) or $C_{1-4}$ alkyl (e.g. methyl, ethyl, n-propyl or n-butyl), or together with the nitrogen atom to which they are attached form a 5- to 7-membered saturated heterocyclic ring.

In yet another aspect, $R^6$ and $R^7$ each independently represent a hydrogen atom or $C_{1-4}$alkyl.

In one aspect, $R^8$ and $R^9$ each independently represent a hydrogen atom, $C_{1-4}$alkanoyl (e.g. formyl, acetyl or propionyl) or $C_{1-4}$ alkyl (e.g. methyl, ethyl, n-propyl or n-butyl), or together with the nitrogen atom to which they are attached form a 5- to 7-membered saturated heterocyclic ring.

In yet another aspect, $R^8$ and $R^9$ each independently represent a hydrogen atom or $C_{1-4}$alkyl.

A particular class of compound is of the formula (1) wherein:
  $R^1$ is $C_{1-5}$alkyl or $C_{3-6}$cycloalkylmethyl;
  $R^2$ is $C_{1-5}$alkyl;
  $R^3$ is isoxazolidin-2-ylcarbonyl or tetrahydroisoxazin-2-ylcarbonyl wherein each ring is optionally substituted by one hydroxy group;
  Q is —CO— or —CH$_2$— (wherein $R^4$ is a hydrogen atom or $C_{1-4}$alkyl and $R^5$ is a hydrogen atom or a hydroxy group);
  Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, NR$^6$R$^7$ and —CH$_2$NR$^8$R$^9$;
  $R^6$ and $R^7$ each independently represent a hydrogen atom or $C_{1-4}$alkyl, or together with the nitrogen atom to which they are attached form a 5- to 7-membered saturated heterocyclic ring;
  $R^8$ and $R^9$ each independently represent a hydrogen atom or $C_{1-4}$ alkyl, or together with the nitrogen atom to which they are attached form a 5- to 7-membered saturated heterocyclic ring;
  or a pharmaceutically acceptable salt thereof.

Another class of compound is of the formula (1) wherein:
  $R^1$ is $C_{1-5}$alkyl or $C_{3-6}$cycloalkylmethyl;
  $R^2$ is $C_{1-5}$alkyl;
  $R^3$ is hydroxyisoxazin-2-ylcarbonyl, tetrahydroisoxazin-2-ylcarbonyl or hydroxytetrahydroisoxazin-2-ylcarbonyl;
  Q is —CO— or —CH$_2$—;
  Ar is a 5- to 10-membered aromatic ring system containing up to 4 ring heteroatoms selected from nitrogen, oxygen and sulphur providing that there is at least 1 ring nitrogen, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N(R$^6$)R$^7$ and —(CH$_2$)pN(R$^8$)R$^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy and a 5 or 6 membered aromatic ring containing up to 4 heteroatoms independently selected from nitrogen, oxygen and sulphur;
  $R^6$ and $R^7$ each independently represent a hydrogen atom or $C_{1-4}$alkyl, or together with the nitrogen atom to which they are attached form a 5- to 7-membered saturated heterocyclic ring;
  $R^8$ and $R^9$ each independently represent a hydrogen atom or $C_{1-4}$ alkyl, or together with the nitrogen atom to which they are attached form a 5- to 7-membered saturated heterocyclic ring;
  or a pharmaceutically acceptable salt thereof.

Another class of compound is of the formula (1) wherein:
- $R^1$ is ethyl, n-propyl, 1-methylethyl, 2-methylpropyl, 2,2-dimethylpropyl, cyclopropylmethyl, trifluoromethyl 2,2,2-trifluoroethyl, 2-chloroethyl, 2-chloropropyl or 3,3,3-trifluoropropyl.
- $R^2$ is methyl;
- $R^3$ is hydroxytetrahydroisoxazin-2-ylcarbonyl, tetrahydroisoxazin-2-ylcarbonyl or hydroxytetrahydroisoxazin-2-ylcarbonyl;
- Q is —CO— or —$CH_2$—;
- Ar is a 5- to 10-membered aromatic ring system containing up to 4 ring heteroatoms selected from nitrogen, oxygen and sulphur providing that there is at least 1 ring nitrogen, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —($CH_2$)pN($R^1$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, and a 5 or 6 membered aromatic ring containing up to 4 heteroatoms independently selected from nitrogen, oxygen and sulphur;
- $R^6$ and $R^7$ each independently represent a hydrogen atom or $C_{1-4}$alkyl, or together with the nitrogen atom to which they are attached form a 5- to 7-membered saturated heterocyclic ring;
- $R^8$ and $R^9$ each independently represent a hydrogen atom or $C_{1-4}$ alkyl, or together with the nitrogen atom to which they are attached form a 5- to 7-membered saturated heterocyclic ring;
- or a pharmaceutically acceptable salt thereof.

Another class of compound is of the formula (1) wherein:
- $R^1$ is ethyl, n-propyl, 1-methylethyl, 2-methylpropyl, 2,2-dimethylpropyl or cyclopropylmethyl;
- $R^2$ is methyl;
- $R^3$ is hydroxyisoxazolidin-2-ylcarbonyl, tetrahydroisoxazin-2-ylcarbonyl or hydroxytetrahydroisoxazin-2-ylcarbonyl;
- Q is —$CH_2$—;
- Ar is a 5- to 10-membered aromatic ring system containing up to 4 ring heteroatoms selected from nitrogen, oxygen and sulphur providing that there is at least 1 ring nitrogen, the ring system being optionally substituted by 1 or 2 substituents independently selected from $C_{1-4}$alkyl (optionally substituted by 1, 2 or 3 hydroxy groups), $C_{1-4}$alkoxy, halogen, trihaloalkyl, $C_{1-4}$alkylthio, $C_{2-4}$alkanoyl, oxo, thioxo, cyano and —($CH^2$)pN($R^8$)$R^9$ (wherein p is 1 or 2), hydroxy, $C_{1-4}$alkylsulphonyl, carbamoyl, $C_{1-4}$alkylcarbamoyl, di-($C_{1-4}$alkyl)carbamoyl, carboxy, and a 5 or 6 membered aromatic ring containing up to 4 heteroatoms independently selected from nitrogen, oxygen and sulphur;
- or a pharmaceutically acceptable salt thereof.

Another class of compound is of the formula (1) wherein:
- $R^1$ is ethyl, n-propyl, 1-methylethyl, 2-methylpropyl, 2,2-dimethylpropyl or cyclopropylmethyl;
- $R^2$ is methyl;
- $R^3$ is 4-hydroxytetrahydroisoxazin-2-ylcarbonyl or tetrahydroisoxazin-2-ylcarbonyl;
- Q is —$CH_2$—;
- Ar is selected from imidazolyl, pyrazolyl, pyrrolyl, isoxazolyl, phenyl, quinolyl, indolyl, benzimidazolyl, indazolyl, benztriazolyl, 2,3-dihydrothiazolyl, 2,3-dihydrobenzoxazolyl, pyrrolo [2,3-b]pyridyl, imidazo[1,2-a]pyridyl, imidazo[4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl, the ring system being optionally substituted by 1 or 2 substituents independently selected from methyl, ethyl, n-propyl, iso-propyl, tert-butyl, 1-methylethyl, trifluoromethyl, chloro, fluoro, bromo, hydroxymethyl, acetyl, methylthio, amino, methylamino, furanyl, thienyl, pyrimidyl, phenyl, cyano, thioxo and oxo;
- or a pharmaceutically acceptable salt thereof.

In another aspect the invention relates to a compound of general formula (1)

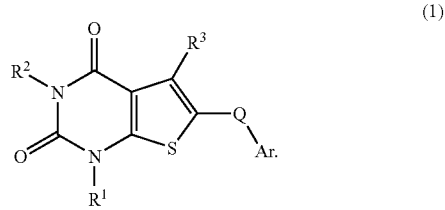

wherein:
- $R^1$ and $R^2$ each independently represent a $C_{1-6}$alkyl, $C_{3-6}$alkenyl, $C_{3-5}$cycloalkyl$C_{1-3}$alkyl or $C_{3-6}$cycloalkyl; each of which may be optionally substituted by 1 to 3 halogen atoms;
- $R^3$ is isoxazolidin-2-ylcarbonyl or tetrahydroisoxazin-2-ylcarbonyl wherein each ring is optionally substituted by one hydroxy group;
- Q is —CO— or —C($R^4$) ($R^5$)— (wherein $R^4$ is a hydrogen atom or $C_{1-4}$alkyl and $R^5$ is a hydrogen atom or hydroxy group);
- Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —($CH_2$)pN(R)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy;
- p is 1 to 4
- $R^6$ and $R^7$ each independently represent a hydrogen atom, $C_{1-4}$alkanoyl or $C_{1-4}$alkyl, or together with the nitrogen atom to which they are attached form a 5- to 7-membered saturated heterocyclic ring;
- $R^8$ and $R^9$ each independently represent a hydrogen atom, $C_{1-4}$alkanoyl or $C_{1-4}$ alkyl, or together with the nitrogen atom to which they are attached form a 5- to 7-membered saturated heterocyclic ring;
- or a pharmaceutically acceptable salt or prodrug thereof.

A particular class of compound is of the formula (1) wherein:
- $R^1$ is $C_{1-5}$alkyl or $C_{3-6}$cycloalkylmethyl;
- $R^2$ is $C_{1-5}$alkyl;
- $R^3$ is isoxazolidin-2-ylcarbonyl or tetrahydroisoxazin-2-ylcarbonyl wherein each ring is optionally substituted by one hydroxy group;

Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically acceptable salt thereof.

Another class of compound is of the formula (1) wherein:
$R^1$ is $C_{1-5}$alkyl or $C_{3-6}$cycloalkylmethyl;
$R^2$ is $C_{1-5}$alkyl;
$R^3$ is hydroxytetrahydroisoxazin-2-ylcarbonyl or hydroxytetrahydroisoxazin-2-ylcarbonyl;
Q is —CO— or —$CH_2$—;
Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically acceptable salt thereof.

Another class of compound is of the formula (1) wherein:
$R^1$ is $C_{1-5}$alkyl or $C_{3-6}$cycloalkylmethyl;
$R^2$ is methyl;
$R^3$ is hydroxyisoxazolidin-2-ylcarbonyl or hydroxytetrahydroisoxazin-2-ylcarbonyl;
Q is —CO— or —$CH_2$—;
Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically acceptable salt thereof.

Another class of compound is of the formula (1) wherein:
$R^1$ is ethyl, n-propyl, 1-methylethyl, 2-methylpropyl, 2,2-dimethylpropyl or cyclopropylmethyl;
$R^2$ is methyl;
$R^3$ is hydroxyisoxazolidin-2-ylcarbonyl or hydroxytetrahydroisoxazin-2-ylcarbonyl;
Q is —CO— or —$CH_2$—;
Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically acceptable salt thereof.

Another particular class of compound is of the formula (1) wherein:
$R^1$ is ethyl, n-propyl, 1-methylethyl, 2-methylpropyl, 2,2-dimethylpropyl or cyclopropylmethyl;
$R^2$ is methyl;
$R^3$ is hydroxyisoxazolidin-2-ylcarbonyl;
Q is —CO— or —$CH_2$—;
Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl, (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$allyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically acceptable salt thereof.

Another class of compound is of the formula (1) wherein:
$R^1$ is ethyl, n-propyl, 1-methylethyl, 2-methylpropyl, 2,2-dimethylpropyl or cyclopropylmethyl;
$R^2$ is methyl;
$R^3$ is hydroxyisoxazolidin-2-ylcarbonyl;
Q is —O— or —$CH_2$—;
Ar is selected from imidazolyl, pyrazolyl, 2,3-dihydrothiazolyl, quinolyl, indolyl, benzimidazolyl, indazolyl, pyrrolo[2,3-b]pyridinyl, 1H-1,2,3-benzotriazolyl, 2,3-dihydrobenzothiazolyl, 2,3- dihydrobenzimidazolyl, 2,3-dihydrobenzoxazolyl and 1,3-thiazolo[5,4-b]pyridinyl, the ring system being optionally substituted by 1, 2 or 3 substituents independently selected from $C_{1-4}$alkyl (optionally substituted by 1, 2 or 3 hydroxy group), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically acceptable salt thereof.

Another class of compound is of the formula (1) wherein:
$R^1$ is n-propyl, 1-methylethyl or 2-methylpropyl;
$R^2$ is methyl;
$R^3$ is 4-hydroxyisoxazolidin-2-ylcarbonyl;
Q is —CO— or —$CH_2$—;
Ar is selected from imidazolyl, pyrazolyl, 2,3-dihydrothiazolyl, quinolyl, indolyl, benzimidazolyl, pyrrolo [2,3-b]pyridinyl, 1H-1,2,3-benzotriazolyl, 2,3-dihydrobenzothiazolyl, 2,3-dihydrobenzoxazolyl and 1,3-thiazolo[5,4-b]pyridinyl, the ring system being optionally substituted by 1, 2 or 3 substituents independently selected from methyl, ethyl, propyl, tert-butyl, chloro, fluoro, thioxo, hydroxymethyl, methylthio, amino, methylamino and oxo;

or a pharmaceutically acceptable salt thereof.

Particular compounds of the present invention include:
(S)-5-[4-hydroxyisoxazolidin-2-ylcarbonyl]-3-methyl-1-(2-methylpropyl)-6-(4-quinolinylmethyl)thieno[2,3-d]pyrimidine-2,4(1H,3H)-dione;
(R) 5-[4-hydroxyisoxazolidin-2-ylcarbonyl]-3-methyl-1-(2-methylpropyl)-6-(4-quinolinylmethyl)thieno[2,3-d]pyrimidine-2,4(1H,3H)-dione;
(S) 6-[4,5-dichloro-2-methyl-1H-imidazol-1-ylmethyl]-5-[4-hydroxy-2-isoxazolidinylcarbonyl]-3-methyl-1-(2-methylpropyl)thieno[2,3-d]pyrimidine-2,4(1H,3H)-dione;
(S) 5-[4-hydroxyisoxazolidin-2-ylcarbonyl]-3-methyl-1-(2-methylpropyl)-6-(4-quinolinylcarbonyl)thieno[2,3-d]pyrimidine-2,4(1H,3H)-dione;
(S) 5-[4-hydroxyisoxazolidin-2-ylcarbonyl]-3-methyl-6-[(2-methyl-1H-indol-3-yl)methyl]-1-(2-methylpropyl)thieno[2,3-d]pyrimidine-2,4(1H,3H)-dione;
(S) 5-[4-hydroxyisoxazolidin-2-ylcarbonyl]-3-methyl-1-(2-methylpropyl)-6-[(1H-pyrrolo[2,3-b]pyridin-3-yl)methyl]thieno[2,3,d]pyrimidine-2,4(1H,3H)-dione;
(S) 5-[4-hydroxyisoxazolidin-2-ylcarbonyl]-3-methyl-6-[(2-methyl-1H-indol-3-yl)carbonyl]-1-(2-methylpropyl)thieno[2,3-d]pyrimidine-2,4(1H,3H)-dione;
(S) 5-[4-hydroxyisoxazolidin-2-ylcarbonyl]-3-methyl-1-(1-methylethyl)-6-(1H-pyrrolo[2,3-b]pyridin-3-ylmethyl)thieno[2,3-d]pyrimidine-2,4(1H,3H)-dione;
(S) 5-[4-hydroxyisoxazolidin-2-ylcarbonyl]-3-methyl-1-propyl-6-(1H-pyrrolo[2,3-b]pyridin-3-ylmethyl)thieno[2,3-d]pyrimidine-2,4(1H,3H)-dione;
(S) 6-[4,5-dichloro-2-oxo-3(2H)-thiazolylmethyl]-5-[4-hydroxyisoxazolidin-2-ylcarbonyl]-3-methyl-1-(2-methylpropyl)-thieno[2,3-d]pyrimidine-2,4(1H,3H)-dione;
(S) 6-[(3,5-dimethyl-1H-pyrazol-4-yl)methyl]-5-{4-hydroxyisoxazolidin-2-ylcarbonyl}-1-isobutyl-3-methylthieno[2,3-d]pyrimidine-2,4(1H,3H)-dione;
(S) 5-{4-hydroxyisoxazolidin-2-ylcarbonyl}-1-isobutyl-3-methyl-6-[1,3,5-trimethyl-1H-pyrazol-4-ylmethyl]thieno [2,3-d]pyrimidine-2,4(1H,3H)-dione;
(R) 6-[(4,5-dichloro-2-methyl-1H-imidazol-1-yl)methyl]-5-[4-hydroxy-isoxazolidin-2-ylcarbonyl]-3-methyl-1-(2-methylpropyl)thieno[2,3-d]pyrimidine-2,4(1H,3H)-dione;
(S) 5-[4-hydroxyisoxazolidin-2-ylcarbonyl]-3-methyl-6-[(2-methyl-1H-benzimidazol-1-yl)methyl]-1-(2-methylpropyl)thieno[2,3-d]pyrimidine-2,4(1H,3H)-dione;
(S) 6-[(2-ethyl-1H-benzimidazol-1-yl)methyl]-5-[4-hydroxyisoxazolidin-2-ylcarbonyl]-3-methyl-1-(2-methylpropyl)thieno[2,3-d]pyrimidine-2,4(1H,3H)-dione;
(S) 5-[4-hydroxyisoxazolidin-2-ylcarbonyl]-3-methyl-1-(2-methylpropyl)-6-[(2-propyl-1H-benzimidazol-1-yl)methyl]thieno[2,3-d]pyrimidine-2,4(1H,3H)-dione;
(S) 5-[4-hydroxyisoxazolidin-2-ylcarbonyl]-3-methyl-1-(2-methylpropyl)-6-[2-(methylthio)-1H-benzimidazol-1-ylmethyl]thieno[2,3-d]pyrimidine-2,4(1H,3H)-dione;
(S) 5-[4-hydroxyisoxazolidin-2-ylcarbonyl]-6-[2-(hydroxymethyl)-1H-benzimidazol-1-ylmethyl]-3-methyl-1-(2-methylpropyl)thieno[2,3-d]pyrimidine-2,4(1H,3H)-dione;
(S) 5-[4-hydroxyisoxazolidin-2-ylcarbonyl]-3-methyl-6-[2-(methylamino)-1H-benzimidazol-1-ylmethyl]-1-(2-methylpropyl)thieno[2,3-d]pyrimidine-2,4(1H,3H)-dione;
(S) 5-[4-hydroxyisoxazolidin-2-ylcarbonyl]-3-methyl-6-[2-amino-1H-benzimidazol-1-ylmethyl]-1-(2-methylpropyl) thieno[2,3-d]pyrimidine-2,4(1H,3H)-dione;
(S)-5-[4-hydroxy-2-isoxazolidinylcarbonyl]-3-methyl-1-(2-methylpropyl)-6-[(2,4,5-trichloro-1H-imidazol-1-ylmethyl]thieno[2,3-d]pyrimidine-2,4(1H,3H)-dione;
(S) 5-[4-hydroxyisoxazolidin-2-ylcarbonyl]-3-methyl-1-(02-methylpropyl)-6-[2-thioxo-3(2H)-benzothiazolylmethyl]thieno[2,3-d]pyrimidine-2,4(1H,3H)-dione;
(S) 5-[4-hydroxyisoxazolidin-2-ylcarbonyl]-3-methyl-1-(2-methylpropyl)-6-[4-chloro-2-oxo-3(2H)-thiazolylmethyl]-thieno[2,3-d]pyrimidine-2,4(1H,3H)-dione;
(S) 5-{4-hydroxyisoxazolidin-2-ylcarbonyl}-3-methyl-1-(2-methylpropyl)-6-[2-oxo-1,3-benzoxazol-3(2H)-ylmethyl] thieno[2,3-d]pyrimidine-2,4(1H,3H)-dione;
(S) 5-{4-hydroxyisoxazolidin-2-ylcarbonyl}-3-methyl-1-(2-methylpropyl)-6-[(2-oxo[1,3]thiazolo[5,4-b]pyridin-1-(2H)-yl)methyl]thieno[2,3-d]pyrimidine-2,4(1H,3H)-dione;
(S) 5-[4-hydroxyisoxazolidin-2-ylcarbonyl]-3-methyl-1-(2-methylpropyl)-6-(1H-1,2,3-benzotriazol-1-ylmethyl)-thieno[2,3-d]pyrimidine-2,4(1H,3H)-dione;
(S) 5-[4-hydroxyisoxazolidin-2-ylcarbonyl]-3-methyl-1-(2-methylpropyl)-6-(1H-pyrrolo[2,3-b]pyridin-1-ylmethyl) thieno[2,3-d]pyrimidine-2,4(1H,3H)-dione;
(S) 5-[4-hydroxyisoxazolidin-2-ylcarbonyl]-3-methyl-1-(2-methylpropyl)-6-[(2-methyl-1H-pyrrolo[2,3-b]pyridin-1-ylmethyl]thieno[2,3-d]pyrimidine-2,4(1H,3H)-dione;
(S) 1-[1,2,3,4-tetrahydro-5-[4-hydroxyisoxazolidin-2-ylcarbonyl]-3-methyl-1-(2-methylpropyl)-2,4-dioxothieno[2, 3-d]pyrimidin-6-ylmethyl]-1H-indole-5-carbonitrile;
(S) 5-{4-hydroxyisoxazolidin-2-ylcarbonyl}-3-methyl-1-(2-methylpropyl)-6-[2-oxo-1,3-benzothiazol-3(2H)-ylmethyl]thieno[2,3-d]pyrimidine-2,4(1H,3H)-dione;
(R) 5-[4-hydroxyisoxazolidin-2-ylcarbonyl]-3-methyl-6-[2-methyl-1H-indol-3-ylmethyl]-1-(2-methylpropyl)thieno [2,3-d]pyrimidine-2,4(1H,3H)-dione;

(R) 5-[4-hydroxyisoxazolidin-2-ylcarbonyl]-3-methyl-6-[7-methyl-1H-indol-3-ylmethyl]-1-(2-methylpropyl)thieno[2,3-d]pyrimidine-2,4(1H,3H)-dione;

(S) 5-[4-hydroxyisoxazolidin-2-ylcarbonyl]-3-methyl-6-[2-(methylamino)-3H-imidazo[4,5-b]pyridin-3-ylmethyl]-1-propyl-thieno[2,3-d]pyrimidine-2,4(1H,3H)-dione;

(S) 6-[4,5-dichloro-2-methyl-1H-imidazol-1-ylmethyl]-5-[4-hydroxy-2-isoxazolidinylcarbonyl]-3-methyl-1-propyl-thieno[2,3-d]pyrimidine-2,4(1H,3H)-dione;

(S) 5-[4-hydroxyisoxazolidin-2-ylcarbonyl]-3-methyl-6-[2-(methylamino)-1H-benzimidazol-1-ylmethyl]-1-(1-methylethyl)thieno[2,3-d]pyrimidine-2,4(1H,3H)-dione;

(S) 6-[4,5-dichloro-2-methyl-1H-imidazol-1-ylmethyl]-5-[4-hydroxy-2-isoxazolidinylcarbonyl]-3-methyl-1-(1-methylethyl)thieno[2,3-d]pyrimidine-5-carboxamide;

(S) 6-[3,5-diethyl-1H-pyrazol-4-ylmethyl]-5-{4-hydroxyisoxazolidin-2-yl]arbonyl}-3-methyl-1-(2-methylpropyl)thieno[2,3-d]pyrimidine-2,4(1H,3H)-dione;

(S) 6-[3,5-diethyl-1H-pyrazol-4-ylmethyl]-5-{4-hydroxyisoxazolidin-2-yl]carbonyl}-3-methyl-1-(2-methylpropyl)thieno[2,3-d]pyrimidine-2,4(1H,3H)-dione;

(S) 5-[4-hydroxyisoxazolidin-2-ylcarbonyl]-3-methyl-1-(2-methylpropyl)-6-[2-methyl-4-quinolinylmethyl]thieno[2,3-d]pyrimidine-2,4(1H,3H)-dione;

(S) 6-[6-fluoro-4-quinolinylmethyl]-5-{4-hydroxyisoxazolidin-2-ylcarbonyl}-3-methyl-1-(2-methylpropyl)thieno[2,3-d]pyrimidine-2,4(1H,3H)-dione;

(S) 6-[8-fluoro-4-quinolinylmethyl]-5-{4-hydroxyisoxazolidin-2-ylcarbonyl}-3-methyl-1-(2-methylpropyl)-thieno[2,3-d]pyrimidine-2,4(1H,3H)-dione;

(S) 5-{4-hydroxyisoxazolidin-2-ylcarbonyl)-3-methyl-1-(2-methylpropyl)-6-(5-quinolinylmethyl)thieno[2,3-d]pyrimidine-2,4(1H,3H)-dione;

(S) 5-(4-hydroxyisoxazolidin-2-ylcarbonyl}-3-methyl-1-propyl-6-(quinolin-4-ylmethyl)thieno[2,3-d]pyrimidine-2,4(1H,3H)-dione;

(S) 5-{4-hydroxyisoxazolidin-2-ylcarbonyl}-3-methyl-1-(1-methylethyl)-6-(4-quinolinylmethyl)thieno[2,3-d]pyrimidine-2,4(1H,3H)-dione;

(S) 5-[4-hydroxyisoxazolidin-2-ylcarbonyl]-3-methyl-1-(2-methylpropyl)-6-[(2-methyl-1H-pyrrolo[2,3,b]pyridin-3-yl)methyl]thieno[2,3,d]pyrimidine-2,4(1H,3H)-dione;

(R) 5-[4-hydroxyisoxazolidin-2-ylcarbonyl]-3-methyl-1-(2-methylpropyl)-6-[(2-methyl-1H-pyrrolo[2,3,b]pyridin-3-yl)methyl]thieno[2,3,d]pyrimidine-2,4(1H,3H)-dione;

(S)-5-[4-hydroxyisoxazolidin-2-ylcarbonyl]-3-methyl-1-(isobutyl)-6-[2,3-dihydro-6-methyl-3-oxo-pyrazin-2-ylmethyl]-thieno[2,3-d]pyrimidine-2,4(1H,3H)-dione;

(S) 5-[4-hydroxyisoxazolidin-2-ylcarbonyl]-3-methyl-6-[(2-methyl)-1H-pyrrolo[2,3-b]pyridin-3-yl)methyl]-1-propyl-thieno[2,3-d]pyrimidine-2,4(1H,3H)-dione;

5-[(4S)₄-hydroxyisoxazolidin-2-ylcarbonyl]—[2-(hydroxymethyl)-1H-benzimidazol-1-ylmethyl]-3-methyl-1-propyl-thieno[2,3-d]pyrimidine-2,4(1H,3H)-dione;

5-[(4S)-4-hydroxyisoxazolidin-2-ylcarbonyl]-3-methyl-1-propyl-6-[2-amino-1H-benzimidazol-1-ylmethyl]-thieno[2,3-d]pyrimidine-2,4(1H,3H)-dione;

(S)-5-[4-hydroxyisoxazolidin-2-ylcarbonyl]-6-[2-(hydroxymethyl)-1H-benzimidazol-1-yl methyl]-3-methyl-1-(isopropyl)thieno[2,3-d]pyrimidine-2,4(1H,3H)-dione;

(S)-5-[4-hydroxyisoxazolidin-2-ylcarbonyl]-3-methyl-1-(isopropyl)-6-[2-amino-1H-benzimidazol-1-ylmethyl]thieno[2,3-d]pyrimidine-2,4(1H,3H)-dione;

(S)-5-[4-hydroxyisoxazolidin-2-ylcarbonyl]-3-methyl-1-(isopropyl)-6-[methyl-1H-pyrrolo[2,3-b]pyridin-1-ylmethyl]thieno[2,3-d]pyrimidine-2,4(1H,3H)-dione;

(S) 5-[4-hydroxyisoxazolidin-2-ylcarbonyl]-3-methyl-1-(isopropyl)-6-[2-methyl-1H-pyrrolo[2,3-b]pyridin-3-ylmethyl]thieno[2,3-d]pyrimidine-2,4(1H,3H)-dione;

(S)-6-[4,5-dichloro-2-(hydroxymethyl)-1H-imidazol-1-yl methyl]-5-[4-hydroxyisoxazolidin-2-ylcarbonyl]-3-methyl-1-(isobutyl)-thieno[2,3-d]pyrimidine-2,4(1H,3H)-dione;

(S)-6-[3,5-dimethyl-1H-pyrazol-1-yl methyl]-5-[4-hydroxy-isoxazolidin-2-ylcarbonyl]-3-methyl-1-(isobutyl)-thieno[2,3-d]pyrimidine-2,4(1H,3H)-dione;

(S)-6-[2,3-dihydro-2-oxo-1H-benzimidazol-1-ylmethyl]-5-[4-hydroxyisoxazolidin-2-yl carbonyl]-3-methyl-1-(isobutyl)-thieno[2,3-d]pyrimidine-2,4(1H,3H)-dione;

(S) 6-[3,5-dimethyl-1H-pyrazol-4-ylmethyl]-5-[4-hydroxy-isoxazolidin-2-yl carbonyl]-3-methyl-1-propylthieno[2,3-d]pyrimidine-2,4(1H,3H)-dione;

(S) 6-[3,5-dimethyl-1H-pyrazol-4-ylmethyl]-5-[4-hydroxy-isoxazolidin-2-ylcarbonyl]-1-isopropyl-3-methylthieno[2,3-d]pyrimidine-2,4(1H,3H)-dione;

(S)-6-[3,5-dimethylisoxazol-4-ylmethyl]-5-[4-hydroxyisoxazolidin-2-ylcarbonyl]-1-(isobutyl)-3-methylthieno[2,3-d]pyrimidine-2,4(1H,3H)-dione;

6-[4,5-dichloro-2-methyl-1H-imidazol-1-ylmethyl]-1-ethyl-5-[(4S)-4-hydroxy-2-isoxazolidinylcarbonyl]-3-methyl-thieno[2,3-d]pyrimidine-2,4(1H,3H)-dione;

1-ethyl-5-[(4S)-4-hydroxy-2-isoxazolidinylcarbonyl]-3-methyl-6-(1H-pyrrolo[2,3-b]pyridin-3-ylmethyl)-thieno[2,3-d]pyrimidine-2,4(1H,3H)-dione;

1-ethyl-5-[(4S)-4-hydroxy-2-isoxazolidinylcarbonyl]-3-methyl-6-[2-propyl-1H-benzimidazol-1-yl methyl]-thieno[2,3-d]pyrimidine-2,4(1H,3H)-dione;

1-ethyl-5-[(4S)-4-hydroxy-2-isoxazolidinylcarbonyl]-3-methyl-6-[2-oxo-3(2H)-benzothiazolylmethyl]-thieno[2,3-d]pyrimidine-2,4(1H,3H)-dione;

1-ethyl-5-[(4S)-4-hydroxy-2-isoxazolidinylcarbonyl]-3-methyl-6-[2-methyl-1H-pyrrolo[2,3-b]pyridin-3-ylmethyl]thieno[2,3-d]pyrimidine-2,4(1H,3H)-dione;

1-ethyl-5-[(4S)-4-hydroxy-2-isoxazolidinylcarbonyl]-3-methyl-6-[5-cyano-1H-indol-1-ylmethyl]-thieno[2,3-d]pyrimidine-2,4(1H,3H)-dione;

5-[(4S)-4-hydroxyisoxazolidin-2-ylcarbonyl]-1-(isobutyl)-6-[1-isopropyl-3,5-dimethyl-1H-pyrazol-4-ylmethyl]-3-methylthieno[2,3-d]pyrimidine-2,4(1H,3H)-dione;

5-[(4S)-4-hydroxyisoxazolidin-2-ylcarbonyl]-1-(isobutyl)-3-methyl-6-[5-methyl-3-phenyl-1H-pyrazol-4-ylmethyl]thieno[2,3-d]pyrimidine-2,4(1H,3H)-dione;

5-[(4S)-4-hydroxyisoxazolidin-2-ylcarbonyl]-1-isobutyl-3-methyl-6-[5-methyl-3-(trifluoromethyl)-1H-pyrazol-4-ylmethyl]thieno[2,3-d]pyrimidine-2,4(1H,3H)-dione;

5-[(4S)-4-hydroxyisoxazolidin-2-ylcarbonyl]-1-isobutyl-6-[3-isopropyl-5-methyl-1H-pyrazol-4-ylmethyl]-3-methylthieno[2,3-d]pyrimidine-2,4(1H,3H)-dione;

6-[3,5-dimethyl-1-phenyl-1H-pyrazol-4-ylmethyl]-50-[(4S)-4-hydroxyisoxazolidin-2-ylcarbonyl]-1-isobutyl-3-methylthieno[2,3-d]pyrimidine-2,4(1H,3H)-dione;

6-[3,5-dimethyl-1-phenyl-1H-pyrazol-4-ylmethyl]-5-[(4S)-4-hydroxyisoxazolidin-2-ylcarbonyl]-3-methyl-1-propylthieno[2,3-d]pyrimidine-2,4(1H,3H)-dione;

6-(1H-1,2,3-benzotriazol-1-ylmethyl)-5-[(4S)-4-hydroxy-isoxazolidinylcarbonyl]-3-methyl-1-(isopropyl)-thieno[2,3-d]pyrimidine-2,4(1H,3H)-dione;

5-[(4s)-4-hydroxyisoxazolidinylcarbonyl]-3-methyl-1-(isopropyl)-6-[(2-oxothiazolo[5,4-b]pyridin-1(2h)-yl)methyl]-thieno[2,3-d]pyrimidine-2,4(1h, 3h)-dione;

6-[2,3-dihydro-2-oxo-1h-benzimidazol-1-ylmethyl]-5-[(4s)-4-hydroxyisoxazolidinylcarbonyl]-3-methyl-1-(isopropyl)-thieno[2,3-d]pyrimidine-2,4(1h,3h)-dione;

6-[5,6-difluoro-2,3-dihydro-2-oxo-1H-benzimidazol-1-ylmethyl]-5-[(4S)-4-hydroxy-2-isoxazolidinylcarbonyl]-3-methyl-1-(isobutyl)-thieno[2,3-d]pyrimidine-2,4(1H,3H)-dione;

5-[(4S)-4-hydroxyisoxazolidin-2-ylcarbonyl]-6-(imidazo[1,2-a]pyridin-3-ylmethyl)-1-isobutyl-3-methylthieno[2,3-d]pyrimidine-2,4(1H,3H)-dione;

3-methyl-6-[2-methylindol-3-ylmethyl]-1-(isobutyl)-5-(tetrahydroisoxazin-2-ylcarbonyl)-thieno[2,3-d]pyrimidine-2,4(1H,3H)-dione;

6-[2-bromo-4,5-dichloro-1H-imidazol-1-ylmethyl]-5-[(4S)-4-hydroxyisoxazolidinylcarbonyl]-3-methyl-1-(isobutyl)thieno[2,3-d]pyrimidine-2,4(1H,3H)-dione;

5-[(4S)$_4$-hydroxyisoxazolidin-2-ylcarbonyl]-3-methyl-1-(isobutyl)-6-[2-(methylthio)1H-imidazo[4,5-b]pyridin-1-ylmethyl]-thieno[2,3-d]pyrimidine-2,4(1H,3H)-dione;

5-[(4S)-4-hydroxyisoxazolidinylcarbonyl]-3-methyl-1-(isobutyl)-6-[2-(methylthio)-3H-imidazo[4,5-b]pyridin-3-ylmethyl]-thieno[2,3-d]pyrimidine-2,4(1H,3H)-dione;

6-[3,5-dimethyl-1H-pyrazol-4-ylmethyl]-3-ethyl-5-[(4S)-4-hydroxy-2-isoxazolidinylcarbonyl]-1-(isopropyl)-thieno[2,3-d]pyrimidine-2,4(1H,3H)-dione;

5-[(4S)-4-hydroxy-2-isoxazolidinylcarbonyl]-3-methyl-1-(isobutyl)-6-[2-(trifluoromethyl)phenylmethyl]-thieno[2,3-d]pyrimidine-2,4(1H,3H)-dione;

5-[(4S)-4-hydroxy-2-isoxazolidinylcarbonyl]-3-methyl-1-(isobutyl)-6-[2-(methylthio)-1H-imidazol-1-ylmethyl]-thieno[2,3-d]pyrimidine-2,4(1H,3H)-dione; and (S)-5-[4-hydroxyisoxazolidin-2-ylcarbonyl]-3-methyl-1-(isobutyl)-6-[2,3-dihydro-6-methyl-3-oxo-pyrazin-2-ylmethyl]-thieno[2,3-d]pyrimidine-2,4(1H,3H)-dione;

and pharmaceutically acceptable salts thereof.

Synthesis of Compounds of the Formula (1)

Compounds of formula (1) may be prepared by a number of processes as generally described hereinbelow and more specifically in the Examples hereinafter. Processes for the preparation of novel compounds of formula (1), are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated, which are within the ordinary skill of an organic chemist.

Thus according to another aspect of the invention, a compound of the formula (1) may be formed by deprotecting a compound of the formula (1) wherein at least 1 functional group is protected. For example, amino or hydroxy groups may be protected during the reaction sequence used to prepare a compound of the formula (1).

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a tri-(1-4C)alkylsilyl group (especially trimethylsilyl or tert-butyldimethylsilyl), an aryldi-(1-4C)alkylsilyl group (especially dimethylphenylsilyl), a diaryl-(1-4C)alkylsilyl group (especially tert-butyldiphenylsilyl), a (1-4C)alkyl group (especially methyl), a (2-4C)alkenyl group (especially allyl), a (1-4C)alkoxymethyl group (especially methoxymethyl) or a tetrahydropyranyl group (especially tetrahydroyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, particularly, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1-4C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2-4C)alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

The protection and deprotection of functional groups is fully described in 'Protective Groups in Organic Chemistry', edited by J. W. F. McOmie, Plenum Press (1973) and 'Protective Groups in Organic Synthesis', $2^{nd}$ edition; T. W. Greene and P. G. M. Wuts, Wiley-Interscience (1991).

A compound of the formula (1), or a compound of the formula (1) wherein at least 1 functional group is protected, may be prepared using one of the following processes:

a) reacting a compound of the formula (10):

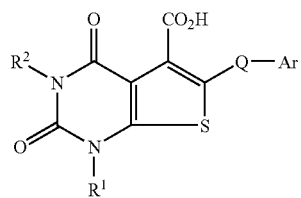

(10)

with isoxazolidine or tetrahydroisoxazine (each being optionally substituted by a hydroxy group);

b) when Q is methylene, reacting a compound of the formula (11):

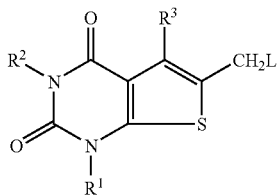

(11)

with a compound of the formula Ar;

c) when Q is methylene, reducing a compound of the formula (12):

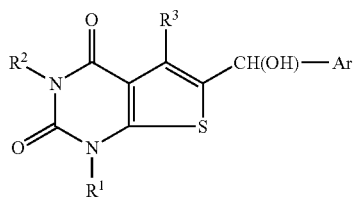

(12)

d) reacting a compound of the formula (11) or (13) to form Ar by primary ring synthesis:

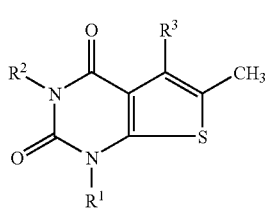

(13)

e) reacting a compound of the formula (14) with $R^1$-$L^2$:

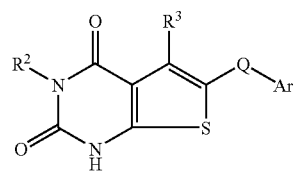

(14)

wherein L and $L^2$ are leaving groups and $R^1$, $R^2$, $R^3$, Q and Ar are as hereinabove defined and optionally after a), b), c) or d), converting the compound of the formula (1) into a further compound of formula (1) and/or forming a pharmaceutically acceptable salt or solvate thereof.

The reaction between a compound of the formula (10) and isoxazolidine or tetrahydroisoxazine (optionally substituted by a hydroxy group) is conveniently carried out under amide bond forming reaction conditions. For example, in the presence of a coupling agent such as dicyclohexylcarbodiimide or 1-ethyl-3-(3-dimethylaminopropyl)ethylcarbodiimide. Optionally a base may be used, particularly an organic base such as triethylamine. Suitable solvents are usually aprotic solvents, for example dimethylformamide or chlorinated solvents, for example dichloromethane or trichloromethane. Additionally, a compound which catalyses this type of amide bond formation reaction, such as 1-hydroxybenzotriazole, may be present. The temperature is usually in the range of about −30° C. to about 60° C., particularly at or near ambient temperature.

The reaction between a compound of the formula (11) and Ar is normally carried out in the presence of a strong base such as sodium hydride. Suitable leaving groups include halo, in particular bromo. The reaction is conveniently carried out in an inert solvent such as tetrahydrofuran, particularly at or around ambient temperature. In some circumstances, for example when Ar contains ring nitrogen atoms which do not need to be deprotonated, a milder base, such as sodium bicarbonate can be used. This reaction is conveniently used to prepare compounds in which Ar is linked through a ring nitrogen atom. However, it is possible to use this process to prepare a compound in which Ar is linked via a ring carbon atom. This can be achieved by using a strong base and a zinc salt such as zinc chloride and optionally sodium iodide as a catalyst.

A compound of formula (12) can be reduced to the corresponding methylene compound using standard reduction conditions for hydroxy groups known in the art. For example, it can be protonated with an acid such as trifluoroacetic acid and reduced with a trialkylsilane. Alternatively the hydroxy group could be converted to a stronger leaving group, such as mesylate or tosylate and the resulting compound hydrogenated in a non-hydroxylic solvent, particularly tetrahydrofuran, with a catalyst such as palladium on charcoal, in a temperature range of 0° C. to 50° C., particularly at ambient temperature and a pressure of 1 to 5 bar.

The group —Q-Ar is conveniently formed on a compound of formula (11) or (13) by primary ring synthesis. Here, reference is made to the compendiums 'The Chemistry of Heterocyclic Compounds' E. C. Taylor and A. Weissberger (published by John Wiley and Sons) and 'Comprehensive Heterocyclic Chemistry', A. R Katritzky and C. W Rees (published by Pergamon Press (Elsevier)). For examples of the preparation of a compound of the formula (1) wherein Ar is 3,5-dimethylpyrazol-4-yl or 1,3,5-trimethylpyrazol-4-yl see examples 11 and 12 in the specific examples.

A compound of the formula (14) may be reacted with a compound of formula $R^1$-$L^2$ in the presence of a mild base, such as potassium carbonate, in a dipolar aprotic solvent such as DMF, in a temperature range of ambient temperature to 170° C.

A compound of the formula (1) may be prepared from another compound of formula (1) by chemical modification. For example a compound of the formula (1) wherein Q is methylene can be oxidised to a compound of the formula (1) wherein Q is carbonyl. A preferred oxidising agent is 2,3-dichloro-5,6-dicyano-1,4-benzoquinone (DDQ) in an inert organic solvent such as tetrahydrofuran. In some circumstances oxidation can be effected by exposure of the methylene compound to air.

Intermediates of the formulae (10) may be formed from a compound of the formula (15):

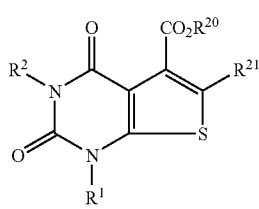

(15)

wherein $R^{20}$ is $C_{1-6}$alkyl, for example methyl or ethyl, and $R^{21}$ is either —$CH_2L$ (wherein L is as hereinabove defined) or —CH(OH)Ar.

A compound of formula (15) wherein $R^{21}$ is —$CH_2L$ may be reacted with Ar under similar conditions to those described for process b) above.

When Ar is linked via a ring carbon atom, a compound of formula (15) wherein $R^{21}$ is —CH(OH)Ar may be reduced using similar conditions to those described for process c) above.

A compound of the formula (12) or (15) wherein $R^{21}$ is —CH(OH)Ar may be formed by reacting a compound of the formula (16):

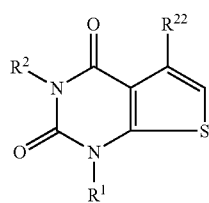

(16)

(wherein $R^{22}$ is $R^3$ or —$CO_2R^{20}$, as appropriate) with a compound of formula Ar—CHO in the presence of a strong base such as a lithium dialkylamide, for example, lithium diisopropylamide, in an inert organic solvent such as tetrahydrofuran and initially at a low temperature, such as −78° C. and subsequently allowing it to warm to ambient temperature.

The intermediates are in general prepared from a compound of the formula (17):

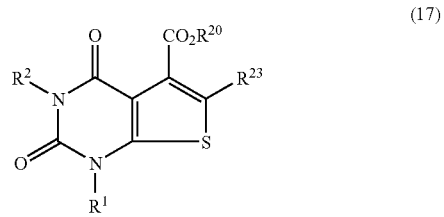

(17)

wherein $R^{23}$ is hydrogen or methyl.

When $R^{21}$ is —CH(OH)Ar, $R^{23}$ is hydrogen and the compound of formula (16) may be reacted with Ar—CHO as described above for the compound of formula (15).

When $R^{21}$ is —$CH_2L$, $R^{23}$ is methyl which is converted to —$CH_2L$ by for example halogenation. When L is bromo, the methyl group may be brominated using a standard brominating agent such as N-bromosuccinimide under standard conditions.

A compound of formula (17) wherein $R^{23}$ is hydrogen may be formed by firstly reacting a compound of formula (18):

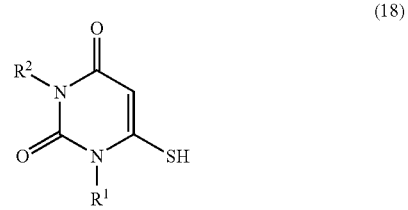

(18)

with an alkylbromopyruvate, such as ethylbromopyruvate, in the presence of a mild base such as an alkali carbonate, for example potassium carbonate in a polar solvent e.g. DMF at a temperature between 5° C. and 50° C. and then secondly treating the resulting adduct with a Lewis acid particularly titanium tetrachloride, in an inert solvent e.g. dichloromethane at a temperature between −20° C. and 50° C., particularly between 0° C. and 25° C.

A compound of formula (17) wherein $R^{23}$ is methyl may be formed by firstly reacting a compound of formula (18) with an alkyl 3-bromo-2-oxobutanoate such as methyl 3-bromo-2-oxobutanoate in the presence of a mild base such as an alkali carboxylate, for example sodium acetate in a polar solvent such as DMF, or particularly water, at a temperature between 5° C. and 50° C. and then secondly treating the resulting adduct with a Lewis acid, particularly titanium tetrachloride, in an inert solvent e.g. dichloromethane at a temperature between −20° C. and 50° C., particularly between 0° C. and 25° C.

A compound of formula (17) may be formed by reacting a compound of formula (19):

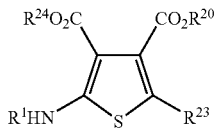
(19)

(wherein $R^{24}$ is $C_{1-4}$alkyl, for example ethyl)

with acetyl cyanate in an inert solvent, for example toluene, at a temperature of from 0° C. to 50° C., and then treating the product of that conversion with a solution of a metal alkoxide in the alkanol (eg sodium methoxide in methanol) at a temperature of from 0° C. to 30° C., in the presence of a compound of formula $R^2$-$L^1$ (wherein $L^1$ is a leaving group, eg iodide).

A compound of formula (19) may be prepared by the reaction of a compound of formula (20): $R^1$-N=S with a Wittig compound, for example a compound of the formula (21):

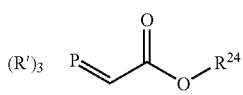
(21)

(wherein $R^1$ is phenyl or substituted phenyl such as tolyl)

in an inert solvent, for example THF, at a temperature of from 20° C. to 80° C., and treatment of the resulting adduct in situ with a compound of formula (22):

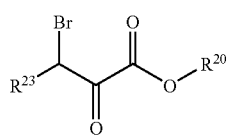
(22)

at a temperature of from −78° C. to 60° C.

A compound of formula (18) may be formed by reacting a compound of formula (23):

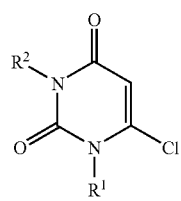
(23)

with an alkaline metal thiol, such as sodium thiol, in a polar solvent, such as an alcohol, for example ethanol, in a temperature range of 10 to 50° C.

A compound of formula (23) may be formed by reacting a compound of formula (24):

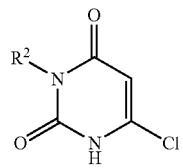
(24)

with a compound of formula $R^1$-$L^2$ under conditions described for process e) above.

The compounds of formula (1) above may be converted to a pharmaceutically acceptable salt or solvate thereof.

Certain compounds of formula (1) are capable of existing in stereoisomeric forms. It will be understood that the invention encompasses all geometric and optical isomers of the compounds of formula (1) and mixtures thereof including racemates. These also form an aspect of the present invention.

Isomers may be resolved or separated by conventional techniques, e.g. chromatography or fractional crystallisation. Enantiomers may be isolated by separation of a racemic or other mixture of the compounds using conventional techniques (e.g. chiral High Performance Liquid Chromatography (HPLC)). Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of the invention may be isolated from their reaction mixtures using conventional techniques.

The compounds of the invention are useful because they possess pharmacological activity in human and non-human animals. They are indicated as pharmaceuticals for use in the (prophylactic) treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:

(1) (the respiratory tract) airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia greata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease; and (7) cancer.

Accordingly, the present invention provides a compound of formula (1) or a pharmaceutically acceptable salt thereof as hereinbefore defined for use in therapy.

In another aspect, the present invention provides a compound of formula (1) or a pharmaceutically acceptable salt thereof as hereinbefore defined for use in inhibiting the proliferation of T cells.

In another aspect, the invention provides the use of a compound of formula (1) or a pharmaceutically acceptable salt thereof as hereinbefore defined in the manufacture of a medicament for use in inhibiting the proliferation of T cells.

In another aspect, the invention provides the use of a compound of formula (1) or a pharmaceutically-acceptable salt thereof as hereinbefore defined in the manufacture of a medicament for use in inhibiting the proliferation of T cells.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of allograft rejection) which comprises administering to a patient a therapeutically effective amount of a compound of formula (1) or a pharmaceutically-acceptable salt thereof as hereinbefore defined.

The invention still further provides a method of treating, or reducing the risk of, an airways disease (e.g. asthma or COPD) in a patient suffering from, or at risk of, said disease, which comprises administering to the patient a therapeutically effective amount of a compound of formula (1) or a pharmaceutically-acceptable salt thereof as hereinbefore defined.

For the above-mentioned therapeutic uses the dosage administered will, of course, vary with the compound employed, the mode of administration, the treatment desired and the disorder indicated. However, in general, for effecting immunosuppression, the daily dosage of the compound of formula (1) will be in the range from 0.1 mg/kg, particularly from 0.3 mg/kg, more particularly from 0.5 mg/kg and still more particularly from 1 mg/kg up to and including 30 mg/kg. For the treatment of airways diseases, the daily dosage of the compound of formula (1) will typically be in the range from 0.001 mg/kg to 30 mg/kg.

The compounds of formula (1) and pharmaceutically acceptable salts thereof may be used on their own but will generally be administered in the form of a pharmaceutical composition in which the formula (1) compound/salt/solvate (active ingredient) is in association with a pharmaceutically acceptable adjuvant, diluent or carrier. Depending on the mode of administration, the pharmaceutical composition will particularly comprise from 0.05 to 99% w (per cent by weight), more particularly less than 80% w, e.g. from 0.10 to 70% w, and even more particularly less than 50% w, of active ingredient, all percentages by weight being based on total composition.

Thus, the present invention also provides a pharmaceutical composition comprising a compound of formula (1) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (1) or a pharmaceutically acceptable salt thereof as hereinbefore defined, with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The ability of compounds which can inhibit PMA/ionomycin-stimulated peripheral blood mononuclear cell proliferation can be assessed, for example using the procedure set out below:

Inhibition of PMA/ionomycin-stimulated Peripheral Blood Mononuclear Cell Proliferation The assay for PMA/ionomycin-stimulated PBMC proliferation was performed in 96-well flat bottomed microtitre plates. Compounds were prepared as 10 mM stock solutions in dimethyl sulfoxide. A 50-fold dilution of this was prepared in RPMI and serial dilutions were prepared from this solution. 10 µl of the 50-fold diluted stock, or dilutions of it, were added to the well to give concentrations in the assay starting at 9.5 µM and going down. Into each well was placed $1 \times 10^5$ PBMC, prepared from human peripheral blood from a single donor, in RPMI1640 medium supplemented with 10% human serum, 2 mM glutamine and penicillin/streptomycin. Phorbol myristate acetate (PMA) (0.5 ng/ml final concentration) and ionomycin (500 ng/ml final concentration) were added to these cells in supplemented RPMI1640 medium (as above) so that the final volume of the assay was 0.2 ml. The cells were incubated at 37° C. in a humidified atmosphere at 5% carbon dioxide for 72 hours. $^3$H-Thymidine (0.5 µCi) was added for the final 6 hours of the incubation. The level of radioactivity incorporated by the cells was then determined and this is a measure of proliferation.

The compounds of the Examples were found to exhibit an $IA_{50}$ value of less than $1 \times 10^{-6}$ M in the above test. In the following specific examples, Example 1 had an $IA_{50}$ of $1.7 \times 10^{-7}$ M and Example 20 had an $IA_{50}$ of $5 \times 10^{-9}$ M in the above test.

The invention will now be illustrated in the following Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18-25° C. and under an atmosphere of an inert gas such as argon or nitrogen;

(iii) yields are given for illustration only and are not necessarily the maximum attainable;

(iv) the structures of the end-products of the formula (1) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), mass spectrometry (MS), infra-red (IR) or NMR analysis;

| Abbreviations | |
|---|---|
| 2,3-Dichloro-5,6-dicyano-1,4-benzoquinone | DDQ |
| Dimethylformamide | DMF |
| m-Chloroperoxybenzoic acid | mCPBA |
| Tetrahydrofuran | THF |

EXAMPLE 1

(S)-5-[4-Hydroxyisoxazolidin-2-ylcarbonyl]-3-methyl-1-(isobutyl)-6-(4-quinolinylmethyl)thieno[2,3-d]pyrimidine-2,4(1H,3H)-dione

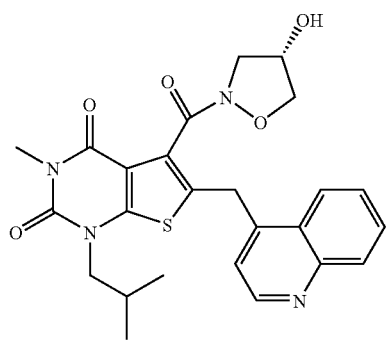

a) (S) Methyl 2-[4-hydroxyisoxazolidin-2-yl]carbonylbenzoate

Triethylamine (0.28 ml) was added to a solution of N-hydroxyphthalimide (5.00 g) and (R)-(+)-epichlorohydrin (2.40 ml) in anhydrous dioxane (10 ml) under nitrogen. The mixture was stirred at 50° C. for 48 h, further (R)-(+)-epichlorohydrin (0.24 ml) and triethylamine (0.28 ml) were added and stirring continued at 50° C. for 24 h. Methanol (10 ml) and further triethylamine (4.27 ml) were added and stirring continued at 50° C. for 2 h. The mixture was evaporated under reduced pressure, the residue dissolved in saturated aqueous sodium bicarbonate solution (100 ml) and extracted with ethyl acetate (6×100 ml). Combined organic extracts were dried over anhydrous magnesium sulfate, filtered and evaporated under reduced pressure. The residue was recrystallised from ethyl acetate to give the sub-title compound (3.4 g). MS(ESI) 252 [M+H]$^+$. δ $^1H_{CDCl_3}$ 3.66 (1H, d, br), 3.79 (1H, d, br), 3.89-3.99 (1H, m), 3.99-4.10 (1H, m), 4.74-4.81 (1H, m), 7.46 (1H, d), 7.49 (1H, t), 7.62 (1H, t), 7.99 (1H, d).

b) (S)-4-Isoxazolidinol hydrochloride

Hydrochloric acid (4M, 15 ml) was added to the product of step a) (1.87 g) and the solution heated under reflux for 3 h. The mixture was cooled to room temperature, filtered and evaporated under reduced pressure. The residue was recrystallised from propan-2-ol to give the sub-title compound as white needles (0.78 g). δ $^1H_{DMSO}$ 3.35 (1H, d), 3.47 (1H, dd), 4.03 (1H, dd), 4.07 (1H, d), 4.78-4.81 (1H, m).

c) Ethyl 1,2,3,4-tetrahydro-3-methyl-1-(isobutyl)-2,4-dioxothieno[2,3-d]pyrimidine-5-carboxylate 6-Mercapto-3-methyl-1-(isobutyl)-pyrimidine-2,4(1H,3H)-dione (49.5 g) was dissolved in dry DMF (900 ml) and ethyl bromopyruvate (30 ml) was added, and then with stirring anhydrous potassium carbonate (15.95 g) was also added. The mixture was stirred at room temperature for 5 h, and then poured into water (5 L). The aqueous solution was acidified with dil hydrochloric acid, and then extracted thoroughly with ethyl acetate. The organic extract was dried (MgSO$_4$) and evaporated at high vacuum to leave a semi-solid mass. A portion of this semisolid mass (24 g) was dissolved in methylene chloride (500 ml) and cooled in an ice-bath under an atmosphere of nitrogen. With efficient stirring titanium tetrachloride (13.5 ml) was slowly added. The reaction mixture was stirred 1 hr in the ice-bath and then 3 hr at room temperature. The reaction mixture was poured slowly into vigorously stirred ice-water (1.5 L), and then the resulting suspension was extracted into methylene chloride. After drying the organic solvent was removed in vacuo, and the residue was chromatographed (SiO$_2$/1:1 ethyl acetate-isohexane) to afford the sub-title compound as a pale yellow solid 15 g. δ $^1H_{CDCl_3}$ 1.0 (6H, d), 1.4 (3H, t), 2.31-2.45 (1H, m), 3.4 (3H, s), 3.8 (2H, d), 4.4 (2H, q), 7.28 (1H, s).

d) Ethyl 1,2,3,4-tetrahydro-6[hydroxy (4-quinolinyl)methyl]-3-methyl-1-(isobutyl)-2,4-dioxothieno[2,3-d]pyrimidine-5-carboxylate A solution of lithium diisopropylamide (5.52 g) in anhydrous THF (80 ml) was added dropwise over 1 h to a stirred solution of the product of step c) (8.02 g) and 4-quinolinecarboxaldehyde (8.12 g) in anhydrous THF (80 ml) at −78° C. under nitrogen. The mixture was stirred for a further 1 hour at −78° C. then quenched with glacial acetic acid (10 ml), allowed to warm to room temperature, diluted with saturated sodium bicarbonate solution (100 ml) and extracted into ethyl acetate (2×100 ml). The combined extracts were dried over magnesium sulfate, filtered and concentrated in vacuo. The residue was purified by column chromatography, eluting with 3:2 ethyl acetate/i-hexane, to give the sub-title compound as a white solid (7.35 g). MS(ESI) 468 {M+H]$^+$. δ $^1H_{CDCl_3}$ 0.85 (3H,d), 0.88 (3H,d), 1.43 (3H,t), 2.10-2.16 (1H,m), 3.38 (3H,s), 3.49 (1H,dd), 3.61 (1H, s,br), 3.71 (1H,dd), 4.48 (2H,quartet), 6.78 (1H,s), 7.52 (1H,t), 7.72 (1H,t), 7.83 (1H,d), 7.90 (1H,d), 8.17 (1H,d), 9.02 (1H,d)

e) Ethyl 1,2,3,4-tetrahydro-3-methyl-1-(isobutyl)-2, 4-dioxo-6-(4-quinolinylmethyl)-thieno[2,3-d]pyrimidine-5-carboxylate Trifluoroacetic anhydride (3.33 ml) was added to a solution of the product of step d) (7.34 g) and triethylamine (6.56 ml) in anhydrous THF (150 ml) at room temperature under nitrogen and the mixture stirred for 15 min. 10% palladium on charcoal (500 mg) was added and the mixture hydrogenated at 1 bar for 20 h. It was filtered through celite washing with saturated sodium bicarbonate solution (150 ml) then ethyl acetate (300 ml). The organic material was extracted into ethyl acetate (150 ml), the combined extracts were dried over magnesium sulfate, filtered and concentrated under reduced pressure. The residue was purified by column chromatography, eluting with 1:1 ethyl acetate/i-hexane, to give the sub-title compound as a solid (5.90 g). MS(ESI) 452 [M+H]$^+$. δ $^1H_{CDCl3}$ 0.90 (6H,d), 1.37 (3H,t), 2.10-2.16 (1H,m), 3.39 (3H,s), 3.64 (2H,d), 4.45 (2H,q), 4.61 (2H,s), 7.29 (1H,d), 7.60 (1H,t), 7.75 (1H,t), 8.11 (1H,d), 8.16 (1H,d), 8.89 (1H,d)

f) Sodium 1,2,3,4-tetrahydro-3-methyl-1-(isobutyl)-2,4-dioxo-6-(4-quinolinylmethyl)-thieno[2,3-d]pyrimidine-5-carboxylate A solution of the product of step e) (5.89 g) in THF (150 ml) and methanol (23 ml) under nitrogen was degassed by repeated evacuation and flushing with nitrogen. 1M sodium hydroxide (18 ml) was added and the mixture stirred for 18 h. The resulting precipitated solid was collected by filtration, washed with THF and dried in vacuo to give the sub-title compound as a solid (5.06 g). MS(ESI) 424 {M+H]$^+$. δ $^1H_{DMSO}$ 0.81 (6H,d), 2.10-2.15 (1H,m), 3.20 (3H,s), 3.56 (2H,d), 4.56 (2H,s), 7.52 (1H,dd), 7.57 (1H,td), 7.74 (1H,td), 8.00 (1H,dd), 8.83 (1H,d)

g) (S) 5-[4-Hydroxyisoxazolidin-2-ylcarbonyl]-3-methyl-1-(isobutyl)-6-(4-quinolinylmethyl)thieno[2,3-d]pyrimidine-2,4(1H,3H)-dione To a suspension of the product of step f) (157 mg) in dichloromethane (5 ml) was added 1-hydroxybenzotriazole hydrate (108 mg) and the mixture stirred for 15 minutes. 1-Ethyl-3-(3'-dimethylaminopropyl)carbodiimide hydrochloride (135 mg) was added and stirring continued for 1 h. (S)-4-Isoxazolidinol hydrochloride (Example 1, part b)) (69 mg) and triethylamine (147 μl) were added and the reaction mixture stirred for 18 h then concentrated under reduced pressure. The residue was purified by column chromatography, eluting with i-hexane/ethyl acetate (10-100% gradient) to give the title compound as a solid (136 mg). MS(APCI) 495 [M+H]$^+$. δ $^1H_{DMSO}$ 0.80-0.90 (6H, m), 2.03-2.17 (1H, m), 3.21 (1.8H, s), 3.22 (1.2H, s), 3.55-3.68 (3H, m), 3.70-4.13 (3H, m), 4.52-4.68 (2.4H, m), 4.78-4.81 (0.6H, m), 5.50 (0.4H, d), 5.54 (0.6H, d), 7.42 (0.4H, d), 7.46 (0.6H, d), 7.63 (1H, t), 7.78 (1H, t), 8.05 (1H, d), 8.24 0.4H, d), 8.28 (0.6H, d), 8.86 (1H, d).

EXAMPLE 2

(R) 5-[4-Hydroxyisoxazolidin-2-ylcarbonyl]-3-methyl-1-(isobutyl)-6-(4-quinolinylmethyl)thieno[2,3d] pyrimidine-2,4(1H,3H)-dione

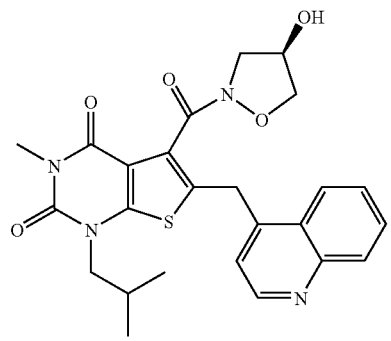

a) (R) Methyl 2-[4-hydroxyisoxazolidin-2-ylcarbonyl]benzoate

Prepared from N-hydroxyphthalimide and (S)-(+)-epichlorohydrin by the method of example 1 part a). MS(ESI) 252 [M+H]$^+$. δ $^1H_{CDCl3}$ 3.66 (1H, d, br), 3.79 (1H, d, br), 3.89-3.99 (1H, m), 3.99-4.10 (1H, m), 4.74-4.81 (1H, m), 7.46 (1H, d), 7.49 (1H, t), 7.62 (1H, t), 7.99 (1H, d).

b) (R)-4-Isoxazolidinol hydrochloride

Prepared from the product of step a) following the procedure of example 1b). δ $^1H_{DMSO}$ 3.35 (1H, d), 3.47 (1H, dd), 4.03 (1H, dd), 4.07 (1H, d), 4.78-4.81 (1H, m).

c) (R) 5-[[4-Hydroxyisoxazolidin-2-yl]carbonyl]-3-methyl-1-(isobutyl)-6-(4-quinolinylmethyl)thieno[2,3-d]pyrimidine-2,4(1H,3H)-dione To a stirred suspension of the product from example 1 part f), (200 mg) in dichloromethane (8 ml) was added hydroxybenzotriazole (90 mg) followed by 1-ethyl-3-(3'-dimethylaminopropyl)carbodiimide hydrochloride (128 mg). After 15 min, (R)-4-isoxazolidinol hydrochloride (84 mg) and triethylamine (0.093 ml) were added and stirring continued for 18 h. The resulting mixture was purified by column chromatography over silica, eluting with ethyl acetate/methanol (19:1) and the product triturated with ether to give the title-compound as a white powder (92 mg). MS (APCI) 495 [M+H]$^+$. δ m), 2.03-2.17 (1H, m), 3.21 (1.8H, s), 3.22 (1.2H, s), 3.55-3.68 (3H, m), 3.70-4.13 (3H, m), 4.52-4.68 (2.4H, m), 4.78-4.81 (0.6H, m), 5.50 (0.4H, d), 5.54 (0.6H, d), 7.42 (0.4H, d), 7.46 (0.6H, d), 7.63 (1H, t), 7.78 (1H, t), 8.05 (1H, d), 8.24 (0.4H, d), 8.28 (0.6H, d), 8.86 (1H, d).

EXAMPLE 3

(S) 6[4,5-Dichloro-2-methyl-1H-imidazol-1-ylmethyl]-5-[4-hydroxy-2-isoxazolidinylcarbonyl]-3-methyl-1-(isobutyl)thieno[2,3-d]pyrimidine-2,4(1H,3H)-dione

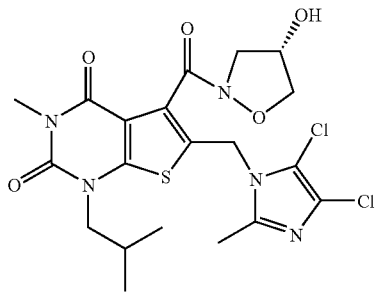

a) Methyl 1,2,3,4-tetrahydro-3,6-dimethyl-1-(isobutyl)-2,4-dioxothieno[2,3-d]pyrimidine-5-carboxylate 6-Mercapto-3-methyl-1-(isobutyl)-pyrimidine-2,4(1H,3H)-dione (50 g) was dissolved in a solution of sodium acetate (95.6 g) in water (1.5 L), and methyl 3-bromo-2-oxo-butanoate (44.6 g) was added dropwise with stirring. After stirring 1 h at room temperature the mixture was extracted into ethyl acetate. The organic solution was washed with brine, dried (MgSO$_4$) and evaporated to leave an oil. The oil (75.1 g) was dissolved in methylene chloride (800 ml) and cooled in an ice-bath under an atmosphere of nitrogen. With efficient stirring titanium tetrachloride (43.3 ml) was slowly added dropwise. The reaction mixture was stirred 1 h in the ice-bath and then 3 h at room temperature. The reaction mixture was poured slowly into vigorously stirred ice-water (2 L), and then the resulting suspension was extracted into methylene chloride. After drying, the organic solvent was removed in vacuo, and the residue was chromatographed (SiO$_2$/1:1 ethyl acetate-isohexane) to afford the sub-title compound 42 g. Trituration with isohexane gave a white powder. δ $^1$H$_{CDCl3}$ 0.98(6H,d), 2.23-2.41 (1H,m), 2.46 (3H,s), 3.4 (3H,s), 3.75 (2H,d), 3.96 (3H,s).

b) Methyl 6-(bromomethyl)-1,2,3,4-tetrahydro-3-methyl-1-(isobutyl)-2,4-dioxo-thieno[2,3-d]pyrimidine-5-carboxylate A solution of the product of step a) (10 g) and N-bromosuccinimide (5.74 g) in chloroform (350 ml) was refluxed under illumination from a tungsten lamp for 4 h. The solution was washed with water, saturated sodium bicarbonate solution and then brine. The organic layer was dried over magnesium sulfate, filtered and concentrated concentrated in vacuo. The residue was purified by flash silica chromatography eluting with isohexane:ether (1:1) to give the sub-title compound as a white powder (8.29 g). MS (APCI) 390/391 [M+H]$^+$. δ $^1$H$_{CDCl3}$ 1.00 (6H,d), 2.31 (1H,septet), 3.39 (3H,s), 3.76 (2H,dd), 3.99 (3H,s), 4.66 (2H,s).

c) Methyl 6-[4,5-dichloro-2-methyl-1H-imidazol-1-ylmethyl]-1,2,3,4-tetrahydro-3-methyl-1-(isobutyl)-2,4-dioxothieno[2,3-d]pyrimidine-5-carboxylate 4,5-Dichloro-2-methylimidazole (1.3 g) in dry tetrahydrofuran (20 ml) was added dropwise to a suspension of sodium hydride (0.34 g, 60%) in dry tetrahydrofuran (20 ml) at room temperature under nitrogen. After 15 min, a solution of the product of step b) (3.35 g) in dry tetrahydrofuran (20 ml) was added dropwise and the reaction was stirred for 3 h at room temperature. The solution was poured into water and extracted with ethyl acetate. The combined extracts were dried over magnesium sulfate, filtered and concentrated in vacuo. The residue was purified by flash silica chromatography eluting with a gradient 50-100% ethyl acetate in isohexane to give the sub-title compound as a white solid (2.28 g). MS (APCI) 459/460 [M+H]$^+$. δ $^1$H$_{CDCl3}$ 0.97 (6H,d), 2.26 (1H, septet), 2.38(3H,s), 3.39 (3H,s), 3.73 (2H,d), 3.99 (3H,s), 5.26 (2H,s).

d) 6-[(4,5-Dichloro-2-methyl-1H-imidazol-1-yl)methyl]-1,2,3,4-tetrahydro-3-methyl-1-(isobutyl)-2,4-dioxothieno[2,3-d]pyrimidine-5-carboxylic acid Sodium hydroxide (7.3 ml of 1M aqueous solution) followed by methanol (4 ml) were added to a solution of the product of step c) (2.28 g) in tetrahydrofuran (50 ml) and stirred at room temperature for 3 h. The solution was concentrated under reduced pressure. The residue was diluted with water and extracted with ethyl acetate. The combined extracts were dried over magnesium sulfate, filtered and concentrated in vacuo. The residue was purified by flash silica chromatography eluting with a gradient of 2-5% ethanol in dichloromethane to give the sub-title compound as a white solid (1.68 g). MS (APCI) 445/447 [M+H]$^+$. δ $^1$H$_{CDCl3}$ 0.96 (6H,d), 2.22 (1H, septet), 2.37 (3H,s), 3.51 (3H,s), 3.78 (2H,d), 5.78 (2H,s), 15.51 (1H,br.s).

e) 6-[(4,5-Dichloro-2-methyl-1H-imidazol-1-yl)methyl]-5-[4-(S)-hydroxy-2-isoxazolidinylcarbonyl]-3-methyl-1-(isobutyl)thieno[2,3-d]pyrimidine-2,4(1H,3H)-dione The title compound was prepared by the method of Example 1 part g). MS (APCI) 516/518 [M+H]$^+$. δ $^1$H$_{CDCl3}$ 0.98 (6H,dd); 2.29 (1H,septet); 2.39 (3H,s); 3.38 (3H,s); 3.54 (1H,dd); 3.66-3.70 (1H,m); 3.80-3.87 (1H,m); 4.04-4.10 (2H,m); 4.56 (1H,d); 4.70-4.75 (1H,m); 4.92 (1H,d); 5.13-5.30 (2H,m).

EXAMPLE 4

(S) 5-[4-Hydroxyisoxazolidin-2-ylcarbonyl]-3-methyl-1-(isobutyl)-6-(4-quinolinylcarbonyl)thieno[2,3-d]pyrimidine-2,4(1H,3H)-dione

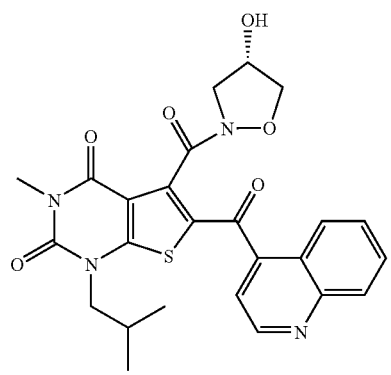

Prepared from the product of example 1 part b) (115 mg) and the product of example 1 part f) (342 mg) by the method of example 1g), followed by exposure of the product to air for 18 h. The crude material was purified by reverse-phase preparative HPLC with gradient aqueous ammonium acetate/acetonitrile elution followed by trituration with ether to give the title-compound as a white powder (22 mg). MS (APCI) 509 [M+H]$^+$. *δ $^1$H$_{DMSO}$ (130° C.*) 0.97 (6H, d), 2.23-2.33 (1H, m), 2.68-2.95 (2H, m), 3.23 (3H, s), 3.60 (1H, dd), 3.65-3.75 (1H, m), 3.81 (2H, d), 4.50 (1H, s, br), 7.56 (1H, d), 7.61 (1H, d), 7.73-7.82 (2H, m), 8.10 (1H, d), 8.97 (1H, d). (*N.B. Substance exists as a mixture of rotamers therefore NMR complicated at room temperature but simplified at elevated temperature)

EXAMPLE 5

(S) 5-[4-Hydroxyisoxazolidin-2-ylcarbonyl]-3-methyl-6-[(2-methyl-1H-indol-3-yl)methyl]-1-(isobutyl)thieno[2,3-d]pyrimidine-2.4(1H,3H)-dione

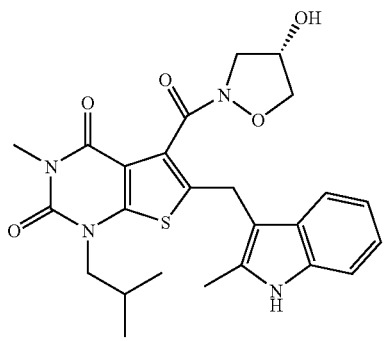

a) Methyl 1,2,3,4-tetrahydro-3-methyl-6-[(2-methyl-1H-indol-3-yl)methyl]-1-(isobutyl)-2,4-dioxothieno [2,3-d]pyrimidine-5-carboxylate A solution of the product of example 3, part a), (7 g) and N-bromosuccinimide (4.42 g) in chloroform (140 ml) was refluxed under illumination from a tungsten lamp for 2 h. The solution was cooled to room temperature, saturated aqueous sodium bicarbonate solution (140 ml) and 2-methylindole (5.92 g) were added and the mixture stirred rapidly for 48 h. The phases were separated and the aqueous phase extracted with dichloromethane (100 ml). The combined organic extracts were dried over anhydrous magnesium sulfate, filtered and evaporated under reduced pressure. The residue was purified by column chromatography over silica, eluting with ethyl acetate/i-hexane (1:3) to give the sub-title compound as a pale brown solid (6.68 g). MS(ESI) 440 [M+H]$^+$. δ $^1$H$_{CDCl_3}$ 0.87 (6H, d), 2.11-2.21 (1H, m), 2.42 (3H, s), 3.38 (3H, s), 3.61 (2H, d), 3.99 (3H, s), 4.22 (2H, s), 7.08 (1H, t), 7.15 (1H, t), 7.31 (1H, d), 7.46 (1H, d), 7.91 (1H, s, br).

b) 1,2,3,4-Tetrahydro-3-methyl-6-[(2-methyl-1H-indol-3-yl)methyl]-1-(isobutyl)-2,4-dioxothieno[2,3-d]pyrimidine-5-carboxylic acid Sodium hydroxide solution (1M, 13.6 ml) and methanol (25 ml) were added to a stirred solution of the product from step a) (4 g) in tetrahydrofuran (100 ml). After 28 h, the solution was concentrated under reduced pressure to 20 ml volume, diluted with water (200 ml) and extracted with ether (2×100 ml). The aqueous phase was acidified to pH 2 by addition of concentrated hydrochloric acid and extracted with ethyl acetate/methanol (19:1, 2×200 ml). Organic extracts were dried over anhydrous magnesium sulfate, filtered and evaporated under reduced pressure to give the sub-title compound as a white solid (4 g). MS(ESI) 426 [M+H]$^+$ δ $^1$H$_{DMSO}$ 0.80 (6H, d), 1.99-2.09 (1H, m), 2.37 (3H, s), 3.18 (3H, s), 3.59 (2H, d), 4.32 (2H, s), 6.91 (1H, t), 7.00 (1H, t), 7.26 (1H, d), 10.96 (1H, s), 14.05 (1H, s, br).

c) (S) 5-[4-Hydroxyisoxazolidin-2-ylcarbonyl]-3methyl-6-[(2-methyl-1H-indol-3-yl)methyl]-1-(isobutyl)thieno[2,3-d]pyrimidine-2,4(1H,3H)-dione Prepared from the product of part b) and (S)-4-isoxazolidinol hydrochloride [example 1, part b)] following the procedure of example 1, part g) to give the title compound as a solid. MS (APCI) 497 [M+H]$^+$. δ $^1$H$_{DMSO}$ 0.80-0.83 (6H, m), 1.98-2.08 (1H, m), 2.37 (1H, s), 3.19 (1.5H, s), 3.21 (1.5H, s), 3.50-3.65 (3H, m), 3.70-3.93 (2H, m), 4.00-4.18 (3H, m), 4.62-4.83 (1H, m), 5.50 (0.5H, d, br), 5.54 (0.5H, d), 6.90 (1H, t), 6.98 (1H, t), 7.25 (1H, d), 7.39 (0.5H, d), 7.43 (0.5H, d), 10.91 (1H, s).

EXAMPLE 6

(S) 5-[4-Hydroxyisoxazolidin-2-ylcarbonyl-3-methyl-1-(isobutyl)-6-[(1H-pyrrolo[2,3-b]pyridin-3-yl) methyl]thieno[2,3,d]pyrimidine-2,4(1H,3H)-dione

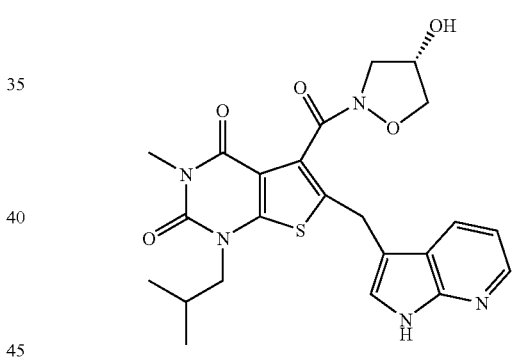

a) Methyl 1,2,3,4-tetrahydro-3-methyl-1(isobutyl)-2, 4-dioxo-6-(1H-pyrrolo[2,3,b]pyridin-3-ylmethyl) thieno[2,3d]pyrimidine-5-carboxylate To a solution of 7-azaindole (0.78 g) in dry THF (30 ml) was added 2.5M n-butyl lithium (2.6 ml) dropwise at 10° C. under nitrogen and the resulting mixture was stirred for 15 min. 1.0M ethereal zinc chloride (6.61 ml) was added, the mixture was allowed to warm to room temperature and stirred for 2 h. The solvent was removed under reduced pressure and the residue diluted with dry toluene (20 ml). A solution of example 3 part b) (3.14 g) in dry toluene (10 ml) was added followed by a catalytic amount of sodium iodide and the mixture stirred under nitrogen for 72 h. The solvent was decanted and the solid residue partitioned between 2N hydrochloric acid and ethyl acetate; the organic phase was basified with sodium bicarbonate and extracted into ethyl acetate (2×100 ml). The combined extracts were dried over magnesium sulfate, filtered and concentrated in vacuo. The residue was purified by column chromatography, eluting with i-hexane/ethyl acetate (20-75% gradient), to give the sub-title compound as a yellow solid (1.37 g). MS (APCI) 427 [M+H]⁺. δ ¹H$_{DMSO}$ 0.83 (6H,d), 2.09 (1H, heptet), 3.20 (3H,s), 3.61 (2H,d), 3.86 (3H,s), 4.22 (2H,s), 7.02-7.05 (1H,m), 7.43 (1H,m), 7.88 (1H,d), 8.20 (1H,d), 11.56 (1H, s,br)

b) 1,2,3,4-Tetrahydro-3-methyl-1 (isobutyl)-2,4-dioxo-6-(1H-pyrrolo[2,3,b]pyridin-3-ylmethyl)thieno[2,3,d]pyrimidine-5-carboxylic acid The sub-title compound was prepared from the product of step a by the method of example 3, step d). MS(ESI) 413 [M+H]⁺ c) (S) 5-[[4-hydroxyisoxazolidin-2-yl]carbonyl]-3-methyl-1-(isobutyl)-6-[(1H-pyrrolo[2,3,b]pyridin-3-yl)methyl]thieno[2,3,d]pyrimidine-2,4(1H,3H)-dione The title compound (55 mg) was prepared from the product of step b, (150 mg) by the method of example 1, step g), and (S)-4-hydroxyisoxazolidine, example 1 part b). MS (APCI) 484 [M+H]⁺. δ ¹H$_{DMSO}$ 0.82-0.85 (6H,m), 2.03-2.13 (1H,m), 3.20-3.21 (3H,m), 3.53-3.68 (3H,m), 3.75-3.90 (2H, m), 4.00-4.18 (3H,m), 4.60-4.80 (1H,m), 5.50-5.55 (1H,m), 6.99-7.02 (1H,m), 7.41-7.44 (1H,m), 7.90-7.97 (1H,m), 8.18-8.20 (1H,m), 11.53 (1H,s,br)

EXAMPLE 7

(S) 5-[4-Hydroxyisoxazolidin-2-ylcarbonyl]-3-methyl-6-[(2-methyl-1H indol-3-yl)carbonyl]-1-(isobutyl)thieno[2,3d]pyrimidine-2,4(1H,3H)-dione

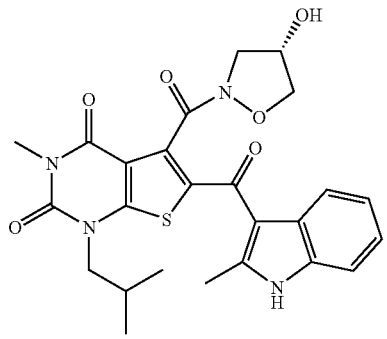

2,3-Dichloro-5,6-dicyano-1,4-benzoquinone (48 mg) was added to a stirred solution of the product of example 5 part c), 48 mg in tetrahydrofuran/water (9:1, 1 ml). After 1 h, the solution was evaporated under reduced pressure and the residue purified by reverse-phase preparative HPLC with gradient aqueous ammonium acetate/acetonitrile elution followed by recrystallisation from ether to give the title compound as a solid (20 mg). MS (APCI) 511 [M+H]⁺. δ ¹H$_{DMSO}$ 0.90 (6H, d), 2.13-2.23 (1H, m), 2.46 (3H, s), 3.23 (0.4H, s), 3.24 (0.6H, s), 3.18-3.25 (0.6H, m), 3.63-3.93 (5H, m), 4.05-4.12 (0.4H, m), 4.56-4.62 (0.6H, m), 4.70-4.76 (0.4H, m), 5.46 (1H, s, br), 7.07 (1H, t), 7.15 (1H, t), 7.39 (1H, d), 7.46-7.53 (1H, m), 12.01 (1H, s).

EXAMPLE 8

(S) 5-[4-Hydroxyisoxazolidin-2-ylcarbonyl]-3-methyl-1-(1-methylethyl)-6-(1H-pyrrolo[2,3-b]pyridin-3-ylmethyl)thieno[2,3-d]pyrimidine-2,4(1,3H)-dione a) Ethyl methyl 2-methyl-5-(N,N-methylethylamino)-thiophene-3,4-dicarboxylate Ethoxycarbonylmethylene triphenyl phosphorane (33.8 g) in dry THF (200 ml) was treated with isopropyl isothiocyanate (10.1 g) at 65° C. for 16 h under nitrogen. The mixture was cooled to −78° C. and methyl 3-bromo-2-oxo-butanoate was added. The reaction was allowed to warm slowly to room temperature. After 24 h at room temperature more methyl 3-bromo-2-oxo-butanoate (2.8 g) was added and the mixture was warmed to 60° C. for 16 h. The cooled reaction was poured into water (1.5 L) and extracted into ether. Drying and evaporation gave an oil which was chromatographed (SiO₂/10:1 isohexane-ethyl acetate then 5:1 isohexane-ethyl acetate) to afford the subtitle compound (23.5 g). δ ¹H$_{CDCl3}$ 1.23-1.35 (9H, m), 2.26 (3H,s), 3.46 (1H, m), 3.82 (3H, s), 4.2 (2H, q), 7.42 (1H, br.s)

b) Methyl 1,2,3,4-tetrahydro-3,6-dimethyl-1-(1-methylethyl)-2,4-dioxo-thieno[2,3-d]pyrimidine-5-carboxylate Silver cyanate (13.5 g) suspended in anhydrous toluene (90 ml) under nitrogen was treated dropwise with acetyl chloride (5.34 ml) and stirred vigorously for 30 min. The product of step 1) (23 g) dissolved in anhydrous toluene (15 ml) was added and the mixture was stirred for 72 h. Ether (360 ml) was added and the insoluble material was filtered off and washed with a small volume of ether. The combined organic solutions were washed with saturated sodium bicarbonate solution, dried and evaporated. The residue was treated with a solution of sodium methoxide in methanol (25 wt %, 64 ml) at room temperature for 72 h. The reaction was cooled in ice and treated with trimethylsilyl chloride (50.8 ml) and stirred at room temperature overnight. All volatiles were removed in vacuo and the residue partitioned between water and ethyl acetate. Drying and evaporation of the organic solution left a residue, which was chromatographed (SiO₂/2:1 isohexane-ethyl acetate then 3:2 isohexane-ethyl acetate) to isolate the major component (12.2 g). This was taken in dry DMF (150 ml) with potassium carbonate (6.95 g) and methyl iodide (7.1 g) for 72 h at room temperature. The mixture was poured into water (2 L), acidified and extracted into ether. Washing with brine, drying and evaporation gave a solid which was boiled in isohexane (200 ml) containing ethyl acetate (3 ml). On cooling the precipitated pale yellow solid was collected and dried, to afford the title compound (10.5 g). δ ¹H$_{CDCl3}$ 1.6 (6H, d), 2.44 (3H,s), 3.37 (3H, s), 3.95 (3H, s), 4.66 (1H, br) MS (APCI) (M⁺+H) 297 c) 6-(Bromomethyl)-1,2,3,4-tetrahydro-3-methyl-1-(1-methylethyl)-2,4-dioxothieno[2,3-d]pyrimidine-5-carboxylic acid methyl ester Prepared using the procedure described in example 3 part b) from the product of part b) to give the subtitle compound. δ ¹H$_{CDCl3}$ 1.62-1.64 (6H,m), 3.37 (3H,s), 3.99 (3H,s), 4.60-4.70 (3H,m)

d) 1,2,3,4-Tetrahydro-3-methyl-1-(1-methylethyl)-2,4-dioxo-6-(1H-pyrrolo[2,3-b]pyridin-3-ylmethyl)thieno[2,3-d]pyrimidine-5-carboxylic acid methyl ester Prepared using the procedure described in example 6 part a) from the product of part c) to give the subtitle compound. MS(ESI) 413 [M+H]$^+$ e) 1,2,3,4-Tetrahydro-3-methyl-1-(1-methylethyl)-2,4-dioxo-6-(1H-pyrrolo[2,3-b]pyridin-3-ylmethyl)thieno[2,3-d]pyrimidine-5-carboxylic acid Prepared using the procedure described in example 3 part d) from the product of part d) to give the subtitle compound. MS(ESI) 399 [M+H]$^+$ f) (S) 5-[[4-Hydroxyisoxazolidin-2-yl]carbonyl]-3-methyl-1-(1-methylethyl)-6-(1H-pyrrolo[2,3-b]pyridin-3-ylmethyl)thieno[2,3-d]pyrimidine-2,4(1H,3H)-dione Prepared using the procedure described in example 3 part e) from the product of part e) to give the title compound. MS(APCI) 470 [M+H]$^+$. δ $^1H_{CDCl3}$ 1.36-1.42 (6H,m), 3.17-3.19 (3H,m), 3.32-3.42 (7H,m), 4.60-4.75 (0.5H,m), 4.78-4.82(0.5H,m), 5.50-5.55 (1H,m), 7.00-7.03 (1H,m), 7.43-7.44 (1H,m), 7.95-7.99 (1H,m), 8.19-8.21 (1H,m), 11.54 (1H,s,br)

EXAMPLE 9

(S) 5-[4-Hydroxyisoxazolidin-2-ylcarbonyl]-3-methyl-1-propyl-6-(1H-pyrrolo[2,3-b]pyridin-3-ylmethyl)thieno[2,3-d]pyrimidine-2,4(1H,3H)-dione a) 6-Mercapto-3-methyl-1-propyl-pyrimidine-2,4(1H,3H)-dione A mixture of 6-chloro-3-methyl-1-propyl-pyrimidine-2,4(1H,3H)-dione (3.76 g), sodium hydrosulphide hydrate (6 g) and ethanol (100 ml) was stirred at room temperature for 48 hours then concentrated in vacuo. The residue was dissolved in water (500 ml) and washed with ethyl acetate (2×100 ml). The aqueous phase was acidified with dilute hydrochloric acid, then extracted with ethyl acetate (3×100 ml). The combined organic phase was dried (MgSO$_4$) and evaporated to leave a pale yellow solid which was used directly in the next step.

b) Methyl 1,2,3,4-tetrahydro-3,6-dimethyl-2,4-dioxo-1-propylthieno[2,3-d]pyrimidine-5-carboxylate Prepared from the product of step a) following the procedure of example 3, step a). δ $^1H_{CDCl3}$ 1.00 (3H,t), 1.81 (2H, sextet), 2.46 (3H,s), 3.39 (3H,s), 3.87-3.90 (2H,m), 3.96 (3H,s).

c) 6-(Bromomethyl)-1,2,3,4-tetrahydro-3-methyl-2,4-dioxo-1-propylthieno[2,3-d]pyrimidine-5-carboxylic acid methyl ester Prepared using the procedure described in example 3 part b) from the product of part b) to give the subtitle compound. δ $^1H_{CDCl3}$ 1.02 (3H,t), 1.82 (2H,sextet), 3.39 (3H,s), 3.91 (2H,t), 4.00 (3H,s), 4.68 (2H,s)

d) 1,2,3,4-Tetrahydro-3-methyl-2,4-dioxo-1-propyl-6-(1H-pyrrolo[2,3-b]pyridin-3-ylmethyl)thieno[2,3-d]pyrimidine-5-carboxylic acid methyl ester Prepared using the procedure described in example 6 part a) from the product of part c) to give the subtitle compound. MS(ESI) 413 [M+H]$^+$ e) 1,2,3,4-Tetrahydro-3-methyl-2,4-dioxo-1-propyl-6-(1H-pyrrolo[2,3-b]pyridin-3-ylmethyl)thieno[2,3-d]pyrimidine-5-carboxylic acid Prepared using the procedure described in example 3 part d) from the product of part d) to give the subtitle compound. MS(ESI) 399 [M+H]$^+$ f) (S) 5-[[4-Hydroxyisoxazolidin-2-yl]carbonyl]-3-methyl-1-propyl-6-(1H-pyrrolo[2,3-b]pyridin-3-ylmethyl)thieno[2,3-d]pyrimidine-2,4(1H,3H)-dione Prepared using the procedure described in example 3 part e) from the product of part e) to give the title compound. MS(APCI) 470 [M+H]$^+$. δ $^1H_{CDCl3}$ 0.81-0.85 (3H,m), 1.55-1.63 (2H,m), 3.20-3.21 (3H,m), 3.54-4.23 (8H,m), 4.60-4.70 (0.42H,m), 4.77-4.83 (0.58H,m), 6.99-7.03 (1H,m), 7.41-7.44 (1H,m), 7.93-7.97 (1H,m), 8.19-8.20 (1H,m), 11.53 (!h,s,br)

EXAMPLE 10

(S) 6-[4,5-Dichloro-2-oxo-(2H)-thiazol-3-ylmethyl]-5-[4-hydroxyisoxazolidin-2-ylcarbonyl]-3-methyl-1-(isobutyl)-thieno[2,3-d]pyrimidine-2,4(1H,3H)-dione

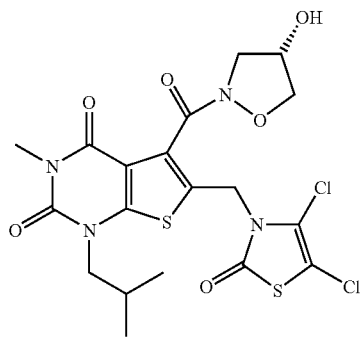

a) 1,2,3,4-Tetrahydro-3,6-dimethyl-1-(isobutyl)-2,4-dioxothieno[2,3-d]pyrimidine-5-carboxylic acid The subtitle compound was prepared by the method of example 3 step d) using the product of example 3 step a). MS(ESI) 297 {M+H]$^+$. δ $^1H_{DMSO}$ 0.93 (6H,d), 2.21 (1H, non), 2.53 (3H,s), 3.27 (3H,s), 3.75 (2H,d), 14.04 (1H,s).

b) (S) 5-[4-Hydroxyisoxazolidin-2-ylcarbonyl]-3,6-dimethyl-1-(isobutyl)thieno[2,3-d]pyrimidine-2,4(1H,3H)-dione The subtitle compound was prepared by the method of example 1 step g) using the product of step a). MS (APCI)

368 {M+H}⁺. δ ¹H$_{CDCl_3}$ 1.00 (6H,m), 2.25-2.37 (1H,m), 2.46 (3H,s), 3.39 (3H,s), 3.53-4.09 (5H,m), 4.61 (1H,d), 4.71 (1H,dt), 5.05 (1H,d).

c) (S) 5-[4-[(1,1-dimethylethyl)dimethylsilyloxy]isoxazolidin-2-ylcarbonyl]-3,6-dimethyl-1-(isobutyl)thieno[2,3-d]pyrimidine-2,4(1H,3H)-dione To a solution of the product of step b) (1.2 g) and imidazole (0.24 g) in dichloromethane (20 ml) was added tert-butyldimethylsilyl chloride (0.54 g). After stirring at ambient temperature for 16 h the mixture was washed with water and the organics poured onto a biotage column. Gradient elution with 0 to 5% methanol in dichloromethane gave the sub-title compound as a colourless solid (1.55 g). δ ¹H$_{CDCl_3}$ 0.09 (3H,s), 0.11 (3H,s), 0.90 (9H,s), 0.99 (6H,d), 2.30 (1H,non), 2.44 (3H,s), 3.36 (3H,s), 3.54 (1H,dd), 3.64 (1H,dd), 3.75 (1H,d), 3.84 (1H,dd), 3.98 (1H,dd), 4.47 (1H,dd), 4.89 (1H,dd).

d) (S) 6-(Bromomethyl)-5-[4-[(1,1-dimethylethyl)dimethylsilyloxy]isoxazolidin-2-ylcarbonyl]-3-methyl-1-(isobutyl)-thieno[2,3-d]pyrimidine-2,4(1H,3H)-dione The subtitle compound was prepared by the method of example 3 step b) using the product of step c). δ ¹H$_{CDCl_3}$ 0.09 (3H,s), 0.12 (3H,s), 0.98 (9H,s), 1.00 (6H,d), 2.31 (1H,non), 3.36 (3H,s), 3.63 (1H,dd), 3.68 (1H,dd), 3.81 (1H,d), 3.87 (1H,dd), 4.00 (1H,dd), 4.37 (1H,dd), 4.64 (1H,d), 4.69 (1H,d), 4.87-4.92 (1H,m).

e) (S) 6-[(4,5-Dichloro-2-oxo-3(2H)-thiazolyl)methyl]-5-[4-[(1,1-dimethylethyl)dimethylsilyloxy]isoxazolidin-2-ylcarbonyl]-3-methyl-1-(isobutyl)-thieno[2,3-d]pyrimidine-2,4(1H,3H)-dione The subtitle compound was prepared by the method of example 3 step c) using the product of step d) and 4,5-dichloro-2-oxo-3(2H)-thiazolone. δ ¹H$_{CDCl_3}$ 0.11 (3H,s), 0.12 (3H,s), 0.91 (9H,s), 0.98 (6H,d), 2.28 (1H,non), 3.36 (3H,s), 3.57 (1H,dd), 3.66 (1H,dd), 3.79 (1H,d), 3.85 (1H,dd), 3.99 (1H,dd), 4.40 (1H,dd), 4.88 (1H,dd), 5.11 (1H,d), 5.20 (1H,d).

f) (S) 6-[(4,5-Dichloro-2-oxo-3(2H)-thiazolyl)methyl]-5-[4-hydroxyisoxazolidin-2-ylcarbonyl]-3-methyl-1-(isobutyl)thieno[2,3-d]pyrimidine-2,4(1H,3H)-dione To a solution of the product of step e) (180 mg) in THF (5 ml) under a nitrogen atmosphere, was added glacial acetic acid (0.10 ml) follwed by 1 N tetrabutylammonium fluoride solution in THF (0.5 ml). After 16 h at ambient temperature the mixture was neutralised with sat sodium bicarbonate solution and extracted into ethyl acetate. The organics were washed with water, and dried over magnesium sulphate. Concentration in vacuo gave a white solid that was purified by reverse phase HPLC to give the title compound as a white solid (100 mg). δ ¹H$_{DMSO}$ 0.92 (6H,d), 2.18 (1H,non), 3.20 (3H,s), 3.43-4.11 (6H,m), 4.60-4.76 (1H,m), 5.04-5.11 (2H, m), 5.51 (1H,s).

EXAMPLE 11

(S) 6-[(3,5-Dimethyl-1H-pyrazol-4-yl)methyl]-5-{4-hydroxyisoxazolidin-2-ylcarbonyl}-1-isobutyl-3-methylthieno[2,3-d]pyrimidine-2,4(1H,3H)-dione

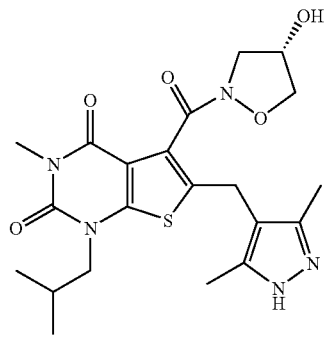

a) 6-[(3,5-Dimethyl-1H-pyrazol-4-yl)methyl]-1-isobutyl-3-methyl-2,4-dioxo-1,2,3,4-tetrahydrothieno[2,3-d]pyrimidine-5-carboxylic acid Potassium carbonate (3.55 g) and dichlorobis(triphenylphosphine)cobalt(II) (0.1 g) were added to a stirred solution of the product of example 3, part a) (1 g) and 2,4-pentanedione (2.64 ml) in dichloromethane (30 ml) under nitrogen. After 48 h, aqueous hydrazine (35%, 2.33 ml) was added and the mixture stirred vigorously for 1 h, diluted with water (30 ml) and extracted with ethyl acetate (2×60 ml). Organic extracts were dried over anhydrous magnesium sulfate, filtered and evaporated under reduced pressure. The residue was purified by column chromatography over silica, eluting with ethyl acetate. The product was dissolved in tetrahydrofuran (20 ml) and methanol (3 ml) then treated with sodium hydroxide solution (1M, 2.57 ml). After 3 days, the mixture was evaporated under reduced pressure to ca. 5 ml, diluted with water (25 ml) and extracted with ethyl acetate (25 ml). The aqueous phase was acidified with hydrochloric acid and extracted with ethyl acetate (3×25 ml). Organic extracts were dried over anhydrous magnesium sulfate, filtered and evaporated under reduced pressure to give the sub-title compound as a solid (0.23 g). MS(ESI) 391 [M+H]⁺. δ ¹H$_{DMSO}$ 0.85 (6H, d), 2.05-2.18 (1H, m), 2.08 (6H, s), 3.17 (3H, s), 3.62 (2H, d), 3.71 (2H, s).

b) (S) 6-[(3,5-Dimethyl-1H-pyrazol-4-yl)methyl]-5-{[4-hydroxyisoxazolidin-2-yl]carbonyl}-1-isobutyl-3-methylthieno[2,3-d]pyrimidine-2,4(1H,3H)-dione Prepared using the procedure described in example 1 part g) from the product of part a) (225 mg) and (S)4-hydroxyisoxazolidine hydrochloride (example 1 part b)) to give the title compound as a solid (98 mg). MS(ESI) 462 [M+H]⁺. δ ¹H$_{DMSO}$ 0.87 (6H, d), 2.05-2.20 (1H, m), 3.19 (2H, s), 3.21 (1H, s), 3.48 (0.67H, d), 3.47-3.85 (6H, m), 3.90-4.05 (0.67H, m), 4.10 (0.67H, dd), 4.57-4.78 (1H, m), 5.51 (1H, d), 12.08 (1H, s, br).

EXAMPLE 12

(S) 5-{4-Hydroxyisoxazolidin-2-ylcarbonyl]-1-(isobutyl)-3-methyl-6-[1,3,5-trimethyl-1-pyrazol-4-ylmethyl]thieno[2,3-d]pyrimidine-2,4(1H,3H)-dione

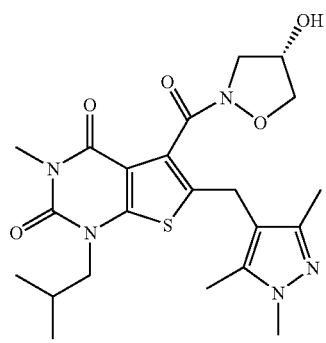

a) (S) 6-(Bromomethyl)-5-{4-hydroxyisoxazolidin-2-ylcarbonyl}-3-methyl-1-(isobutyl)thieno[2,3-d]pyrimidine-2,4(1H,3H)-dione Prepared from the product of example 10 part b) by the method of example 3 part b). δ $^1H_{CDCl3}$ 1.01 (6H, d), 2.27-2.36 (1H, m), 3.39 (3H, s), 3.58 (1H, dd), 3.69-3.76 (2H, m), 3.88 (1H, dd), 4.01 (1H, d), 4.13 (1H, dd), 4.59 (1H, d), 4.60 (1H, d), 4.72 (1H, d), 4.89 (1H, d).

b) (S) 5-{4-Hydroxyisoxazolidin-2-ylcarbonyl}-3-methyl-1-(isobutyl)-6-[(1,3,5-trimethyl-1H-pyrazol-4-yl)methylthieno[2,3-d]pyrimidine-2,4(1H,3H)-dione Potassium tert.-butoxide solution (1M in tetrahydrofuran, 2.99 ml) was added to a stirred solution of the product of part a) (1.00 g) and 2,4-pentanedione (0.31 ml) in tetrahydrofuran (20 ml) at room temperature under nitrogen. After 18 h, 8 ml of this solution was treated with methylhydrazine (64 μl) and after a further 24 h the mixture was evaporated under reduced pressure. The residue was purified by reverse-phase preparative HPLC with gradient aqueous ammonium acetate/acetonitrile elution then by column chromatography over silica, eluting with ethyl acetate/methanol (24:1) to give the title-compound as a solid (24 mg). MS(ESI) 476 [M+H]$^+$. δ $^1H_{DMSO}$ 0.88 (6H, d), 2.02 (3H, s), 2.08-2.18 (4H, m), 3.19 (2H, s), 3.21 (1H, s), 3.47 (0.67H, d), 3.62 (3H, s), 3.55-4.03 (6.67H, m), 4.10 (0.67H, dd), 4.58-4.78 (1H, m), 5.52 (1H, d).

EXAMPLE 13i (R) 6-[(4,5-Dichloro-2-methyl-1H-imidazol-1-yl)methyl]-5-[4-hydroxy-isoxazolidin-2-ylcarbonyl]-3-methyl-1-(isobutyl)thieno[2,3-d]pyrimidine-2,4(1H,3H)-dione The title compound was prepared by the method of Example 1 part g), from the products of example 3 part d) and example 2 part b). MS (APCI) 516/518 [M+H]$^+$. δ $^1H_{CDCl3}$ 0.98 (6H,dd); 2.29 (1H,septet); 2.39 (3H,s); 3.38 (3H,s); 3.54 (1H,dd); 3.66-3.70 (1H,m); 3.80-3.87 (1H,m); 4.04-4.10 (2H,m); 4.56 (1H,d); 4.70-4.75 (1H,m); 4.92 (1H,d); 5.13-5.30 (2H,m).

EXAMPLE 13ii (S) 5-[4-Hydroxyisoxazolidin-2-ylcarbonyl]-3-methyl-6-[(2-methyl-1H-benzimidazol-1-yl)methyl]-1-(isobutyl)thieno[2,3-d]pyrimidine-2,4(1H,3H)-dione

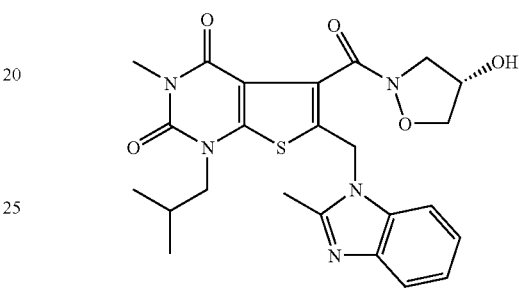

a) 1,2,3,4-Tetrahydro-3-methyl-6-[(2-methyl-1H-benzimidazol-1-yl)methyl]-1-(isobutyl)-2,4-dioxothieno[2,3-d]pyrimidine-5-carboxylic acid, methyl ester Prepared using the procedure described in example 3 part c) from the product of example 3 part b) and 2-methylbenzimidazole. MS(API) 440 [M+H]$^+$. δ $^1H_{CDCl3}$ 0.9 (6H, d), 209-2.12 (1H, m), 2.63 (3H, s), 3.39 (3H, s), 3.62 (2H, d), 4.01 (3H, s), 5.49 (2H, s), 7.23-7.35 (3H, m), 7.7-7.75 (1H, m)

b) 1,2,3,4-Tetrahydro-3-methyl-6-[(2-methyl-1H-benzimidazol-1-yl)methyl]-1-(isobutyl)-2,4-dioxothieno[2,3-d]pyrimidine-5-carboxylic acid Prepared using the procedure described in example 3 part d) from the product of part a) to give the subtitle compound. MS(ESI) 426 [M+H]$^+$ c) (S) 5-[[4-Hydroxyisoxazolidin-2-yl]carbonyl]-3-methyl-6-[(2-methyl-1H-benzimidazol-1-yl)methyl]-1-(isobutyl)thieno[2,3-d]pyrimidine-2,4(1H,3H)-dione Prepared using the procedure described in example 3 part e) from the product of part b) to give the title compound. MS(APCI) 498 [M+H]$^+$. δ $^1H_{CDCl3}$ 0.87-0.93 (6H, m), 2.02-2.17 (1H, m), 2.66 (3H, s), 3.24 (3H, s), 3.38 (3H, s), 3.52-3.58 (2H, m), 3.71-3.8 (1H, m), 4.01-4.07 (2H, m), 4.59 (1H, d), 4.71-4.75 (1H, m), 4.94 (1H, d), 5.3-5.54 (2H, m), 7.22-7.28 (2H, m), 7.39-7.42 (1H, m), 7.69-7.71 (1H, m)

EXAMPLE 13iii (S) 6[(2-Ethyl-1H-benzimidazol-1-yl)methyl]-5-[4-hydroxyisoxazolidin-2-ylcarbonyl]-3-methyl-1-(isobutyl)thieno[2,3-d]pyrimidine-2,4(1H,3H)-dione

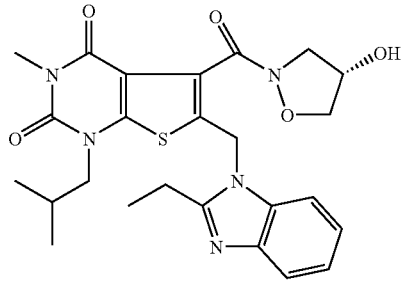

a) 6-[(2-Ethyl-1H-benzimidazol-1-yl)methyl]-1,2,3,4-tetrahydro-3-methyl-1-(isobutyl)-2,4-dioxothieno[2,3-d]pyrimidine-5-carboxylic acid, methyl ester Prepared using the procedure described in example 3 part c) from the product of example 3 part b) and 2-ethylbenzimidazole to give the subtitle compound, which was purified by flash silica chromatography eluting with 30% to 70% ethyl acetate in isohexane. MS(ESI) 455 [M+H]$^+$. δ $^1H_{CDCl3}$ 0.86-0.88 (6H, d), 1.44-1.50 (3H, t), 2-2.1 (1H, m), 2.89-3 (2H, q), 3.39 (3H, s), 3.59-3.62 (2H, d), 4 (3H, s), 5.50 (2H, s), 7.2-7.34 (3H, m), 7.60-7.78 (1H, m)

b) 6-[(2-Ethyl-1H-benzimidazol-1-yl)methyl]-1,2,3,4-tetrahydro-3-methyl-1-(isobutyl)-2,4-dioxothieno[2,3-d]pyrimidine-5-carboxylic acid Prepared using the procedure described in example 3 part d) from the product of part a) to give the subtitle compound. MS(ESI) 441 [M+H]$^+$. δ $^1H_{DMSO}$ 0.79-0.81 (6H, d), 1.30-1.35 (3H, t), 2-2.1 (1H, m), 2.88-2.95 (2H, q), 3.25 (3H, s), 3.58-3.61 (2H, d), 5.80 (2H, s), 7.2-7.23 (2H, m), 7.57-7.63 (2H, m)

c) (S) 6-[(2-Ethyl-1H-benzimidazol-1-yl)methyl]-5-[4-hydroxyisoxazolidin-2-ylcarbonyl]-3-methyl-1-(isobutyl)thieno[2,3-d]pyrimidine-2,4(1H,3H)-dione Prepared using the procedure described in example 3 part e) from the product of part b) to give the title compound after purification by flash silica chromatography eluting with 5% methanol in ethyl acetate followed by a recrystallisation from ethyl acetate/isohexane. MS(APCI) 512 [M+H]$^+$. δ $^1H_{DMSO}$ 0.80-0.83 (6H, m), 1.29-1.34 (3H, t), 2-2.1 (1H, m), 2.88-2.96 (2H, q), 3.20 (3H, s), 3.55-3.71 (3H, m), 3.81-3.91 (2H,m), 4-4.1 (1H, m), 4.55-4.81 (1H, 2m), 5.51-5.57 (3H, m), 7.15-7.20 (2H, m), 7.55-7.58 (1H, m), 7.62-7.65 (1H, m)

EXAMPLE 13iv (S) 5-[4-Hydroxyisoxazolidin-2-ylcarbonyl]-3-methyl-1-(isobutyl)-6-[(2-propyl-1H-benzimidazol-1-yl)methyl]thieno[2,3-d]pyrimidine-2,4(1H,3H)-dione a) 1,2,3,4-Tetrahydro-3-methyl-1-(isobutyl)-2,4-dioxo-6-[(2-propyl-1H-benzimidazol-1-yl)methyl]thieno[2,3-d]pyrimidine-5-carboxylic acid, methyl ester Prepared using the procedure described in example 3 part c) from the product of example 3 part b) and 2-n-propylbenzimidazole to give the subtitle compound after purification by flash silica chromatography eluting with isohexane:ethyl acetate (1:1). MS (APCI) 469 [M+H]. δ $^1H_{DMSO}$ 0.81-0.83 (6H,d), 0.94-0.99 (3H, t), 1.72-1.82 (2H, sextet), 2.01-2.08 (1H, m), 2.80-2.85 (2H,t), 3.19 (3H, s), 3.59-3.61 (2H, d), 3.78 (3H, s), 5.65 (2H, s), 7.15-7.23 (2H, m), 7.53-7.59 (2H, m)

b) 1,2,3,4-Tetrahydro-3-methyl-1-(isobutyl)-2,4-dioxo-6-[(2-propyl-1H-benzimidazol-1-yl)methyl]thieno[2,3-d]pyrimidine-5-carboxylic acid Prepared using the procedure described in example 1 part f) from the product of step a) to give the subtitle compound. MS (APCI) 455 [M+H]. δ $^1H_{DMSO}$ 0.78-0.85 (6H,d), 0.94-1 (3H, t), 1.74-1.86 (2H, sextet), 2-2.07 (1H, m), 2.87-2.92 (2H,t), 3.25 (3H, s), 3.58-3.6 (2H, d), 5.82 (2H, s), 7.21-7.27 (2H, m), 7.58-7.65 (2H, m)

c) (S) 5-[4-Hydroxyisoxazolidin-2-ylcarbonyl]-3-methyl-1-(isobutyl)-6-[(2-propyl-1H-benzimidazol-1-yl)methyl]thieno[2,3-d]pyrimidine-2,4(1H,3H)-dione, Prepared using the procedure described in example 3 part e) from the product of step b) and (S)-4-hydoxyisoxalidine hydrochloride [example 1 part b)] to give the title compound. MS (APCI) 526.2 [M+H]. δ $^1H_{DMSO}$ 0.80-0.84 (6H,m), 0.95-1 (3H, t), 1.76-1.83 (2H, sextet), 2-2.1 (1H, m), 2.86-2.90 (2H,m), 3.2 (3H, s), 3.5-3.61 (3H, m), 3.7-3.92 (2.5H, m), 4.4-4.15 (0.5H, m), 4.5-4.6 (0.4H, m), 4.8 (0.6H, m), 5.52-5.57 (3H, m), 7.16-7.19 (2H, m), 7.55-7.65 (2H,2m)

EXAMPLE 13 v (S) 5-[4-Hydroxyisoxazolidin-2-ylcarbonyl]-3-methyl-1-(isobutyl)-6-[2-(methylthio)-1H-benzimidazol-1-ylmethyl]thieno[2,3-d]pyrimidine-2,4(1H,3H)-dione a) Methyl 1,2,3,4-Tetrahydro-3-methyl-1-(isobutyl)-6-[2-(methylthio)-1H-benzimidazol-1-ylmethyl]-2,4-dioxothieno[2,3-d]pyrimidine-5-carboxylate Prepared using the procedure described in example 3 part c) from the product of example 3 part b) and 2-methylthiobenzimidazole, to give the sub-title compound. MS(APCI) 474 [M+H]$^+$ b) 1,2,3,4-Tetrahydro-3-methyl-1-(isobutyl)-6-[2-(methylthio)-1H-benzimidazol-1-ylmethyl]-2,4-dioxothieno[2,3-d]pyrimidine-5-carboxylic acid Prepared using the procedure described in example 1 part f) from the product of step a), to give the sub-title compound as a white solid. MS(APCI) 459 [M+H]$^+$ c) (S) 5-[4-Hydroxyisoxazolidin-2-ylcarbonyl]-3-methyl-1-(isobutyl)-6-[2-(methylthio)-1H-benzimidazol-1-ylmethyl]thieno[2,3-d]pyrimidine-2,4(1H,3H)-dione Prepared using the procedure described in example 3 part e) from the product of part b) and (S)-4-isoxazolidinol hydrochloride to give the title compound. MS(APCI$^+$) 530 [M+H]$^+$ δ $^1H_{CDCl3}$ 0.87 (3H,s), 0.81 (3H,s), 1.98-2.19 (2H, m), 2.8 (3H,s), 3.21 (3H,m), 3.58-4.17 (6H,m), 4.6-4.8 (1H,m), 5.43-5.58 (2H,m), 7.15-7.19 (2H,m), 7.54-7.6 (2H, m).

EXAMPLE 13 vi (S) 5-[4-Hydroxyisoxazolidin-2-ylcarbonyl]-6-[2-(hydroxymethyl)-1H-benzimidazol-1-ylmethyl]-3-methyl-1-(isobutyl)thieno[2,3-d]pyrimidine-2,4(1H, 3H)-dione

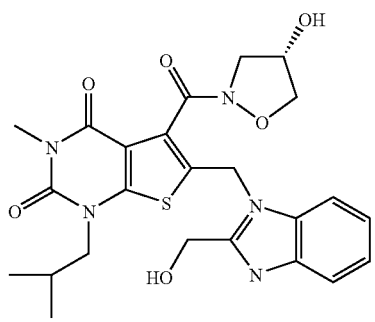

a) 1,2,3,4-Tetrahydro-6-[2-(hydroxymethyl)-1H-benzimidazol-1-ylmethyl]-3-methyl-1-(isobutyl)-2,4-dioxothieno[2,3-d]pyrimidine-5-carboxylic acid, methyl ester The product of example 3 part b) (0.6 g,) was dissolved in DMF (5 ml). 2-Hydroxymethyl-benzimidazole (0.28 g,) and anhydrous potassium carbonate (0.6 g) were added to the solution, which was stirred for 16 h. The sub-title compound was obtained as a white solid after filtration of the reaction mixture and evaporation (0.18 g). MS (APCI) 457 [M+H]$^+$. δ $^1$H$_{CDCl3}$ 0.87 (3H,s), 0.9 (3H,s), 2.1-2.2 (m, 1H), 3.38 (s,3H), 3.57-3.64 (m,3H), 3.96 (s,3H), 4.97 (s,2H), 5.64 (s,2H), 7.26-7.38 (m,2H), 7.22-7.3 (m,1H) and 7.74-7.8 (m,1H).

b) 1,2,3,4-Tetrahydro-6-[2-(hydroxymethyl)-1H-benzimidazol-1-ylmethyl]-3-methyl-1-(isobutyl)-2,4-dioxothieno[2,3-d]pyrimidine-5-carboxylic acid The sub-title compound was prepared using the procedure described in example 3 part d) from the product of part a) to give the sub-title compound. MS (APCI) 443 [M+H]$^+$ c) (S) 5-[4-Hydroxyisoxazolidin-2-ylcarbonyl]-6-[2-(hydroxymethyl)-1H-benzimidazol-1-ylmethyl]-3-methyl-1-(isobutyl)thieno[2,3-d]pyrimidine-2,4(1H, 3H)-dione The title compound was prepared using the procedure described in exampe 3 part e) from the product of example part b). MS (APCI) 474/475 [M+H]$^+$. δ $^1$H$_{DMSO}$ 0.83 (3H,s), 0.85 (3H,s), 2.06-2.18 (1H,m), 3.22 (3H,s), 3.42-3.98 (6H, m), 4.7-4.8 (1H, s(br)), 4.82 (2H,s), 5.25 (1H,s), 5.49 (1H,s), 5.62 (2H,s), 7.16-7.19 (2H,m) and 7.57-7.6 (2H,m).

EXAMPLE 13 vii (S) 5-[4-Hydroxyisoxazolidin-2-ylcarbonyl]-3-methyl-6-[2-(methylamino)-1H-benzimidazol-1-ylmethyl]-1-(isobutyl)thieno[2,3-d]pyrimidine-2,4(1H,3, H)-dione

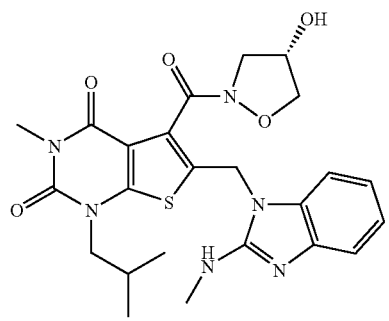

a) 1,2,3,4-Tetrahydro-3-methyl-6-[2-(methylamino)-1H-benzimidazol-1-ylmethyl]-1-(isobutyl)-2,4-dioxo-thieno[2,3-d]pyrimidine-5-carboxylic acid, methyl ester Sodium hydride (0.24 g, 60% in mineral oil) was added portionwise to a stirred solution of 2-(methylamino)benzimidazole (0.93 g) in DMF (50 ml) at 0° C. under nitrogen. After stirring for 30 min at room temperature a solution of the product of example 3 part b) (2.16 g) in DMF (10 ml) was added dropwise and the reaction was stirred for 16 h at room temperature. The solution was poured into water and extracted with ethyl acetate. The combined extracts were dried over magnesium sulfate, filtered and concentrated in vacuo. The residue was recrystallised from ethyl acetate to give the sub-title compound as a white solid, 1.5 g. MS (ESI) 456 [M+H]$^+$. δ $^1$H$_{DMSO}$ 0.83-0.85 (6H,d), 2.05 (1H, m), 2.94-2.95 (3H,d), 3.19 (3H,s), 3.60-3.63 (2H,d), 3.84 (3H,s), 5.39 (2H,s), 6.83-6.87 (2H,m), 6.90-6.99 (1H, t), 7.08-7.11 (1H, d), 7.20-7.22 (1H, d).

b) 1,2,3,4-Tetrahydro-3-methyl-6-[2-(methylamino)-1H-benzimidazol-1-ylmethyl]-1-(isobutyl)-2,4-dioxothieno[2,3-d]pyrimidine-5-carboxylic acid The sub-title compound was prepared following the procedure of example 3 part d) using the product of part a). MS (APCI) 442 [M+H]$^+$ c) (S) 5-[4-Hydroxyisoxazolidin-2-ylcarbonyl]-3-methyl-6-[2-(methylamino)-1H-benzimidazol-1-ylmethyl]-1-(isobutyl)thieno[2,3-d]pyrimidine-2,4 (1H,3H)-dione (S)-4-Hydroxyisoxalidine hydrochloride (Example 1, part b)) (0.08 g) and triethylamine (0.09 ml) were added to a solution of the product of part b) (0.13 g) in dichloromethane (5 ml). 1-Hydroxybenzotriazole (0.09 g) was added as well as 1-ethyl-3-(3'-dimethylaminopropyl)-carbodiimide hydrochloride (0.12 g). The reaction mixture was stirred for 12 h at room temperature. The solution was concentrated under reduced pressure. The residue was purified by flash silica chromatography eluting with a gradient of 0-3% methanol in ethyl acetate. The product obtained was recrystallised from ethyl acetate/isohexane/methanol to give the title compound as a white solid (0.07 g). MS(APCI) 513.2 [M+H]$^+$. δ $^1H_{DMSO}$ 0.82-0.86 (6H,m), 2-2.1 (1H, m), 2.9 (3H, m), 3.2 (3H, s), 3.6-3.68 (3H,m), 3.78-3.84 (1H, m), 3.9-3.94 (1H, m), 4-4.12 (1H, m), 4.6-4.8 (1H, 2m), 5.2-5.61 (3H, m), 6.86-6.99 (3H, m), 7.19-7.27 (2H, m)

EXAMPLE 13 viii (S) 5-[4-Hydroxyisoxazolidin-2-ylcarbonyl]-3-methyl-6-[2-amino-1H-benzimidazol-1-ylmethyl]-1-(isobutyl)thieno[2,3-d]pyrimidine-2,4(1H,3H)-dione

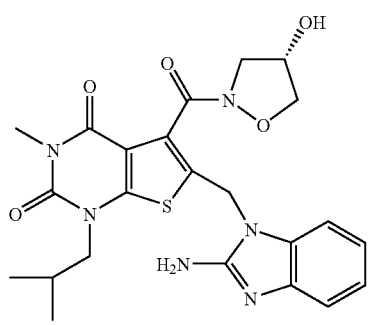

a) 6-[(2-Amino-1H-benzimidazol-1-yl)methyl]-1,2,3,4-tetrahydro-3-methyl-1-(isobutyl)-2,4-dioxothieno[2,3-d]pyrimidine-5-carboxylic acid, methyl ester The sub-title compound was prepared by the method of example 13vii, part a) from the product of example 3 part b) (0.4 g) and 2-aminobezimidazole (0.16 g). MS(ESI) 442 [M+H]$^+$ b) 6-[(2-Amino-1H-benzimidazol-1-yl)methyl]-1,2,3,4-tetrahydro-3-methyl-1-(isobutyl)-2,4-dioxothieno[2,3-d]pyrimidine-5-carboxylic acid The subtitle compound was prepared using the method of example 3 part d) from the product of part a). MS (ESI) 428 [M+H]$^+$ c) (S) 5-[4-Hydroxyisoxazolidin-2-ylcarbonyl]-3-methyl-6-[2-amino-1H-benzimidazol-1-ylmethyl]-1-(isobutyl)thieno[2,3-d]pyrimidine-2,4(1H,3H)-dione The title compound was prepared by the method of example 13vii) part c) from the product of part b). MS(ESI) 499 [M+H]$^+$δ $^1H_{CDCl3}$ 0.93(6H, d), 2.16-2.28 (1H,m), 3.36-3.4 (5H,m), 3.62-4.37 (6H,m), 4.59 (1H,d), 4.78 and 4.9 (1H, t, rotamers), 2.25 (2H, AB q) and 7.16-7.4 (4H,m).

EXAMPLE 13 ix (S)-5-[4-Hydroxy-2-isoxazolidinylcarbonyl]-3-methyl-1-(isobutyl)-6-[(2,4,5-trichloro-1H-imidazol-1-ylmethyl]thieno[2,3-d]pyrimidine-2,4(1H,3H)-dione

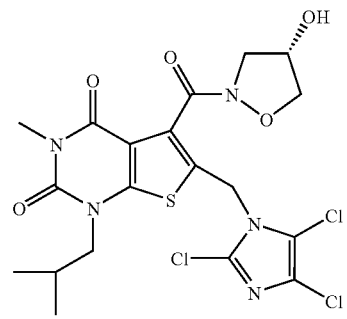

a) Methyl 1,2,3,4-tetrahydro-3-methyl-1-(isobutyl)-2,4-dioxo-6-[2,4,5-trichloro-1H-imidazol-1-ylmethyl]thieno[2,3-d]pyrimidine-5-carboxylate The subtitle compound was prepared by the method of Example 3 part c) using 2,4,5-trichloro-imidazole and the product of Example 3 part b), and purified by chromatography (SiO$_2$/20%-50% ethyl acetate-isohexane). MS (APCI) 479/481/483 [M+H]$^+$. δ $^1H_{CDCl3}$ 0.97 (6H,d), 2.25 (1H, septet), 3.39 (3H,s), 3.74 (2H,d), 3.99 (3H,s), 5.37 (2H,s).

b) 1,2,3,4-Tetrahydro-3-methyl-1-(isobutyl)-2,4-dioxo-6-[2,4,5-trichloro-1H-imidazol-1-ylmethyl]thieno[2,3-d]pyrimidine-5-carboxylic acid The product of part a) (170 mg) was treated with lithium hydroxide monohydrate (31 mg) in water (0.75 ml), methanol (0.75 ml) and THF (2.25 ml) for 4 h at room temperature. The reaction was acidified with glacial acetic acid and evaporated to dryness. The residue was dissolved in water and extracted into dichloromethane. Drying and evaporation gave the subtitle compound (110 mg). MS (APCI) 465/467/469 [M+H]$^+$ c) (S)-5-[4-Hydroxy-2-isoxazolidinylcarbonyl]-3-methyl-1-(isobutyl)-6-[4,5-trichloro-1H-imidazol-1-ylmethyl]thieno[2,3-d]pyrimidine-2,4(1H,3H)-dione The title compound was prepared by the method of Example 1 step g) using the product of step b). MS (APCI) 536/538/540 [M+H]$^+$. δ $^1H_{CDCl3}$ 0.98 (6H,dd); 2.26 (1H, septet); 3.40 (3H,s); 3.47 (1H,dd); 3.66-3.70 (1H,m); 3.80-3.87 (1H,m); 4.04-4.20 (2H,m); 4.55 (1H,d); 4.70-4.75 (1H,m); 4.90 (1H,d); 5.25 (1H,d); 5.40 (1H,d).

EXAMPLE 13x (S) 5-[4-Hydroxyisoxazolidin-2-ylcarbonyl]-3-methyl-1-(isobutyl)-6-[2-thioxo-3(2H)-benzothiazolylmethyl]thieno[2,3-d]pyrimidine-2,4(1H,3,H)-dione

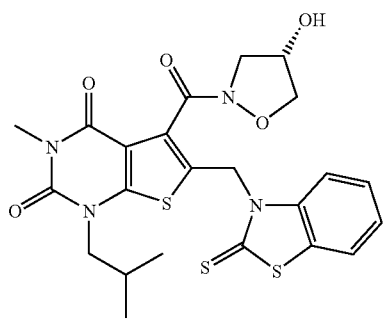

a) Methyl 1,2,3,4-tetrahydro-3-methyl-1-(isobutyl)-2,4-dioxo-6-[2-thioxo-3(2H)-benzothiazolylmethyl]thieno[2,3-d]pyrimidine-5-carboxylate A solution of the product of example 3 step b) (300 mg) and 2-methylthiobenzothiazole (300 mg) in diglyme (3 ml) was heated by microwave irradiation (600 W) to 160° C. After 30 min the solvent was removed by vacuum distillation and the residue purified by gradient chromatography eluting with a gradient of dichloromethane to 5% methanol in dichloromethane to give the sub-title compound as a white solid (150 mg). δ $^1H_{CDCl3}$ 0.93 (6H,d), 2.22 (1H,non), 3.38 (3H,s), 3.71 (2H,d), 4.00 (3H,s), 4.80 (2H,s), 7.33 (1H,dt), 7.45 (1H,dt), 7.77 (1H,dd), 7.92 (1H,d).

b) 1,2,3,4-Tetrahydro-3-methyl-1-(isobutyl)-2,4-dioxo-)-6-[(2-thioxo-3(2H)-benzothiazolyl)methyl]thieno[2,3-d]pyrimidine-5-carboxylic acid The subtitle compound was prepared by the method of example 3, step d) using the product of step a). MS (APCI) 461 {M+H}$^+$. δ $^1H_{DMSO}$ 0.86 (6H,d), 2.10 (1H,non), 3.25 (3H,s), 3.70 (2H,d), 5.00 (2H,s), 7.39 (1H,t), 7.52 (1H,t), 7.93 (1H,d), 8.02 (1H,d).

c) (S) 5-[4-Hydroxyisoxazolidin-2-ylcarbonyl]-3-methyl-1-(isobutyl)-6-[(2-thioxo-3(2H)-benzothiazolyl)methyl]thieno[2,3-d]pyrimidine-2,4(1H,3H)-dione The title compound was prepared using the method of example 3 step e) and the product of step b). MS (APCI) 533 {M+H}$^+$. δ $^1H_{DMSO}$ 0.81-0.88 (6H,m), 2.10 (1H,non), 3.19 (3H,s), 4.14-4.45 (6H,m), 4.65 (1H,s), 4.77 (2H,m), 5.65-5.89 (1H,m), 7.40 (1H,t), 7.51 (1H,t), 7.95 (1H,d), 8.04 (1H,d).

EXAMPLE 13 xi (S) 5-[4-Hydroxyisoxazolidin-2-ylcarbonyl]-3-methyl-1-(isobutyl)-6-[4-chloro-2-oxo-3(2H)-thiazolylmethyl]-thieno[2,3-d]pyrimidine-2,4(1H,3H)-dione

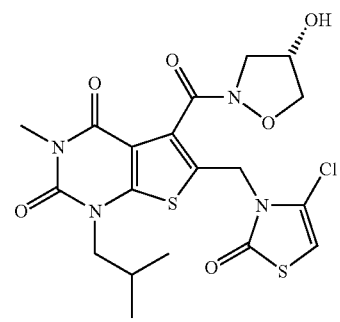

a) 4-Chloro-2-fluorothiazole

A suspension of 2,4-dichlorothiazole (5 g) and potassium fluoride (5 g) in tetramethylenesulfone (20 ml) were heated at 130° C. for 6 h. Further potassium fluoride (5 g) was added and the mixture heated at 175° C. for 16 h. Vacuum distillation of the reaction mixture gave the sub-title compound as a colourless oil (1.7 g). δ $^1H_{CDCl3}$ 6.71 (1H,d).

b) 4-Chloro-2(3H)-thiazolone

A mixture of the product of step a) (1.7 g) and potassium hydroxide (1.22 g) in water (25 ml) and acetonitrile (5 ml) was stirred at ambient temperature for 16 hours. The mixture was partitioned between water and dichloromethane, the aqueous layer was collected, acidified with glacial acetic acid and extracted into dichloromethane. After drying over magnesium sulfate the organics were filtered and concentrated to dryness to give the sub-title compound as a colourless oil (0.35 g). δ $^1H_{CDCl3}$ 5.97 (1H,s), 9.47 (1H,s). MS(ESI) 135/137 {M+H}$^+$ c) Methyl 6-[4-chloro-2-oxo-3(2H)-thiazolylmethyl]-1,2,3,4-tetrahydro-3-methyl-1-(isobutyl)-2,4-dioxo-thieno[2,3-d]pyrimidine-5-carboxylate The subtitle compound was prepared by the method of example 3 part c) using the product of step b). δ $^1H_{CDCl3}$ 0.97 (6H,d), 2.29 (1H,non), 3.39 (3H,s), 3.76 (2H,d), 3.99 (3H,s), 5.17 (2H,s), 6.08 (1H,s).

d) 6-[4-Chloro-2-oxo-3(2H)-thiazolylmethyl]-1,2,3,4-tetrahydro-3-methyl-1-(isobutyl)-2,4-dioxo-thieno[2,3-d]pyrimidine-5-carboxylic acid The subtitle compound was prepared by the method of example 3 part d) using the product of step c).
MS(ESI) 430/432 {M+H}$^+$. δ $^1H_{DMSO}$ 0.90 (6H,d), 2.15 (1H,non), 3.25 (3H,s), 3.73 (2H,d), 5.25 (2H,s), 6.79 (1H,s).

e) (S) 6-[4-Chloro-2-oxo-3(2H)-thiazolylmethyl]-5-[4-hydroxyisoxazolidin-2-ylcarbonyl]-3-methyl-1-(isobutyl)-thieno[2,3-d]pyrimidine-2,4(1H,3H)-dione The title compound was prepared by the method of example 3 part e) using the product of step d). MS (APCI) 501/503 {M+H}+. δ $^1$H$_{DMSO}$ 0.82-0.92 (6H,m), 2.15-2.20 (1H,m), 3.20 (3H,s), 3.40-3.60 (6H,m), 4.60-4.80 (1H,m), 5.04 (2H,s), 5.50 (1H,s), 6.72 (1H,s).

EXAMPLE 13 xii (S)-5-{4-Hydroxyisoxazolidin-2-ylcarbonyl}-3-methyl-1-(isobutyl)-6-[2-oxo-1,3-benzoxazol-3(2H)-ylmethyl]thieno[2,3-d]pyrimidine-2,4(1H,3H)-dione a) Methyl 1,2,3,4-tetrahydro-3-methyl-1-(isobutyl)-2,4-dioxo-6-[(2-oxo-1,3-benzoxazol-3(2H)-yl)methyl]thieno[2,3-d]pyrimidine-5-carboxylate The sub-title compound was prepared by the method of example 3 part c), using product of example 3 part b) and 1,3-benzoxazol-2(3H)-one. δ $^1$H$_{CDCl3}$ 0.95 (6H, d), 2.25 (1H, septet), 3.39 (3H, d), 3.73 (2H, d), 4.04 (3H, s), 5.18 (2H, s), 7.18 (4H, m).

b) Sodium 1,2,3,4-tetrahydro-3-methyl-1-(isobutyl)-2,4-dioxo-6-[2-oxo-1,3-benaoxazol-3(2H)-ylmethyl]-thieno[2,3-d]pyrimidine-5-carboxylate The subtitle compound was prepared by the method of example 3 part d) using the product of part a). MS(ESI) 430.1 (M+ +H)

c) (S) 5-{4-Hydroxyisoxazolidin-2-ylcarbonyl}-3-methyl-1-(isobutyl)-6-[2-oxo-1,3-benzoxazol-3(2H)-ylmethyl]thieno[2,3-d]pyrimidine-2,4(1H,3H)-dione The subtitle compound was prepared by the method of example 3 part e) using the product of part b). δ $^1$H$_{CDCl3}$ 0.89 (6H, d), 2.15 (1H, m), 3.20 (3H, d), 3.81 (6H, m), 4.68 (1H, m), 5.13 (2H, m), 5.50 (1H, m), 7.18 (2H, dd), 7.38 (2H, m). MS (APCI) 501.1 (M+ +H)

EXAMPLE 13 xiii (S)-5-{4-Hydroxyisoxazolidin-2-ylcarbonyl}-3-methyl-1-(isobutyl)-6-[(2-oxo[1,3]thiazolo[5,4-b]pyridin-1(2H)-yl]thieno[2,3-d]pyrimidine-2,4(1H,3H)-dione

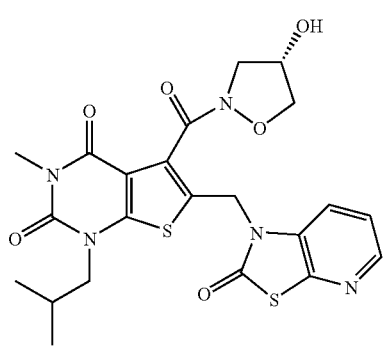

a) 3-Nitropyridine-2-thiol

To a solution of 3-nitro-2-chloropyridine (9.07 g) in ethanol (120 ml) was added NaSH (6.41 g) and the mixture was allowed to stir for 30 min, and then concentrated in vacuo. Water was added to the residue and acidified with dilute HCl and then extracted with ethyl acetate (×5). The organic phase was washed with water, dried and concentrated in vacuo to afford the subtitle compound as an orange solid (9.08 g). δ $^1$H$_{CDCl3}$ 7.19 (dd, J=2.7, 4.2 Hz, 1H); 8.44 (m, 2H). MS(ESI) 154.9.

To a solution of 3-nitro-2-chloropyridine (9.07 g) in ethanol (120 ml) was added NaSH (6.41 g) and the mixture was allowed to stir for 30 mm, and then concentrated in vacuo. Water was added to the residue and acidified with dilute HCl and then extracted with ethyl acetate (×5). The organic phase was washed with water, dried and concentrated in vacuc to afford the subtitle compound as an orange solid (9.08 g). δ$^1$H CDCl3 7.19 (dd. J=2.7, 4.2 Hz, 1H), 8.44 (in, 2H). MS(ESI) 154.9.

c) [1,3]Thiazolo[5,4b]pyridin-2(1H-one

To a solution of the product of part b) (280 mg) in toluene (300 ml) was added 1,1-carbonyldiimidazole (392 mg) and heated to reflux for 16 h. The reaction mixture was concentrated in vacuo and the residue purified by normal phase chromatography eluting with a mixture of iso-hexane:ethyl acetate (3:2). The combined organic fractions were concentrated in vacuo to afford the sub-title compound as an off-white solid (214 mg). δ $^1$H$_{CDCl3}$ 7.23 (dd, J=7.9, 4.9 Hz, 1H); 7.38 (dd, J=8.1, 1.4 Hz, 1H); 8.31 (dd, J=4.9, 1.5 Hz, 1H); 9.50 (s, 1H). MS (ESI) 150.9 [M+H]+ d) Methyl 1,2,3,4-tetrahydro-3-methyl-1-(isobutyl)-2,4-dioxo-6-[(2-oxo[1,3]thiazolo[5,4-b]pyridin-1(2H)-yl)methyl]thieno[2,3-d]pyrimidine-5-carboxylate Prepared using the method of example 3 part c) using the product of example 3 part b) and the product of part c). δ $^1$H$_{CDCl3}$ 0.95 (d, J=6.5 Hz, 6H); 2.25 (septet, J=6.9 Hz, 1H); 3.38 (s, 3H); 3.73 (d, J=7.9 Hz, 2H); 4.04 (s, 3H) 5.30 (dd, J=0.3, 2.6 Hz, 2H); 7.26 (t, J=8.8 Hz, 1H); 7.74 (dd, J=8.4, 1.2 Hz, 1H); 8.31 (dd, J=5.0, 1.3 Hz, 1H). MS (ESI) 460.9 [M+H]+ e) 1,2,3,4-Tetrahydro-3-methyl-1-(isobutyl)-2,4-dioxo-6-[2-oxo[1,3]thiazolo[5,4-b]pyridin-1(2H)-ylmethyl]-thieno[2,3-d]pyrimidine-5-carboxylic acid Prepared using the method of example 3 part d) using the product of part d). δ $^1$H$_{CDCl3}$ 0.96 (q, J=3.3 Hz, 6H); 2.26 (septet, J=7.7 Hz, 1H); 3.51 (s, 3H); 3.81 (d, J=21.1 Hz, 2H); 6.06 (s, 2H) 7.25 (m, 1H); 7.62 (dd, J=8.1, 1.3 Hz, 1H); 8.32 (m, 1H). MS(ESI) 447 [M+H]+ f) (S) 5-{4-Hydroxyisoxazolidin-2-ylcarbonyl}-3-methyl-1-(isobutyl)-6-[2-oxo[1,3]thiazolo[5,4-b]pyridin-1 (2H)-ylmethyl]thieno[2,3-d]pyrimidine-2,4(1H,3H)-dione Prepared using the method of example 3 part e) using the product of part e). δ $^1$H$_{DMSO}$ 0.89 (q, J=6.5 Hz, 6H); 2.15 (septet, J=7.8 Hz, 1H); 3.20 (d, J=4.0 Hz, 3H); 3.76 (m, 6H); 4.68 (m, 1H) 5.26 (m, 1H); 7.41 (dd, J=8.2, 4.9 Hz, 1H); 7.80 (d, J=8.3 Hz, 1H); 8.31 (d, J=4.8 Hz, 1H). MS(APCI) 518.0

EXAMPLE 13 xiv (S)-5-[4-Hydroxyisoxazolidin-2-ylcarbonyl]-3-methyl-1-(isobutyl)-6-(1H-1,2,3-benzotriazol-1-ylmethyl)-thieno[2,3-d]pyrimidine-2,4(1H,3H)-dione a) 6-(1H-1,2,3-Benzotriazol-1-ylmethyl)-1,2,3,4-tetrahydro-3-methyl-1-(isobutyl)-2,4-dioxothieno[2,3-d]pyrimidine-5-carboxylic acid, methyl ester Prepared using the procedure described in example 3 part c) from the product of example 3 part b) and benzotriazole to give the subtitle compound. MS(ESI) 309 [M-benzotriazole]+ δ $^1H_{CDCl3}$ 0.9 (3H,s), 0.98 (3H,s), 2.18-2.24 (1H,m), 2.48 (3H,s), 3.38 (3H,s), 3.62 (2H,d), 4.11 (3H,s), 6.03 (2H,s), 7.41 (1H,t), 7.49 (1H,t), 7.71 (1H,d), and 8.09 (1H,d).

b) 6-(1H-1,2,3-Benzotriazol-1-ylmethyl)-1,2,3,4-tetrahydro-3-methyl-1-(isobutyl)-2,4-dioxo-thieno[2,3-d]pyrimidine-5-carboxylic acid Prepared using the procedure described in example 3 Part d) from the product of part a) to give the subtitle compound. MS(ESI) 414 [M+H]+. δ $^1H_{DMSO}$ 0.87 (3H,s), 0.91 (3H,s), 2.01-2.19 (1H,m), 3.2 (3H,s), 3.7 (2H,d), 6.3 (2H,s), 7.46 (1H,t), 7.6 (1H,t)

c) (S)-5-[4-Hydroxyisoxazolidin-2-ylcarbonyl]-3-methyl-1-(isobutyl)-6-(1H-1,2,3-benzotriazol-1-ylmethyl)-thieno[2,3-d]pyrimidine-2,4(1H,3H)-dione The subtitle compound was prepared using the procedure described in example 1 part g) from the product of part b). MS(ESI) 486 [M+H]+. δ $^1H_{DMSO}$ 0.87 (3H,s), 0.89 (3H,s), 2.01-2.19 (1H,m), 3.08-3.22 (3H,m), 3.62-4.17 (6H,m), 4.62-4.82 (1H,m), 5.6-5.8 (1H,m), 6.07-6.12 (2H,m), 7.42 (1H,t), 7.6 (1H,q), 7.93 (1H,m) and 8.04 (1H,d).

EXAMPLE 13 xv (S)-5-[4-Hydroxyisoxazolidin-2-ylcarbonyl]-3-methyl-1(isobutyl)-6-(1H-pyrrolo[2,3-b]pyridin-1-ylmethyl)thieno[2,3-d]pyrimidine-2,4(1H,3H)-dione

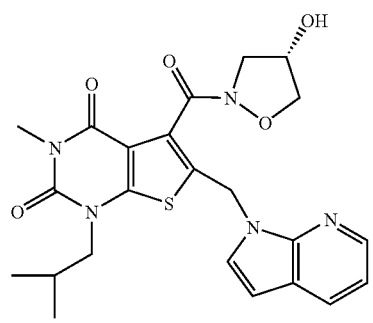

a) 1,2,3,4-Tetrahydro-3-methyl-1-(isobutyl-2,4-dioxo-6-(1H-pyrrolo[2,3-b]pyridin-1-ylmethyl)thieno[2,3-d]pyrimidine-5-carboxylic acid, methyl ester The subtitle compound was prepared using the procedure described in example 3 part c) from the product of example 3 part b) and 7-azaindole. MS (APCI) 427 [M+H]+. δ $^1H_{CDCl3}$ 0.85 (3H,s), 0.92 (3H,s), 2.15-2.25 (1H,m), 3.38 (3H,s), 3.66 (3H,d), 4.03 (3H,s), 4.97 (s,2H), 5.61 (2H,s), 6.49-6.91 (1H,d), 7.06-7.14 (1H,m), 7.38 (1H,d), 7.91 -7.95 (1H,m) and 8.31-8.37 (1H, m).

b) 1,2,3,4-Tetrahydro-3-methyl-1-(isobutyl)-2,4-dioxo-6-(1H-pyrrolo[2,3-b]pyridin-1-ylmethyl)thieno[2,3-d]pyrimidine-5-carboxylic acid The subtitle compound was prepared using the procedure described in example 3 part d) from the product of part a). MS (APCI) 412 [M+H]+ c) (S)-5-[4-Hydroxyisoxazolidin-2-ylcarbonyl]-3-methyl-1-(isobutyl)-6-(1H-pyrrolo[2,3-b]pyridin-1-ylmethyl)thieno[2,3-d]pyrimidine-2,4(1H,3m)-dione The subtitle compound prepared using the procedure described in example 3 part e) from the product of part b). MS(ESI) 484 [M+H]+. δ $^1H_{DMSO}$ 1.82-1.93 (6H,m), 1.16-1.22 (1H,m), 2.02-2.09 (1H,m), 3.20 (3H,s), 3.42-3.98 (4H,m), 4.03-4.18 (1H,m), 4.9-4.81 (1H,m), 5.39-5.61 (3H,m), 6.52 (1H,d), 7.06-7.18 (1H,m), 7.43-7.57 (1H,m), 7.99 (1H, d) and 8.28-8.33 (1H,m).

EXAMPLE 13 xvi (S)-5-[4-Hydroxyisoxazolidin-2-ylcarbonyl]-3-methyl-1-(isobutyl)-6-[(2-methyl-1H-pyrrolo[2,3-b]pyridin-1-ylmethyl]thieno[2,3-d]pyrimidine-2,4(1H,3H)-dione

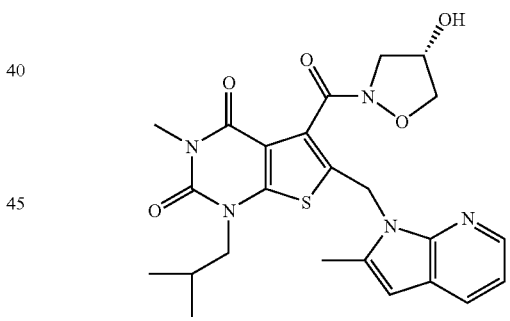

a) 1,2,3,4-Tetrahydro-3-methyl-1-(isobutyl)-6-[2-methyl-1H-pyrrolo[2,3-b]pyridin-1-ylmethyl]-2,4-dioxothieno[2,3-d]pyrimidine-5-carboxylic acid, methyl ester The subtitle compound was prepared using the procedure described in example 3 part c) from the product of example 3 part b) and 2-methyl-7-azaindole. MS (ESI) 441 [M+H]+ δ $^1H_{CDCl3}$ 0.87 (3H,s), 0.90 (3H,s), 2.04-2.21 (1H,m), 2.48 (3H,s), 3.38 (3H,s), 3.62 (2H,d), 3.9 (s,3H), 4.21 (2H,s), 7.01-7.06 (1H,m), 7.76 (1H,d), 8.22 (1H,d), and 8.8 (1H,(br) s).

b) 1,2,3,4-Tetrahydro-3-methyl-1-(isobutyl)-6-[2-methyl-1H-pyrrolo[2,3-b]pyridin-1-ylmethyl]-2,4-dioxo-thieno[2,3-d]pyridine-5-carboxylic acid The subtitle compound was prepared using the procedure described in example 3 part d) from the product of part a). MS (ESI) 427 [M+H]⁺ c) (S) 5-[4-Hydroxyisoxazolidin-2-ylcarbonyl]-3-methyl-1-(isobutyl)-6-[2-methyl-1H-pyrrolo[2,3-b]pyridin-1-ylmethyl]thieno[2,3-d]pyrimidine-2,4(1H,3H)-dione The sub-title compound was prepared using the procedure described in example 3 part e) from the product of part b). MS (ESI) 498 [M+H]⁺. δ $^1H_{CDCl3}$ 0.88 (3H,s), 0.91 (3H,s), 1.2-1.4 (3H,m), 2.13-2.22 (1H,m), 3.38 (3H,s), 3.41-3.59 (2H,m), 3.64-3.8 (1H,m), 4.28-4.4 (4H,m), 4.62-4.8 (2H,m), 5.07-5.18 (1H,m), 6.91-7.04 (1H,m), 7.84 (1H,d), 8.22 (1H, m) and 9.41 (1H,m).

EXAMPLE 13xvii (S)-5-[4-Hydroxyisoxazolidin-2-ylcarbonyl]-3-methyl-1-(isobutyl-6-[5-cyano-(1H)-indol-1-ylmethyl]thieno[2,3-d]pyrimidine-2,4(1H,3H)-dione

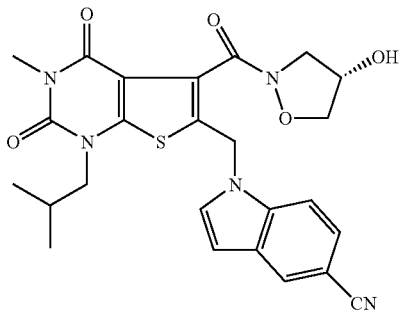

a) 6-[5-Cyano-1H-indol-1-ylmethyl]-1,2,3,4-tetrahydro-3-methyl-1-(isobutyl)-2,4-dioxo-thieno[2,3-d]pyrimidine-5-carboxylic acid, methyl ester Prepared using the procedure described in example 3 part c) from the product of example 3 part b) and 5-cyanoindole to give the subtitle compound, which was purified by flash silica chromatography eluting with 40% ethyl acetate in isohexane. MS(ESI) 451 [M+H]⁺ δ $^1H_{DMSO}$ 0.84-0.86 (6H, d), 2-2.1 (1H,m), 3.2 (3H,s), 3.6-3.63 (2H,d), 4.85 (3H,s), 5.68 (2H,s), 6.67-6.68 (1H,d), 7.53-7.56 (1H,dd), 7.62-7.63 (1H,d), 7.71-7.74 (1H,d), 8.12 (1H,s)

b) 6-[5-Cyano-1H-indol-1-ylmethyl]-1,2,3,4-tetrahydro-3-methyl 1-(isobutyl)-2,4-dioxo-thieno[2,3-d]pyrimidine-5-carboxylic acid Prepared using the procedure described in example 3 part d) from the product of a) to give the subtitle compound. MS(ESI) 437 [M+H]⁺. δ $^1H_{DMSO}$ 0.81-0.83 (6H,d), 2-2.1 (1H,m), 3.19 (3H,s), 3.57-3.59 (2H,d), 5.52 (2H,s), 5.59 -5.6 (1H, d), 7.42-7.45 (1H, d), 7.81-7.82 (1H), 8 (1H, s), 8.15-8.18 (1H, d)

c) (S)-5-[4-hydroxyisoxazolidin-2-ylcarbonyl]-3-methyl-1-(isobutyl)-6-[5-cyano-(1H)-indol-1-ylmethyl]thieno[2,3-d]pyrimidine-2,4(1H,3H)-dione Prepared using the procedure described in example 3 part e) from the product of part b) to give the title compound after purification by flash silica chromatography eluting with 0-2% methanol in ethyl acetate. MS(APCI) 508 [M+H]⁺. δ $^1H_{DMSO}$ 0.82-0.86 (6H,m), 2-2.1 (1H,m), 3.2 (3H,s), 3.58-3.7 (3H,m), 3.8-3.9 (2H, m), 4-4.1 (1H,m), 4.6-4.8 (1H,2m), 5.5-5.6 (3H, m), 6.66-6.67 (1H, d), 7.49-7.53 (1H, m), 7.62-7.65 (1H,m), 7.81-7.84 (1H, d), 8.11 (1H, s)

EXAMPLE 13xviii (S) 5-{4-Hydroxyisoxazolidin-2-ylcarbonyl-3-methyl-1-(isobutyl)-6-[2-oxo-1,3-benzothiazol-3(2H)-ylmethyl]thieno[2,3-d]pyrimidine-2,4(1H,3H)-dione

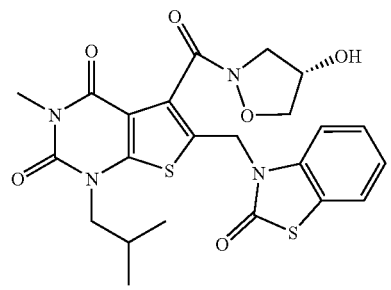

a) Methyl 1,2,3,4-tetrahydro-3-methyl-1-(isobutyl)-2,4-dioxo-6-[2-oxo-3(2H-benzothiazolylmethyl]thieno[2,3-d]pyrimidine-5-carboxylate The subtitle compound was prepared by the method of example 3 step c) using the product of example 3 step b) and benzothiazolone. MS (APCI) 460 [M+H]⁺. δ $^1H_{D6-DMSO}$ 0.88 (6H,d), 2.13 (1H, non), 3.19 (3H,s), 3.67 (2H,d), 3.84 (3H,s), 5.32 (2H,s), 7.23-7.70 (4H,m).

b) 1,2,3,4-Tetrahydro-3-methyl-1-(isobutyl)-2,4-dioxo-6-[2-oxo-3(2H)-benzthiazolylmethyl]thieno[2,3-d]pyrimidine-5-carboxylic acid The subtitle compound was prepared by the method of example 3 step d). using the product of step a). MS (APCI) 468 [M+H]⁺. δ $^1H_{D6-DMSO}$ 0.86 (6H,d), 2.13 (1H, non), 3.19 (3H,s), 3.64 (2H,d), 5.20 (2H,s), 7.18 (1H,dt), 7.28 (1H,dt), 7.63 (1H,dt), 8.18 (1H,d).

c) (S) 5-{4-Hydroxyisoxazolidin-2-ylcarbonyl}-3-methyl-1-(isobutyl)-6-[2-oxo-1,3-benzothiazol-3(2H)-ylmethyl]thieno[2,3-d]pyrimidine-2,4(1H,3H)-dione The title compound was prepared by the method of example 1 step g). using the product of step b). MS(ES⁺) 517 [M+H]⁺. δ $^1H_{D6-DMSO}$ (90° C.) 0.88 (6H,d), 2.11 (1H, non), 3.20 (3H,s), 3.70 (5H,m), 4.09 (1H,dt), 4.58-4.82 (1H,m), 5.21 (2H,m), 5.54 (1H,dd), 7.22 (1H,m), 7.40 (2H,m), 7.69 (1H,d).

EXAMPLE 13 xix (S)-5-[4-Hydroxyisoxazolidin-2-ylcarbonyl]-3-methyl-1-(isobutyl)-6-[2,3-dihydro-6-methyl-3-oxo-pyrazin-2-ylmethyl]-thieno[2,3-d]pyrimidine-2,4 (1H,3H)-dione

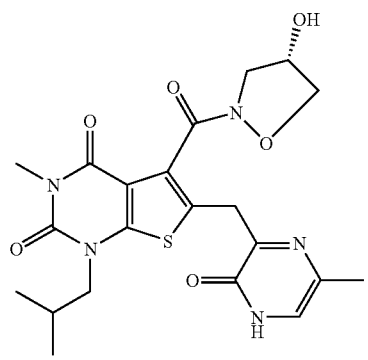

a) Methyl 1,2,3,4-tetrahydro-6-[2,3-dihydro-6-methyl-3-oxo-pyrazin-2-ylmethyl]-3-methyl-1-(isobutyl)-2,4-dioxothieno[2,3-d]pyrimidine-5-carboxylate The subtitle compound was prepared from the product of example 3 part b) and 2,3-dihydro-6-methyl-3-oxo-pyrazine using the method of example 3 part c). The crude product was purified by chromatography (SiO₂/EtOAc). MS (APCI) 419 [M+H]⁺. δ $^1H_{CDCl3}$ 0.97 (6H, d), 2.23-2.33 (1H, m), 2.29 (3H, s), 3.38 (3H, s), 3.75 (2H, d), 4.03 (3H, s), 5.39 (2H, s), 6.85 (1H, d), 7.07 (1H, d).

b) 1,2,3,4-tetrahydro-6-[2,3-dihydro-6-methyl-3-oxo-pyrazin-2-ylmethyl]-3-methyl-1-(isobutyl)-2,4-dioxothieno[2,3-d]pyrimidine-5-carboxylic acid The product of step a) was hydrolysed by the method of example 1 part f). The crude product was dried in vacuo and used without further characterisation.

c) (S)-5-[4-hydroxyisoxazolidin-2-ylcarbonyl]-3-methyl-1-(isobutyl)-6-[2,3-dihydro-6-methyl-3-oxo-pyrazin-2-ylmethyl]-thieno[2,3-d]pyrimidine-2,4 (1H,3H)-dione The crude product of step b) was reacted with (S)-4-hydroxyisoxazolidine hydrochloride using the method of Example 1 part g), to afford the title compound. The crude product was purified by reverse phase HPLC using an elution gradient (75% aqueous ammonium acetate/25% acetonitrile to 100% acetonitrile). MS (APCI) 476 [M+H]⁺. δ $^1H_{CDCl3}$ (spectrum made complex by existence of rotamers) 1.0 (6H, d), 2.3 (3H, s), 2.5 (1H, m), 3.4 (3H, s), 3.5-3.7 (~2H, m), 3.8-4.0 (~2H, m), 4.0-4.2 (~2H, m), 4.6-5.0 (~2H, m), 5.3-5.6 (~2H, dd), 6.9 (1H, m), 7.1 (1H, m).

EXAMPLE 14i (S) 5-[4-Hydroxyisoxazolidin-2-ylcarbonyl]-3-methyl-6-[7-methyl-1H-indol-3-ylmethyl]-1-(isobutyl) thieno[2,3-d]pyrimidine-2,4(1H,3H)-dione a) 1,2,3,4-Tetrahydro-3-methyl-6-[7-methyl-1H-indol-3-ylmethyl]-1-(isobutyl)-2,4-dioxo-thieno[2,3-d]pyrimidine-5-carboxylic acid, methyl ester The subtitle compound was prepared by the method of example 5 part a) using the product of example 3 part b) and 7-methyl indole. MS (APCI) 440 [M+H]⁺. δ $^1H_{CDCl3}$ 0.85-0.89 (6H,d), 2.1-2.2 (1H, m), 2.5 (3H,s), 3.39 (3H, s), 3.62-3.65 (2H, d), 3.98 (3H, s), 4.28 (2H, s), 7.01-7.07 (2H, m), 7.13-7.14 (1H,d), 7.41-7.43 (1H, d), 8 (1H, (br)s)

b) 1,2,3,4-Tetrahydro-3-methyl-6-[7-methyl-1H-indol-3-ylmethyl]-1-(isobutyl)-2,4-dioxothieno[2,3-d]pyrimidine-5-carboxylic acid Prepared using the procedure described in example 1 part c) from the product of step a) to give the subtitle compound. MS (APCI) 426 [M+H]. δ $^1H_{DMSO}$ 0.80-0.83 (6H,d), 2-2.1 (1H, m), 2.44 (3H,s), 3.25 (3H, s), 3.6-3.62 (2H, d), 4.37 (2H, s), 6.84-6.89 (2H, m), 7.27-7.31 (2H, m), 11 (1H,bs), 14 (1H, (br), s)

c) (S) 5-[[4-Hydroxyisoxazolidin-2-yl]carbonyl]-3-methyl-6-[7-methyl-1H-indol-3-ylmethyl]-1-(isobutyl)thieno[2,3-d]pyrimidine-2,4(1H,3H)-dione Prepared using the procedure described in example 1 part g) from the product of step b) and (S)-4-hydroxyisoxazolidine hydrochloride [Example 1 part b] to give the title compound after purification by flash silica chromatography eluting with 0-3% methanol in ethyl acetate and recrystallisation from ethyl acetate:isohexane (9:1). MS (APCI) 497.1 [M+H] δ $^1H_{DMSO}$ 0.81-0.84 (6H,m), 2-2.1 (1H, m), 2.44 (3H, s), 3.2 (3H, s), 3.5-3.9 (6H, 3m), 4.1-4.2 (2H, m), 4.7-4.8 (1H,2m), 5.5 (1H, d), 6.82-6.87 (2H, m), 7.28-7.38 (2H, m), 10.95 (1H, bs)

EXAMPLE 14ii (R) 5-[4-Hydroxyisoxazolidin-2-ylcarbonyl]-3-methyl-6-[2-methyl-1H-indol-3-ylmethyl]-1-(isobutyl) thieno[2,3-d]pyrimidine-2,4(1H,3H)-dione a) Methyl 1,2,3,4-tetrahydro-3-methyl-6-[2-methyl-1H-indol-3-ylmethyl]-1-(isobutyl)-2,4-dioxothieno [2,3-d]pyrimidine-5-carboxylic acid, methyl ester Prepared by the method of example 5 part a) from the product of example 3 part a) and 2-methylindole. MS(ESI) 440 [M+H]⁺. δ $^1H_{CDCl3}$ 0.87 (6H, d), 2.11-2.21 (1H, m), 2.42 (3H, s), 3.38 (3H, s), 3.61 (2H, d), 3.99 (3H, s), 4.22 (2H, s), 7.08 (1H, t), 7.15 (1H, t), 7.31 (1H, d), 7.46 (1H, d), 7.91 (1H, s, br).

b) 1,2,3,4-Tetrahydro-3-methyl-6-[2-methyl-1H-indol-3-ylmethyl]-1-(isobutyl)-2,4-dioxothieno[2,3-d]pyrimidine-5-carboxylic acid Prepared by the method of example 3 part d) from the product of part a). MS(ESI) 426 [M+H]⁺. δ $^1H_{DMSO}$ 0.80 (6H, d), 1.99-2.09 (1H, m), 2.37 (3H, s), 3.18 (3H, s), 3.59

(2H, d), 4.32 (2H, s), 6.91 (1H, t), 7.00 (1H, t), 7.26 (1H, d), 10.96 (1H, s), 14.05 (1H, s, br).

c) (R) 5-[4-Hydroxyisoxazolidin-2-ylcarbonyl]3-methyl-6-[2-methyl-1H-indol-3-ylmethyl]-1-(isobutyl)thieno[2,3-d]pyrimidine-2,4(1H,3H)-dione Prepared by the method of example 3 part d) from the product of part a) and (R)-4-isoxazolidinol hydrochloride [example 2b)]. MS (APCI) 497 [M+H]$^+$. δ $^1$H$_{DMSO}$ 0.80-0.83 (6H, m), 1.98-2.08 (1H, m), 2.37 (1H, s), 3.19 (1.5H, s), 3.21 (1.5H, s), 3.50-3.65 (3H, m), 3.70-3.93 (2H, m), 4.00-4.18 (3H, m), 4.62-4.83 (1H, m), 5.50 (0.5H, d, br), 5.54 (0.5H, d), 6.90 (1H, t), 6.98 (1H, t), 7.25 (1H, d), 7.39 (0.5H, d), 7.43 (0.5H, d), 10.91 (1H, s).

EXAMPLE 14iii (S) 5-[4-Hydroxyisoxazolidin-2-ylcarbonyl]-3-methyl-6-[(2-methyl)-1-pyrrolo[2,3-b]pyridin-3-yl)methyl]-1-propyl-thieno[2,3-d]pyrimidine-2,4(1H,3H)-dione

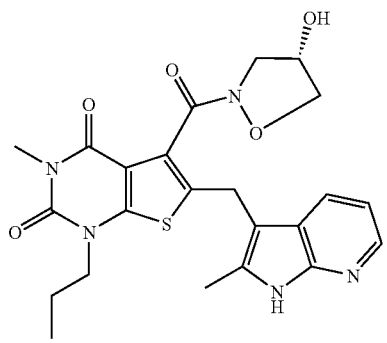

a) Methyl 3-methyl-6-[(2-methyl-1H-pyrrolo[2,3-b]pyridin-3-yl)methyl]2,4-dioxo-1-propyl-1,2,3,4-tetrahydrothieno[2,3-d]pyrimidine-5-carboxylate The subtitle compound was prepared from the product of example 9 part c and 2-methyl-1H-pyrrolo[2,3-b]pyridine using the method of example 6 part b. MS(ESI) 427 [M+H]$^+$ δ $^1$H$_{D6-DMSO}$ 0.82 (6H, t), 1.59 (2H, sextet), 2.38 (3H, s), 3.19 (3H, s), 3.72 (2H, t), 3.83 (3H, s), 4.17 (2H, s), 6.98 (1H, dd), 7.75 (1H, d), 8.10 (1H, dd), 11.48 (1H, s).

b) Sodium 3-methyl-6-[(2-methyl-1H-pyrrolo[2,3-b]pyridin-3-yl)methyl]-2,4-dioxo-1-propyl-1,2,3,4-tetrahydrothieno[2,3-d]pyrimidine-5-carboxylate The subtitle compound was prepared from the product of step a using the method of example 1 part f. MS(ESI) 413 [M+H]$^+$. δ$^1$H$_{D20}$ 0.77 (3H, t), 1.55 (1H, sextet), 2.43 (3H, s), 3.34 (3H, s), 3.63 (2H, t), 4.16 (2H, s), 7.08 (1H, dd), 7.89 (1H, d), 8.06 (1H, d).

c) (S) 5-[4-Hydroxyisoxazolidin-2-ylcarbonyl]-3-methyl-6-[(2-methyl)-1H-pyrrolo[2,3 d]pyridin-3-yl methyl]-1-propyl-thieno[2,3-d]pyrimidine-2,4(1H, 3H)-dione Prepared from the product of part b) and (s)-4-isoxazolidinol hydrochloride [example 1, part b)] following the procedure of example 1, part g) to give the title compound as a solid. MS (APCI) 484 [M+H]$^+$. δ $^1$H$_{D6-DMSO}$ 0.84 (3H, d), 1.64 (2H, d), 2.38 (3H, s), 3.22 (3H, s), 3.41 (1H, d), 3.75 (3H, m), 3.93 (2H, s), 4.10 (2H, m), 4.70 (1H, s), 5.00 (1H, s), 6.91 (1H, s), 7.76 (1H, d), 8.06 (1H, s), 10.92 (1H, s).

EXAMPLE 15i (S)-5-[4-Hydroxyisoxazolidin-2-ylcarbonyl]-3-methyl-6-[2-(methylamino)-3H-imidazo[4,5-b]pyridin-3-ylmethyl]-1-propyl-thieno[2,3-d]pyrimidine-2,4(1H,3H)-dione a) 1,2,3,4-Tetrahydro-3-methyl-6-[2-(methylamino)-3H-imidazo[4,5-b]pyridin-3-ylmethyl]-2,4-dioxo-1-propyl-thieno[2,3-d]pyrimidine-5-carboxylic acid, methyl ester The subtitle compound was prepared by the method of example 13xii) part a) using the product of example 9 part c). MS(ESI) 456 [M+H]$^+$. δ $^1$H$_{DMSO}$ 0.83 (3H,s), 0.85 (3H,s), 2.04-2.11 (1H,m), 2.94 (2H,d), 3.19 (3H,s), 3.6 (2H,d), 3.85 (3H,s), 5.4 (2H,s), 6.83-6.9 (2H,m), 6.97 (1H,t), 7.22 (1H,d).

b) 1,2,3,4-Tetrahydro-3-methyl-6-[2-(methylamino)-3H-imidazo[4,5-b]pyridin-3-ylmethyl]-2,4-dioxo-1-propyl-thieno[2,3-d]pyrimidine-5-carboxylic acid Prepared using the procedure described in exampe 3 part d) from the product of part a) to give the subtitle compound. MS (APCI) 428 [M+H]$^+$ c) (S)-5-[4-Hydroxyisoxazolidin-2-ylcarbonyl]-3-methyl-6-[2-(methylamino)-3H-imidazo[4,5-b]pyridin-3-ylmethyl]-1-propyl-thieno[2,3-d]pyrimidine-2,4(1H,3H)-dione Prepared using the procedure described in exampe 3 part e) from the product of part b) to give the title compound. MS (APCI) 499 [M+H]$^+$. δ $^1$H$_{DMSO}$ 0.81 (3H,m), 0.86 (2H,m), 1.58-1.61 (3H,s), 2.9 (3H,s), 3.2 (3H,s), 3.64-4.2 (6H,m), 5.18 -5.62 (3H,m), 6.88-6.99 (3H,m), 7.2-7.3 (2H,m).

EXAMPLE 15 ii (S)-5-[4-Hydroxy-2-isoxazolidinylcarbonyl]-3-methyl-1-propyl-6-[4,5-Dichloro-2-methyl-1H-imidazol-1-ylmethyl]thieno[2,3-d]pyrimidine-2,4(1H3H)-dione

EXAMPLE 15iii

5-[(4S)-4-Hydroxyisoxazolidin-2-ylcarbonyl]-6-[2-(hydroxymethyl)-1H-benzimidazol-1-ylmethyl]-3-methyl-1-propyl-thieno[2,3-d]pyrimidine-2,4(1,3H)-dione

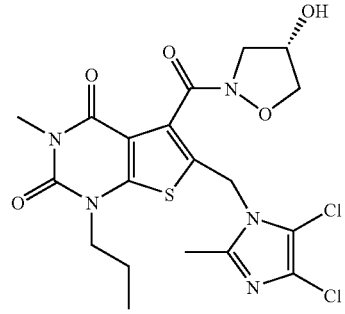

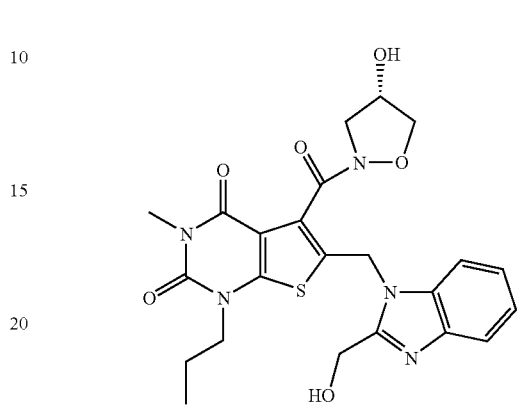

a) 6-[4,5-Dichloro-2-methyl-1H-imidazol-1-ylmethyl]-1,2,3,4-tetrahydro-3-methyl-2,4-dioxo-1-propyl-thieno[2,3-d]pyrimidine-5-carboxylic acid, methyl ester Prepared using the procedure described in example 3 part c) from the product of example 9 part c) to give the subtitle compound. MS (APCI) 445/447 [M+H]$^+$. δ $^1$H$_{CDCl3}$ 0.99 (3H,t), 1.76 (2H,sextet), 2.38 (3H,s), 3.39 (3H,s), 3.85 (2H,td), 3.99 (3H,s), 5.26 (2H,s). Mpt. 155-156° C.

b) 6-[4,5-Dichloro-2-methyl-1H-imidazol-1-ylmethyl]-1,2,3,4-tetrahydro-3-methyl-2,4-dioxo-1-propyl-thieno[2,3-d]pyrimidine-5-carboxylic acid, sodium salt Prepared using the procedure described in example 3 part d) from the product of example part a) to give the sub-title compound. MS (APCI) 431/433 [M+H]$^+$. δ $^1$H$_{DMSO-d6}$ 0.87 (3H,t), 1.67 (2H,sextet), 2.38 (3H,s), 3.19 (3H,s), 3.78 (2H,t), 5.23 (2H,s).

c) (S)—S-[4-hydroxy-2-isoxazolidinylcarbonyl]-3-methyl-propyl-6-[4,5-dichloro-2-methyl-1H-imidazol-1-ylmethyl]-thieno[2,3-d]pyrimidine-2,4(1H,3H)-dione Prepared using the procedure described in exampe 3 part e) from the product of example part b) to give the title compound. MS (APCI) 502/504 [M+H]$^+$. δ $^1$H$_{CDCl3}$ 1.01 (3H,t), 1.79 (2H,sextet), 2.39 (3H,s), 3.35+3.38 (3H,2xs ratio 1:4), 3.47-3.57 (1H,m), 3.81-3.96 (2H,m), 4.01-4.10 (2H,m), 4.57 (1H,d), 4.58-4.75 (1H,m), 4.93 (1H,d), 5.19-5.27 (2H,m).

a) 1,2,3,4-tetrahydro-6-[2-(hydroxymethyl)-1H-benzimidazol-1-ylmethyl]-3-methyl-2,4-dioxo-1-propyl-thieno[2,3-d]pyrimidine-5-carboxylic acid, methyl ester Sodium hydride (60 mg, 60% suspension) was added to 2-benzimidazolemethanol (210 mg) in anhydrous DMF under nitrogen at 0° C. After 10 minutes, product of example 9c (500 mg) in DMF was added dropwise and the reaction mixture was stirred at room temperature for 3 h. Water was added and a precipitate occurred which was filtered, washed with ethyl acetate then ether to give the title-compound as a yellow solid (230 mg). The filtrate was extracted twice with dichloromethane. The organics were dried over magnesium sulfate and concentrated in vacuo to give a brown solid which was combined with the product obtained earlier to give the title-compound as a pale brown solid (480 mg). MS (ES) 443 [M+H]$^+$*δ $^1$H$_{DMSO}$ 0.79-0.84 (3H, t), 1.52-1.62 (2H, q), 3.19 (3H, s), 3.69-3.74 (2H, t), 3.85 (3H, s), 4.77-4.79 (2H, d), 5.71 (2H, s), 5.84-5.88 (1H, t), 7.17-7.26 (2H, m), 7.51-7.54 (1H, d), 7.61-7.63 (1H, d).

b) Sodium 1,2,3,4-tetrahydro-6-[2-(hydroxymethyl)-1H-benzimidazol-1-ylmethyl]-3-methyl-2,4-dioxo-1-propyl-thieno[2,3-d]pyrimidine-5-carboxylate Prepared from product of example 15iii part a) (420 mg) using method of example 1 part f) to give the title-compound as a white solid (260 mg). MS (ES) 429 [M+H]$^+$ c) 5-[(4S)-4-hydroxyisoxazolidin-2-ylcarbonyl]-6-[2-(hydroxymethyl)-1H-benzimidazol-1-yl methyl]-3-methyl-1-propyl-thieno[2,3-d]pyrimidine-2,4(11H,3H)-dione Prepared from product of example 15iii part b) using method of example 13vii part c). The crude material was purified by reverse-phase preparative HPLC eluting from 25% to 95% acetonitrile in 0.1% ammonium acetate aqueous solution to give the title-compound (75 mg). MS (ES) 500.1583 [M+H]$^+$. δ $^1$H$_{DMSO}$ 0.79-0.84 (3H, t), 1.54-1.59

(2H, m), 3.2 (3H, s), 3.6-4.2 (6H, range of m), 4.6-4.8 (3H, 2m), 5.4-5.9 (4H, m), 7.18-7.20 (2H, m), 7.6-7.66 (2H, m).

EXAMPLE 15iv

5-[(4S)-4-Hydroxyisoxazolidin-2-ylcarbonyl]-3-methyl-1-propyl-6[2-amino-1H-benzimidazol-1-ylmethyl]-thieno[2,3-d]pyrimidine-2,4(1H,3H)-dione

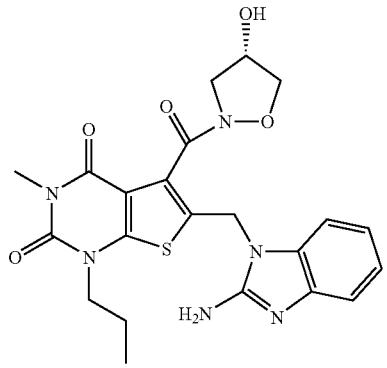

a) 6-[2-amino-1H-benzimidazol-1-ylmethyl]-1,2,3,4-tetrahydro-3-methyl-2,4-dioxo-1-propyl-thieno[2,3-d]pyrimidine-5-carboxylic acid, methyl ester Sodium hydride (60 mg, 60% suspension) was added to 2-aminobenzimidazole (200 mg) in anhydrous DMF under Nitrogen. After 10 min, product of example 9c (500 mg) in dry DMF was added dropwise and the reaction mixture was stirred at room temperature for 3 h. Water was added and a precipitate occurred which was filtered, washed with ethyl acetate then ether to give the title-compound as brown-orange crystals (220 mg). MS (ES) 428 [M+H]$^+$. δ $^1$H$_{DMSO}$ 0.81-0.86 (3H, t), 1.54-1.66 (2H, q), 3.19 (3H, s), 3.72-3.76 (2H, t), 3.88 (3H, s), 5.4 (2H, s), 6.6 (2H, s), 6.84-6.89 (1H, t), 6.93-6.98 (1H, t), 7-7.15 (2H, m).

b) 6-[2-amino-1H-benzimidazol-1-ylmethyl]-1,2,3,4-tetrahydro-3-methyl-2,4-dioxo-1-propyl-thieno[2,3-d]pyrimidine-5-carboxylic acid Prepared from product of example 15iv part a) (220 mg) by the method of example 1 part f) to give the title-compound as a pale yellow solid (190 mg). MS (ES) 414 [M+H]$^+$ c) 5-F(4S)-4-hydroxyisoxazolidin-2-ylcarbonyl]-3-methyl-1-propyl-6-[2-amino-1H-benzimidazol-1-ylmethyl]-thieno[2,3-d]pyrimidine-2,4(1H,3H)-dione Prepared from the product of example 15iv part b) (190 mg) by the method of example 13vii part c). The crude material was purified by reverse-phase preparative HPLC eluting from 5% to 95% acetonitrile in 0.1% ammonium acetate aqueous, followed by trituration and filtation with methanol to give the title-compound as a white solid (19 mg). MS (ES) 485.1631 [M+H]$^+$δ $^1$H$_{DMSO}$ 0.82-0.86 (3H, t), 1.57-1.62 (2H, q), 3.19 (3H, s), 3.65-4.15 (6H, range of m), 4.65-4.80 (1H, m), 5.26-5.60 (3H, m), 6.63-6.69 (2H, bm), 6.84-6.87 (1H, t), 6.93-6.97 (1H, t), 7.12-7.14 (1H, d), 7.20-7.27 (1H, 2d).

EXAMPLE 16 i)

(S) 5-[4-Hydroxyisoxazolidin-2-ylcarbonyl]-3-methyl-6-[2-(methylamino)-1H-benzimidazol-1-ylmethyl]-1-(isopropyl)thieno [23-d]pyrimidine-2,4(1H,3H)-dione

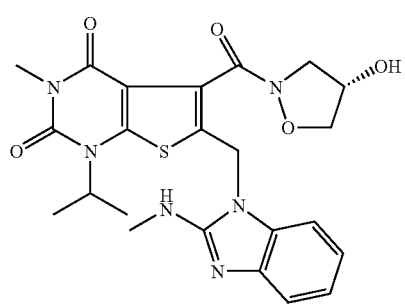

a) 1,2,3,4-Tetrahydro-3-methyl-6-[2-(methylamino)-1H-benzimidazol-1-ylmethyl]-1-(isopropyl)-2,4-dioxothieno[2,3-d]pyrimidine-5-carboxylic acid, methyl ester Prepared using the procedure described in example 13 vii) part a) from the product of example 8 part c) and 2-methylaminobenzimidazole to give the sub-title compound after trituration with ethyl acetate followed by filtration. MS(ESI) 442 [M+H]$^+$. δ $^1$H$_{DMSO}$ 1.40-1.42 (6H,d), 2.94-2.96 (3H,d), 3.16 (3H,s), 3.85 (3H,s), 4.3 (1H, bs), 5.39 (2H,s), 6.84-6.99 (3H,m), 7.11-7.14 (1H, d), 7.20-7.22 (1H, d)

b) 1,2,3,4-Tetrahydro-3-methyl-6-[2-(methylamino)-1H-benzimidazol-1-ylmethyl]-1-(isopropyl)-2,4-dioxothieno[2,3-d]pyrimidine-5-carboxylic acid Prepared using the procedure described in example 3 part d) from the product of part a) to give the subtitle compound. MS(ESI) 428 [M+H]$^+$ c) (S) 5-[4-Hydroxyisoxazolidin-2-ylcarbonyl]-3-methyl-6-[2-(methylamino)-1H-benzimidazol-1-ylmethyl]-1-(isopropyl)thieno[2,3-d]pyrimidine-2,4(1H,3H)-dione Prepared using the procedure described in example 13 vii) part c) from the product of part b) to give the subtitle compound after purification by flash silica chromatography eluting with 0-3% methanol in dichloromethane followed by trituration with ether. MS(APCI) 499 [M+H]$^+$δ $^1$H$_{DMSO}$ 1.41-1.42 (6H, m), 2.94-2.95 (3H, d), 3.17 (3H, s), 3.55-3.66 (1H, 2d), 3.81-3.84 (1H, m), 3.89-4 (1H, m), 4-4.1 (1H,m), 4.1-4.2 (1H, m), 4.6-4.75 (1H, 2m), 5.17-5.26 (1H, m), 5.37-5.44 (1H, 2m), 5.52-5.61 (1H, 2m), 6.89-6.99 (3,H, m), 7.19-7.30 (2H, m)

EXAMPLE 16 ii (S)-5-[4-Hydroxy-2-isoxazolidinylcarbonyl]-6-[4,5-dichloro-2-methyl-1H-imidazol-1-ylmethyl-3-methyl-1-(isopropyl)thieno[2,3-d]pyrimidine-5-carboxamide

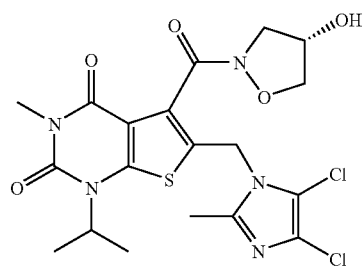

a) 6-[4,5-Dichloro-2-methyl-1H-imidazol-1-ylmethyl]-1,2,3,4-tetrahydro-3-methyl-1-(isopropyl)-2,4-dioxothieno[2,3-d]pyrimidine-5-carboxylic acid, methyl ester Prepared using the procedure described in example 3 part c) from the product of example 8 part c) to give the subtitle compound. MS (APCI) 445/446 [M+H]$^+$. δ $^1$H$_{CDCl3}$ 1.56-1.61 (6H,m), 2.37-2.38 (3H,m), 3.37 (3H,s), 3.98 (3H,s), 4.40-4.50 (1H,br.s), 5.25 (2H,s).

b) 6-[4,5-Dichloro-2-methyl-1H-imidazol-1-ylmethyl]-1,2,3,4-tetrahydro-3-methyl-1-(isopropyl)-2,4-dioxothieno[2,3-d]pyrimidine-5-carboxylic acid, sodium salt Prepared using the procedure described in example 3 part d) from the product of example part a) to give the sub-title compound. MS (APCI) 431/433 [M+H]$^+$. δ $^1$H$_{D2O}$ 1.53 (6H,d), 2.39 (3H,s), 3.31 (3H,s), 3.54-3.69 (1H,m), 5.32 (2H,s).

c) (S)-5-[4 hydroxy-2-isoxazolidinylcarbonyl]-6-[4,5-Dichloro-2-methyl-1H-imidazol-1-ylmethyl-3-methyl-1-(isoropyl)thieno[2,3-d]pyrimidine-5-carboxamide Prepared using the procedure described in example 3 part e) from the product of part b) to give the title compound. MS(APCI) 502/504 [M+H]. δ $^1$H$_{CDCl3}$ 1.55-1.61 (6H,m), 2.39 (3H,s), 3.33 (3H,s), 3.51 (1H,dd), 4.01-4.09 (2H,m), 4.40-4.55 (1H,br.s), 4.57 (1H,d); 4.68-4.75 (1H,m); 4.95 (1H,d); 5.15-5.28 (2H,m).

EXAMPLE 16iii (S)-5-[4-Hydroxyisoxazolidin-2-ylcarbonyl]-6-[2-(hydroxymethyl)-1H-benzimidazol-1-yl methyl]-3-methyl-1-(isopropyl)thieno[2,3-d]pyrimidine-2,4(1H,3H)-dione

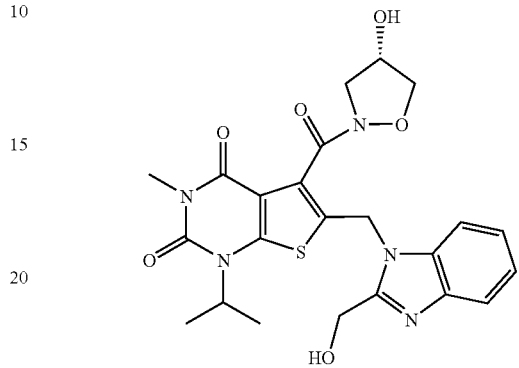

a) 1,2,3,4-tetrahydro-6-[2-(hydroxymethyl)-1H-benzimidazol-1-ylmethyl]-3-methyl-1-(isopropyl)-2,4-dioxo-thieno[2,3-d]pyrimidine-5-carboxylic acid, methyl ester Sodium hydride (79 mg, 60% suspension) was added to 2-benzimidazolemethanol (280 mg) in anhydrous DMF under Nitrogen at 0° C. After 10 min, product of example 8b (660 mg) in DMF was added dropwise and the reaction mixture was stirred at room temperature for 3 h. Water was added and a precipitate occurred which was filtered, washed with ethyl acetate then ether to give the title-compound as an off-white solid (350 mg). MS (ES) 443 [M+H]$^+$δ $^1$H$_{DMSO}$ 1.39-1.41 (6H, d), 3.18 (3H, s), 3.85 (3H, s), 4.32 (1H, bs), 4.78-4.80 (2H, s), 5.71 (2H, s), 5.86 (1H, bs), 7.23 (2H, m), 7.55-7.57 (1H, d), 7.61-7.64 (1H, d).

b) Sodium 1,2,3,4-tetrahydro-6-[2-hydroxymethyl)-1H-benzimidazol-1-ylmethyl]-3-methyl-1-(isopropyl)-2,4-dioxo-thieno[2,3-d]pyrimidine-5-carboxylate Prepared from product of example 16iii part a) (350 mg) using the method of example 1 part f) to give the title-compound as a white solid (340 mg). MS (ES) 429 [M+H]$^+$ c) (S)-5-[4-hydroxyisoxazolidin-2-ylcarbonyl]-6-[2-hydroxymethyl)-1H-benzimidazol-1-yl methyl]-3-methyl-1-(isopropyl)-thieno[2,3-d]pyrimidine-2,4(1H,3H)-dione Prepared from product of example 16iii part b) using the method of example 13vii part c). The crude material was purified by reverse-phase preparative HPLC eluting from 25% to 95% acetonitrile in 0.1% ammonium acetate aqueous solution to give the title-compound (110 mg). MS (ES) 500.1610 [M+H]$^+$. δ $^1$H$_{DMSO}$ 1.37-1.40 (6H, m), 3.18 (3H, s), 3.5-4.4 (5H, range of m), 4.6-4.8 (3H, 2m), 5.5-6.9 (4H, m), 7.17-7.21 (2H, m), 7.59-7.68 (2H, m).

EXAMPLE 16iv (S)-5-[4-Hydroxyisoxazolidin-2-ylcarbonyl]-3-methyl-1-(isopropyl)-6-[2-amino-1H-benzimidazol-1-ylmethyl]thieno[2,3-d]pyrimidine-2,4(1H,3H)-dione

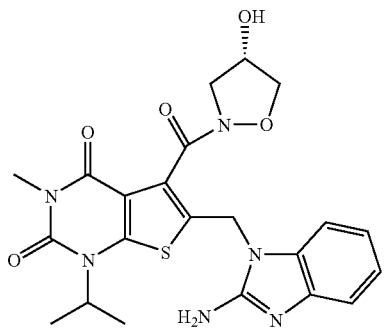

a) 6-[2-amino-1H-benzimidazol-1-ylmethyl-1,2,3,4-tetrahydro-3-methyl-1-(isopropyl)-2,4dioxo-thieno[2,3-d]pyrimidine-5-carboxylic acid, methyl ester Prepared from the product of example 8b (660 mg) and 2-aminobenzimidazole (250 mg) by the method of example 13vii part a). The crude material was purified by flash silica chromatography eluting with 50% ethyl acetate in isohexane then 4% methanol in dichloromethane containing 0.1% triethylamine to give the title-compound as a yellow foam (360 mg). MS (ES) 428 [M+H]$^+$. δ $^1$H$_{DMSO}$ 1.40-1.42 (6H, d), 3.17 (3H, s), 3.88 (3H, s), 4.3 (1H, bs), 5.42 (2H, s), 6.62 (2H, s), 6.87-6.90 (1H, t), 6.93-6.98 (1H, t), 7.11-7.15 (2H, m).

b) Sodium 6-[2-amino-1H-benzimidazol-1-yl-methyl]-1,2,3,4-tetrahydro-3-methyl-1-(isopropyl)-2,4-dioxo-thieno[2,3-d]pyrimidine-5-carboxylate Prepared from the product of example 16iv part a) (360 mg) by the method of example 1 part f) to give the title-compound as a white solid (190 mg). MS (ES) 414 [M+H]$^+$ c) (S)-5-[4-hydroxyisoxazolidin-2-ylcarbonyl]-3-methyl-1-(isopropyl)-6-[2-amino-1H-benzimidazol-1-ylmethyl]-thieno[2,3-d]pyrimidine-2,4(1H,3H)-dione Prepared from the product of example 16iv part b) (190 mg) by the method of example 13vii part c). The crude material was purified by reverse-phase preparative HPLC eluting from 25% to 95% acetonitrile in 0.1% ammonium acetate aqueous, followed by trituration with methanol and filtration to give the title-compound as a white solid (20 mg). MS (ES) 485.1623 [M+H]$^+$. δ $^1$H$_{DMSO}$ 1.35-1.42 (6H, m), 3.18 (3H, m), 3.6-4.4 (5H, range of m), 4.6-4.8 (1H, m), 5.2-5.6 (3H, m), 6.7-6.8 (2H, bs), 6.86-6.90 (1H, t), 6.95-6.98 (1H, t), 7.13-7.15 (1H, d), 7.2-7.3 (1H, 2d).

EXAMPLE 16 v (S)-5-[4-Hydroxyisoxazolidin-2-ylcarbonyl-3-methyl-1-(isopropyl)-6-[2-methyl-1H-pyrrolo[2,3-b]pyridin-1-ylmethyl]thieno[2,3-d]pyrimidine-2,4(1H,31)-dione

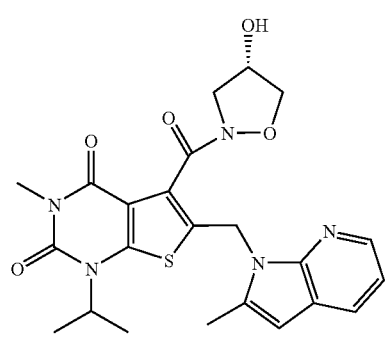

a) 1,2,3,4-Tetrahydro-3-methyl-1-(isopropyl)-6-[2-methyl-1H-pyrrolo[2,3-b]pyridin-1-yl methyl]-2,4-dioxothieno[2,3-d]pyrimidine-5-carboxylic acid To a stirred suspension of 60% sodium hydride (0.15 g) in THF (5 ml) was added a solution of 2-methylazaindole (0.25 g) in THF (5 ml) dropwise under nitrogen at ambient temperature. After stirring for 5 min. it was cooled to 0° C. a solution of the product of example 22, part a) (0.60 g) in THF (10 ml) was added and the mixture warmed to room temperature and stirred for 5 h. It was quenched with water, acidified with 2.5M HCl and extracted with dichloromethane, the organic extracts were dried over anhydrous magnesium sulfate, filtered and evaporated under reduced pressure. The residue was purified by column chromatography over silica, eluting with ethyl acetate/1-hexane (1:1) followed by ethyl acetate/methanol (9:1) to give the sub-title compound as a solid (0.06 g). MS (ESI) 413 [M+H]$^+$. δ $^1$H$_{DMSO}$ 1.36 (6H, d), 3.17 (3H, s), 4.20 (1H, s, br), 5.73 (2H, s), 6.32 (1H, s), 7.09-7.12 (1H, s), 7.88-7.90 (1H, m), 8.20-8.21 (1H, m)

b) (S)-5-[4-Hydroxyisoxazolidin-2-ylcarbonyl]-3-methyl-1-(isopropyl)-6-[2-methyl-1H-pyrrolo[2,3-b]pyridin-1-ylmethyl]thieno[2,3-d]pyrimidine-2,4(1H, 3H)-dione Prepared from the product of part a) and (S)-4-isoxazolidinol hydrochloride [example 1, part b)] following the procedure of example 1, part g) to give the title compound as a solid. MS(APCI) 484 [M+H]$^+$. δ $^1$H$_{DMSO}$ 1.38-1.40 (6H, m), 2.41 (3H, m), 3.16-3.19 (3H, m), 3.54-4.25 (5H, m), 4.60 4.73 (1H, m), 5.42-5.58 (3H, m), 6.29 (1H, s), 7.09-7.13 (1H, m), 7.88 (1H, dd), 8.22-8.26 (1H, m)

EXAMPLE 17i (S)-5-[4-Hydroxyisoxazolidin-2-ylcarbonyl]-3-methyl-1-(isobutyl)-6-[3,5-diethyl-1H-pyrazol-4-ylmethyl]thieno[2,3-d]pyrimidine-2,4(1H,3H)-dione

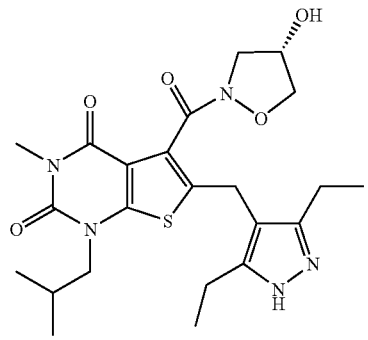

a) 6-[3,5-Diethyl-1H-pyrazol-4-ylmethyl]-3-methyl-1-(isobutyl)-2,4-dioxo-1,2,3,4-tetrahydrothieno[2,3-d]pyrimidine-5-carboxylic acid Prepared using the procedure described in example 12 part a) from the product of example 3 part c) (1 g) and 3,5-heptanedione to give the subtitle compound as a solid (0.37 g). MS(ESI) 419 [M+H]+. δ $^1H_{DMSO}$ 0.86 (6H, d), 1.10 (6H, t), 2.05-2.15 (1H, m), 2.49 (4H, q), 3.26 (3H, s), 3.66 (2H, d), 4.06 (2H, s).

b) (S) 5-[4-hydroxyisoxazolidin-2-ylcarbonyl]-3-methyl-1-(isobutyl)-6-[3,5-diethyl-1H-pyrazol-4-ylmethyl]thieno[2,3-d]pyrimidine-2,4(1H,3H)-dione Prepared using the procedure described in example example 3 part e) from the product of part a) and (S)-4-hydroxyisoxazolidine hydrochloride {example 1, part b)} to give the title compound as a solid (145 mg). MS(ESI) 490 [M+H]+. δ $^1H_{DMSO}$ 0.86 (6H, d), 1.09 (6H, t), 2.03-2.19 (1H, m), 2.49-2.52 (4H, m), 3.19 (2H, s), 3.21 (1H, s), 3.50 (0.67H, d), 3.35-3.63 (1H, m), 3.70 (1H, dd), 3.75-3.80 (3H, m), 3.84 (0.67H, dd), 3.90-4.05 (1H, m), 4.09 (0.67H, dd), 4.58-4.80 (1H, m), 5.51 (1H, d), 12.18 (1H, s, br).

EXAMPLE 17 ii (S) 5-[4-Hydroxyisoxazolidin-2-ylcarbonyl-3-methyl-1-(isobutyl)-6-[3-(1,1-dimethylethyl)-5-methyl-1H-pyrazol-4-ylmethyl]thieno[2,3-d]pyrimidine-2,4(1H,3H)-dione

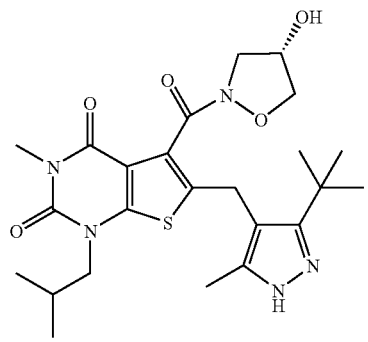

Prepared using the procedure described in example 12 part b) from the product of example 12 part a), 5,5-dimethylhexane-2,4-dione and 35% aqueous hydrazine solution to give the title compound as a solid. MS(ESI) 504 [M+H]+. δ $^1H_{DMSO}$ 0.85 (6H, d), 1.23 (9H, s), 1.99-2.06 (4H, m), 3.19 (2.25H, s), 3.21 (0.7525H, s), 3.50-3.60 (2H, m), 3.64-3.72 (1H, m) 3.79 (1H, m), 3.83-3.96 (3H, m), 3.98-4.05 (0.25H, m), 4.07 (0.75H, dd), 4.58-4.78 (1H, m), 5.51 (1H, d), 12.08 (1H, s, br).

EXAMPLE 18i (S) 5-14-Hydroxyisoxazolidin-2-ylcarbonyl]-3-methyl-1-(isobutyl)-6-[2-methyl-4-quinolinylmethyl]thieno[2,3-d]pyrimidine-2,4(1H,3H)-dione

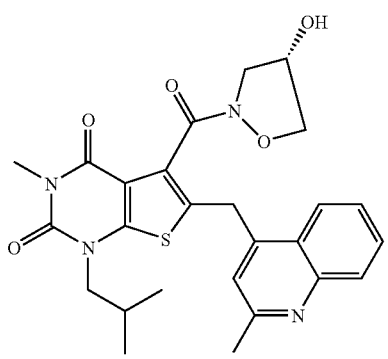

a) N-Methoxy-N,2-dimethyl-4-quinolinecarboxamide

To a solution of 2-methyl-4-quinolinecarboxylic acid (8.2 g) in dichloromethane (100 ml) containing DMF (1 drop) was added oxalyl chloride (4.5 ml). This mixture was heated at reflux for 1 h. After concentrating to dryness in vacuo the residue was redissolved in dichloromethane (50 ml), triethylamine (17 ml) was added followed by N,O-dimethylhydroxylamine (8.2 g) and the reaction was stirred at ambient temperature for 16 h. The reaction mixture was washed with water (2×100 ml), the organic solution was evaporated and the residue was purified by chromatography eluting with ethyl acetate to give the subtitle compound as a brown oil (10 g). MS (ESI) 231 μM+H]+. δ $^1H_{CDCl3}$ 2.77 (3H,s), 3.24/3.40 (3H, s), 3.47/3.74 (3H, s), 7.26 (1H,s), 7.52 (1H,t), 7.71 (1H,t), 7.80 (1H,d), 8.06 (1H,d).

b) 2-Methyl-4-quinolinecarboxaldehyde

A solution of 2.5N diisobutylaluminium hydride in toluene (5.6 ml) was added to a solution of the product of step a) (1.6 g) in anhydrous toluene (40 ml) at −78° C. After 2 h the reaction was quenched by the addition of sodium potassium tartrate (5 g) in water (25 ml) and allowed to warm to room temperature. The organic phase was collected, washed with water, dried over magnesium sulfate and concentrated to dryness in vacuo. The residue was the purified by chromatography eluting with 30% ethyl acetate in i-hexane to give the subtitle compound (0.82 g). δ $^1H_{CDCl3}$ 2.87 (3H,s), 7.26 (1H,s), 7.67 (1H,ddd), 7.69 (1H,s), 7.78 (1H,ddd), 8.12 (1H,d), 8.96 (1H,d), 10.49 (1H,s).

c) 1,1-Dimethylethyl 1,2,3,4-tetrahydro-3-methyl-1-(isobutyl)-2,4-dioxothieno[2,3-d]pyrimidine-5-carboxylate To a solution of the product of example 1 part c) (2.0 g) in dichloromethane (12 ml) containing DMF (1 drop) was added oxalyl chloride (1.0 ml). This mixture was stirred at room temperature for 1 h. After concentrating to dryness in vacuo the residue was redissolved in dichloromethane (8 ml), triethylamine (4 ml) was added followed by 2-methyl-propan-2-ol (8.0 ml) and the reaction stirred at ambient temperature for 4 h. The reaction mixture was washed with water (2×100 ml), the organic phase was dried and evaporated and the residue was purified by chromatography eluting with i-hexane/ethyl acetate (5:1) to give the subtitle compound as an orange oil (1.6 g). δ $^1H_{CDCl3}$ 0.99 (6H,d), 1.61 (9H,s), 2.31 (1H,non), 3.42 (3H,s), 3.80 (2H,d), 7.26 (1H,s).

d) 1,1-Dimethylethyl 1,2,3,4-tetrahydro-6-[hydroxy(2-methyl-4-quinolinyl)methyl-3-methyl-1-(isobutyl)-2,4-dioxothieno[2,3-d]pyrimidine-5-carboxylate The subtitle compound was prepared by the method of example 1 step d) using the products of step c) and step b). MS(ESI) 510 {M+H}$^+$. δ $^1H_{CDCl3}$ 0.85 (6H,d), 1.66 (9H,s), 2.11 (1H,m), 2.82 (3H,s), 3.39 (3H,s), 3.48 (1H,dd), 3.53 (1H,d), 3.71 (1H,dd), 6.72 (1H,d), 7.44 (1H,t), 7.67 (1H,t), 7.72 (1H,s), 7.82 (1H,d), 8.07 (1H,d)

e) 1,1-Dimethylethyl 1,2,3,4-tetrahydro-3-methyl-1-(isobutyl)-6-[(2-methyl-4-quinolinyl)methyl]-2,4-dioxothieno[2,3-d]pyrimidine-5-carboxylate Methane sulphonyl chloride (0.46 ml) was added to a solution of the product of step d) (1.42 g) and triethylamine (1.54 ml) in anhydrous THF (30 ml) at room temperature under nitrogen and the mixture was stirred for 40 minutes. 10% palladium on charcoal (320 mg) was added and the mixture hydrogenated at 5 bar for 2 h. The suspension was filtered through celite, washing with methanol (100 ml). The organic material was concentrated under reduced pressure and the residue was purified by column chromatography, eluting with 1:3 ethyl acetate/i-hexane, to give the sub-title compound as a solid (1.0 g). MS (ESI) 495 {M+H}$^+$ δ $^1H_{CDCl3}$ 0.91 (6H,d), 1.61 (9H,t), 2.18 (1H,non), 2.74 (3H,s), 3.40 (3H,s), 3.64 (2H,d), 4.55 (2H,s), 7.18 (1H,s), 7.52 (1H,t), 7.71 (1H,t), 8.05-8.07 (2H,m).

f) 1,2,3,4-Tetrahydro-3-methyl-1-(isobutyl)-6-[2-methyl-4-quinolinylmethyl-2,4-dioxothieno[2,3-d]pyrimidine-5-carboxylic acid To a solution of the product of step e) (0.82 g) in dichloromethane (15 ml) under nitrogen was added trifluoroacetic acid (3 ml), and the mixture was stirred for 1 h. Saturated sodium bicarbonate solution (100 ml) was added and the mixture extracted into dichloromethane; the organic phase was washed with water (200 ml), dried over magnesium sulphate, filtered and concentrated to dryness to give the sub-title compound as a red solid (0.72 g). δ $^1H_{DMSO}$ 0.87 (6H,d), 2.13 (1H,non), 2.76 (3H,s), 3.51 (3H,s), 3.65 (2H,d), 5.21 (2H,s), 7.21 (1H,s), 7.48 (1H,t), 7.70 (1H,t), 7.89 (1H,d), 8.06 (1H,d)

g) (S) 5-[4-Hydroxyisoxazolidin-2-ylcarbonyl]-3-methyl-1-(isobutyl)-6-[2-methyl-4-quinolinylmethyl]thieno[2,3-d]pyrimidine-2,4(1H,3H)-dione The subtitle compound was prepared by the method of example 1 step g) using the products from part f) and example 1 part b). MS (APCI) 509 μM+H]$^+$. δ $^1H_{DMSO}$ 0.85 (6H,m), 2.00-2.12 (1H,m), 2.62 (3H,s), 3.21 (3H,s), 3.55-4.12 (6H,m), 4.47-4.63 (2H,m), 4.79 (1H,s,br), 5.54 (1H,s,br), 7.31/7.36 (1H,s), 7.54-7.56 (1H,m), 7.71 (1H,t), 7.93 (1H,d), 8.16-8.23 (1H,m).

EXAMPLE 18 ii

(S) 6-[6-Fluoro-4-quinolinylmethyl]-5-[4-hydroxyisoxazolidin-2-ylcarbonyl]-3-methyl-1-(isobutyl)thieno[2,3-d]pyrimidine-2,4(1H,3H)-dione

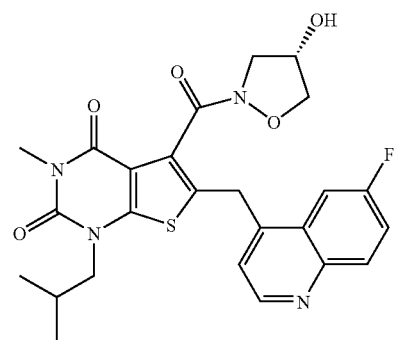

a) 6-[6-Fluoro-4-quinolinyl(hydroxy)methyl]-3-methyl-1-(isobutyl)-2,4-dioxo-1,2,3,4-tetrahydrothieno[2,3-d]pyrimidine-5-carboxylic acid, ethyl ester Prepared using the procedure described in example 1 part d) from the product of example 1 part c) and 6-fluoro-4-quinolinecarbaldehyde to give the subtitle compound. MS(ESI) 486 [M+H]$^+$. δ $^1H_{CDCl3}$ 0.87 (3H, d), 0.90 (3H, d), 1.42 (3H, t), 2.07-2.21 (1H, m), 3.38 (3H, s), 3.51 (1H, dd), 3.63 (1H, d), 3.75 (1H, dd), 4.49 (2H, q), 6.65 (1H, d), 7.48 (1H, td), 7.57 (1H, dd), 7.84 (1H, d), 8.17 (1H, dd), 8.98 (1H, d).

b) 6-[6-Fluoro-4-quinolinylmethyl]-3-methyl-1-(isobutyl-2,4-dioxo-1,2,3,4-tetrahydrothieno[2,3-d]pyrimidine-5-carboxylic acid ethyl ester Prepared using the procedure described in example 1 part e) from the product of part a) to give the subtitle compound. MS(ESI) 470 [M+H]$^+$. δ $^1H_{CDCl3}$ 0.91 (6H, d), 1.38 (3H, t), 2.13-2.26 (1H, m), 3.40 (3H, s), 3.65 (2H, d), 4.46 (2H, q), 4.53 (2H, s), 7.31 (1H, d), 7.51 (1H, td), 7.75 (1H, dd), 8.16 (1H, dd), 8.85 (1H, d).

c) 6-[6-Fluoro-4-quinolinylmethyl]-3-methyl-1-(isobutyl)-2,4-dioxo-1,2,3,4-tetrahydrothieno[2,3-d]pyrimidine-5-carboxylic acid, sodium salt Prepared using the procedure described in example 1 part f) from the product of part b) to give the subtitle compound. MS(ES)$^+$ 442 [M+2H—Na]$^+$. δ $^1H_{DMSO}$ 0.81 (6H, d), 2.02-2.16 (1H, m), 3.20 (3H, s), 3.56 (2H, d), 4.51 (2H, s), 7.59 (1H, d), 7.63 (1H, td), 8.06 (1H, dd), 8.61 (1H, dd), 8.82 (1H, d).

d) (S) 6-[6-Fluoro-4-quinolinylmethyl]-5-{4-hy-droxyisoxazolidin-2-ylcarbonyl}-3-methyl-1-(isobu-tyl thieno[2,3-d]pyrimidine-2,4(1H,3H)-dione Prepared using the procedure described-in example 1 part g) from the product of part c) and (S)-4-hydroxyisoxazolidine hydrochloride {example 1 part b)} to give the title compound. MS(ESI) 513 [M+H]$^+$. δ* $^1H_{DMSO}$ 0.82-0.85 (6H, m), 2.04-2.17 (1H, m), 3.21 (2H, s), 3.22 (1H, s), 3.55-3.68 (3H, m), 3.75-4.13 (3H, m), 4.50-4.71 (2.33H, m), 4.78-4.81 (0.67H, m), 5.50-5.56 (1H, m), 7.42-7.53 (1H, m), 7.69 (1H, td), 8.02-8.16 (2H, m), 8.86 (1H, d). (* N.B. mixture of rotamers, minor rotamer peaks not quoted; spectrum simplified at higher temperatures)

EXAMPLE 18iii (S) 6-[8-Fluoro-4-quinolinylmethyl]-5-{4-hydroxy-isoxazolidin-2-ylcarbonyl}-3-methyl-1-(isobutyl)-thieno[2,3-d]pyrimidine-2,4(1H,3H)-dione

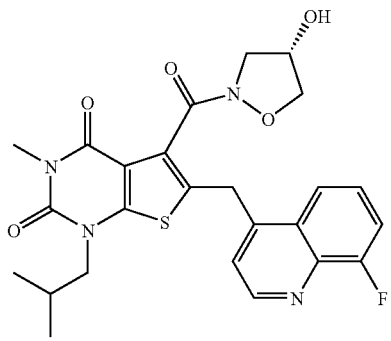

a) 6-[8-Fluoro-4-quinolinyl(hydroxy)methyl]-3-methyl-1-(isobutyl)-2,4-dioxo-1,2,3,4-tetrahydrothieno[2,3-d]pyrimidine-5-carboxylic acid, ethl ester Prepared using the procedure described in example 1 part d) from the product of example 1 part c) and 8-fluoro-4-quinolinecarbaldehyde to give the subtitle compound. MS(ESI) 486 [M+H]$^+$. δ $^1H_{CDCl_3}$ 0.85 (3H, d), 0.88 (3H, d), 1.43 (3H, t), 2.05-2.19 (1H, m), 3.38 (3H, s), 3.47 (1H, dd), 3.65 (1H, d), 3.74 (1H, dd), 4.49 (2H, q), 6.74 (1H, d), 7.38-7.50 (2H, m), 7.69 (1H, d), 7.91 (1H, dd), 9.07 (1H, d).

b) 6-[8-Fluoro-4-quinolinylmethyl]-3-methyl-1-(isobutyl)-2,4-dioxo-1,2,3,4-tetrahydrothieno[2,3-d]pyrimidine-5-carboxylic acid, ethyl ester Prepared using the procedure described in example 1 part e) from the product of part a) to give the subtitle compound. MS(ESI) 470 [M+H]$^+$. δ $^1H_{CDCl_3}$ 0.91 (6H, d), 1.37 (3H, t), 2.13-2.23 (1H, m), 3.39 (3H, s), 3.65 (2H, d), 4.45 (2H, q), 4.60 (2H, s), 7.31 (1H, d), 7.73 (1H, d), 7.44 (1H, td), 7.51-7.57 (1H, m), 7.911hd 8.94 (1H, d).

c) 6-[8-Fluoro-4-quinolinylmethyl]-3-methyl-1-(isobutyl)-2,4-dioxo-1,2,3,4-tetrahydrothieno[2,3-d]pyrimidine-5-carboxylic acid, sodium salt Prepared using the procedure described in example 1 part f) from the product of part b) to 25 give the subtitle compound. MS(ESI) 442 [M+2H—Na]$^+$. δ $^1H_{DMSO}$ 0.81 (6H, d), 2.03-2.13 (1H, m), 3.20 (3H, s), 3.57 (2H, d), 4.55 (2H, s), 7.53-7.58 (2H, m), 7.63 (1H, d), 8.45-8.50 (1H, m), 8.88 (1H, d).

d) (S) 6-[8-Fluoro-4-quinolinylmethyl]-5-{4-hy-droxyisoxazolidin-2-ylcarbonyl}-3-methyl-1-(isobu-tyl)-thieno[2,3-d]$_p$ midine-2,4(1H,3H)-dione Prepared using the procedure described in example 1 part e) from the product of part c) and (S)-4-hydroxyisoxazolidine hydrochloride {example 1 part b)} to give the title compound.

MS(ESI) 513 [M+H]$^+$. * δ $^1H_{DMSO}$ 0.83-0.85 (6H, m), 2.04-2.15 (1H, m), 3.21 (2H, s), 3.22 (1H, s), 3.52-3.72 (3H, m), 3.764.12 (3H, m), 4.55-4.70 (2.33H, m), 4.78-4.81 (0.67H, m), 5.50-5.57 (1H, m), 7.52 (0.33H, d), 7.56 (0.67H, d), 7.58-7.63 (2H, m), 8.05-8.13 (1H, m), 8.92 (1H, d)._(* N.B. 2:1 mixture of rotamers,)

EXAMPLE 18iv (S) 5-14-Hydroxyisoxazolidin-2-ylcarbonyl}-3-methyl-1-(isobutyl)-6(5-quinolinylmethyl)thieno[2,3-d]pyrimidine-2,4(1H,3H)-dione

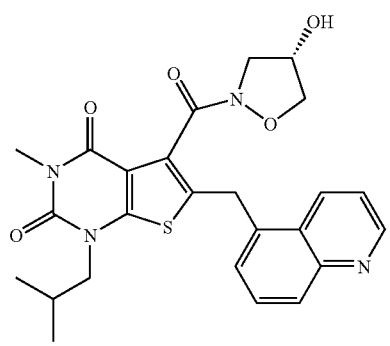

a) 6-[Hydroxy(5-quinolinyl)methyl]-3-methyl-1-(isobutyl)-2,4-dioxo-1,2,3,4-tetrahydrothieno[2,3-d]pyrimidine-5-carboxylic acid ethyl ester Prepared using the procedure described in example 1 part d) from the product of example 1 part c) and 5-quinolinecarbaldehyde to give the subtitle compound. MS(ESI) 468 [M+H]$^+$. δ $^1H_{CDCl_3}$ 0.87 (3H, d), 0.89 (3H, d), 1.33 (3H, t), 2.10-2.22 (1H, m), 3.38 (3H, s), 3.52 (1H, s, br), 3.55 (1H, dd), 3.71 (1H, dd), 4.33-4.41 (2H, m), 6.75 (1H, s), 7.39 (1H, dd), 7.77 (1H, t), 7.90 (1H, d), 8.14 (1H, d), 8.39 (1H, d), 8.91 (1H, d).

b) 3-Methyl-1-(isobutyl)-2,4-dioxo-6-(5-quinolinyl-methyl)-1,2,3,4-tetrahydrothieno[2,3-d]pyrimidine-5-carboxylic acid ethyl ester Prepared using the procedure described in example 1 part e) from the product of part a) to give the subtitle compound. MS(ESI) 452 [M+H]$^+$. δ $^1H_{CDCl_3}$ 0.87 (6H, d), 1.42 (3H, t), 2.09-2.19 (1H, m), 3.38 (3H, s), 3.60 (2H, d), 4.49 (2H, q), 4.59 (2H, s), 7.43 (1H, dd), 7.50 (1H, dd), 7.70 (1H, t), 8.11 (1H, d), 8.49 (1H, d), 8.93 (1H, dd).

c) 3-Methyl-1-(isobutyl)-2,4-dioxo-6-(5-quinolinyl-methyl)-1,2,3,4-tetrahydrothieno[2,3-d]pyrimidine-5-carboxylic acid sodium salt Prepared using the procedure described in example 1 part f) from the product of part b) to give the subtitle compound. MS(ESI) 424 [M+2H—Na]$^+$. δ $^1$H DMSO 0.79 (6H, d), 2.00-2.10 (1H, m), 3.19 (3H, s), 3.53 (2H, d), 4.52 (2H, s), 7.46 (1H, dd), 7.64 (1H, d), 7.71 (1H, t), 7.93 (1H, d), 8.85 (1H, dd), 9.14 (1H, d).

d) (S) 5-14-Hydroxyisoxazolidin-2-ylcarbonyl}-3-methyl-1-(isobutyl)-6-(5-quinolin lmethyl)thieno[2,3-d]pyrimidine-2,4(1H,3H)-dione Prepared using the procedure described in example 1 part g) from the product of part c) and example 1 part b) to give the title compound. MS(ESI) 495 [M+H]$^+$. δ $^1$H DMSO 0.80-0.83 (6H, m), 1.99-2.06 (1H, m), 3.20 (2H, s), 3.21 (1H, s), 3.50-3.63 (3H, m), 3.77-4.14 (3H, m), 4.548-4.70 (2.33H, m), 4.79-4.82 (0.67H, m), 5.50 (0.33H, d), 5.56 (0.67H, d), 7.54 (1H, dd), 7.59 (0.33H, d), 7.63 (0.67H, d), 7.75 (1H, t), 7.98 (1H, d), 8.60 (0.33H, d), 8.64 (0.67H, d), 8.91 (1H, d).

EXAMPLE 19

(S) 5-{4-Hydroxyisoxazolidin-2-ylcarbonyl}-3-methyl-1-propyl-6-(quinolin-4-ylmethyl)thieno[2,3-d]pyrimidine-2,4(1H,3H)-dione a) 6-Chloro-3-methyl-1-propylpyrimidine-2,4(1H,3H)-dione 6-chloro-3-methyl uracil (10 g) and potassium carbonate (10.34 g) in DMF (70 ml) under nitrogen was treated with n-propyl iodide (25.4 g) and heated at reflux for 8 h. The reaction 30 was cooled and then poured into water (700 ml) and extracted with ethyl acetate. The combined organics were dried and evaporated in vacuo to afford the subtitle compound an orange oil, 17.52 g. δ $^1$H$_{CDCl3}$ 0.98 (3H, t), 1.74 (2H, sextet), 3.33 (3H, s), 4.02 (2H, t), 8.02 (1H, s).

b) 3-Methyl-1-propyl-6-mercaptopyrimidine-2,4(1H,3H)-dione

The product of step a) (11.43 g) in ethanol (400 ml) was treated with NaSH (6.31 g) under nitrogen. After stirring for 48 h at room temperature the solvent was evaporated in vacuo and the residue diluted with water. The aqueous phase was washed with ethyl acetate then acidified with 2M HCl. This was then extracted with ethyl acetate and the combined organics dried and evaporated in vacuo to afford the subtitle compound as an orange oil, 7 g. δ $^1$H$_{CDCl3}$ 0.97 (3H, t), 1.72 (2H, m), 3.31 (3H, s), 4.29 (2H, s).

c) Ethyl 3-methyl-2,4-dioxo-1-propyl-1,2,3,4-tetrahydrothieno[2,3-d]pyrimidine-5-carboxylate The product of step b) (6.95 g) in dry dimethylformamide (100 ml) was added potassium carbonate (2.4 g) and stirred for 10 min. Ethyl bromopyruvate (5 ml) was added and was stirred under nitrogen at room temperature for 2 h. The reaction was poured into water (1 L), acidified (2M HCl) and extracted with ethyl acetate. The organic extracts were washed with brine (100 ml). Drying and evaporation afforded an oil. The oil was dissolved in dichloromethane (100 ml) and cooled in ice whilst stirring. Titanium tetrachloride (7.58 ml) was added and stirring continued under nitrogen for 2 h. The reaction was poured into water (1 L) and extracted with dichloromethane. The organics were dried and evaporated in vacuo. The residue was purified by chromatography (SiO$_2$/ethyl acetate-dichloromethane 0-8%) to afford the subtitle compound as an orange oil, 4.64 g. δ $^1$H$_{CDCl3}$ 1.02 (3H, t), 1.83 (2H, sextet), 3.42 (3H, s), 3.95 (2H, t), 4.41 (2H, q), 7.30 (1H, s). MS (APCI) 297.1 (M$^+$+H)

d) Ethyl 6-[hydroxy(quinolin-4-yl)methyl]-3-methyl-2,4-dioxo-1-propyl-1,2,3,4-tetrahydrothieno[2,3-d]pyrimidine-5-carboxylate The sub-title compound was prepared using the method of example 1, part d) using the product of step c). δ $^1$H$_{CDCl3}$ 0.89 (3H, t), 1.41 (3H, t), 1.65 (2H, sextet), 3.38 (3H, s), 3.75 (1H, d), 3.64 (1H, m), 3.80 (1H, m), 4.48 (2H, q), 6.78 (1H, d), 7.52 (1H, m), 7.72 (1H, m) 7.84 (1H, m), 7.90 (1H, d), 8.16 (1H, m), 9.02 (1H, d).

e) Ethyl 3-methyl-2,4-dioxo-1-propyl-6-(quinolin-4-ylmethyl)-1,2,3,4-tetrahydrothieno[2,3-d]pyrimidine-5-carboxylate.

The sub-title compound was prepared using the method of example 1 e) using the product of step d). MS (ESI) 437.9 (M$^+$+H)

f) Sodium 3-methyl-2,4-dioxo-1-propyl-6-(quinolin-4-ylmethyl)-1,2,3,4-tetrahydrothieno[2,3-d]pyrimidine-5-carboxylate The sub-title compound was prepared by the method of example 1 part f) using the product of step e). δ $^1$H$_{DMSO}$ 0.80 (3H, t), 1.57 (2H, sextet), 3.68 (2H, t), 4.55 (2H, s), 3.19 (3H, s), 7.53 (2H, d), 7.57 (1H, m) 7.74 (1H, m), 8.01 (1H, d), 8.61 (1H, d), 8.83 (1H, d).

g) (S) 5-{4-Hydroxyisoxazolidin-2-ylcarbonyl}-3-methyl-1-propyl-6-(quinolin-4-ylmethyl)thieno[2,3-d]pyrimidine-2,4(1H,3H)-dione Prepared as the method of example 1, part g) using the product of step f) and (S)-isoxazolidin-4-ol hydrochloride. δ $^1$H DMSO 0.84 (3H, td), 1.60 (2H, septet), 3.21 (3H, d), 3.56 (1H, d), 3.73 (3H, m), 3.81 (1H, d), 3.90 (1H, m), 4.61 (2H, dd), 4.79 (1H, s), 5.52 (1H, m), 7.46 (1H, dd), 7.63 (1H, m) 7.79 (1H, m), 8.05 (1H, d), 8.27 (1H, dd), 8.87 (1H, d). MS (APCI) 481.1 (M$^+$+H)

EXAMPLE 20

(S) 5-{4-Hydroxyisoxazolidin-2-ylcarbonyl}-3-methyl-1-(isopropyl)-6-(4-quinolinylmethyl)thieno[2,3-d]pyrimidine-2,4(1H,3H)-dione

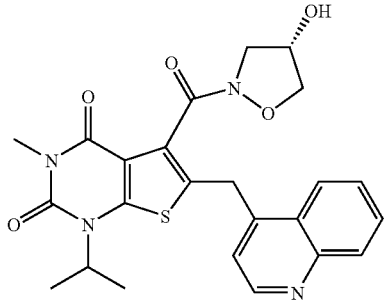

a) Diethyl 2-((isopropyl)amino)thiophene-3,4-dicarboxylate

Ethoxycarbonylmethylene triphenyl phosphorane (33.8 g) in dry THF (200 ml) was treated with isopropyl isothiocyanate (10.1 g) at 65° C. for 16 h under nitrogen. The mixture was cooled to −78° C. and ethyl bromo-pyruvate (19.5 g) was added. The reaction was allowed to warm slowly to room temperature. After 24 h at room temperature more ethyl bromo-pyruvate (3.17 g) was added and the mixture was stirred at room temperature for 16 h. The reaction was poured into water (1.5 L) and extracted into ether. Drying and evaporation gave an oil which was chromatographed (SiO$_2$/5:1 isohexane-ethyl acetate) to afford the subtitle compound (21.2 g). δ $^1H_{CDCl_3}$ 1.23-1.43 (12H, m), 3.46 (1H, m), 4.2-4.35 (4H, m), 6.50 (1H, s), 7.52 (1H, br.d)

b) Ethyl 1,2,3,4-tetrahydro-3-methyl-1-(isopropyl)-2,4-dioxo-thieno[2,3-d]pyrimidine-5-carboxylate Silver cyanate (4.5 g) suspended in anhydrous toluene (30 ml) under nitrogen was treated dropwise with acetyl chloride (1.78 ml) and stirred vigorously for 30 min. The product of step a) (7.12 g) dissolved in anhydrous toluene (5 ml) was added and the mixture was stirred for 24 h. Ether (120 ml) was added and the insoluble material was filtered off and washed with a small volume of ether. The combined organic solutions were washed with saturated sodium bicarbonate solution, dried and evaporated. The residue was treated with a solution of sodium ethoxide in ethanol (prepared from sodium 1.95 g and ethanol 35 ml) at room temperature for 24 h. The reaction was cooled in ice and treated with trimethylsilyl chloride (20 ml) and stirred at room temperature overnight. All volatiles were removed in vacuo and the residue partitioned between water and ethyl acetate. Drying and evaporation of the organic solution left a residue. This was taken in dry DMF (50 ml) with potassium carbonate (6.95 g) and methyl iodide (8.5 g) for 24 h at room temperature. The mixture was poured into water (1 L), acidified and extracted into ether. Washing with brine, drying and evaporation gave an oil. Chromatography (SiO$_2$/3:1 isohexane-ethyl acetate) to afford the subtitle compound (3.1 g). δ $^1H_{CDCl_3}$ 1.39 (3H, t), 1.6 (6H, d), 3.39 (3H, s), 4.4 (2H, q), 7.25 (1H, s). MS (APCI) (M$^+$+H) 297 c) 6-[Hydroxy(4-quinolinyl)methyl]-3-methyl-1-(isopropyl)-2,4-dioxo-1,2,3,4-tetrahydrothieno[2,3-d]pyrimidine-5-carboxylic acid, ethyl ester Prepared using the procedure described in example 1 part d) from the product of part b) and 4-quinolinecarbaldehyde to give the subtitle compound. MS(ESI) 454 [M+H]$^+$. δ $^1H_{CDCl_3}$ 1.41 (3H, t), 1.43 (3H, d), 1.46 (3H, d), 3.35 (3H, s), 3.66 (1H, d), 4.25-4.45 (1H, m), 4.45-4.51 (2H, m), 6.78 (1H, d), 7.53 (1H, td), 7.72 (1H, td), 7.83 (1H, d), 7.92 (1H, d), 8.17 (1H, dd), 9.02 (1H, d).

d) 3-Methyl-1-(isopropyl)-2,4-dioxo-6-(4-quinolinylmethyl-1,2,3,4-tetrahydrothieno[2,3-(d]pyrimidine-5-carboxylic acid, ethyl ester Prepared using the procedure described in example 1 part c) from the product of part c) to give the subtitle compound. MS(ESI) 438 [M+H]$^+$. δ $^1H_{CDCl_3}$ 1.37 (3H, t), 1.49 (6H, d), 3.36 (3H, s), 4.44 (2H, q), 4.60 (2H, s), 4.30-4.60 (1H, m), 7.31 (1H, d), 7.61 (1H, td), 7.76 (1H, td), 8.13 (1H, dd), 8.16 (1H, dd), 8.81 (1H, d).

e) 3-Methyl-1-(isopropyl)-2,4-dioxo-6-(4-quinolinylmethyl)-1,2,3,4-tetrahydrothieno[2,3-d]pyrimidine-5-carboxylic acid, sodium salt Prepared using the procedure described in example 1 part f) from the product of part d) to give the subtitle compound. MS(ESI) 410 [M+2H-Na]$^+$. δ $^1H_{DMSO}$ 1.36 (6H, d), 3.16 (3H, s), 4.10-4.35 (1H, m), 4.52 (2H, s), 7.53 (1H, d), 7.58 (1H, t), 7.74 (1H, t), 8.00 (1H, d), 8.62 (1H, d), 8.82 (1H, d).

f)(S) 5-{4-Hydroxyisoxazolidin-2-ylcarbonyl}-3-methyl-1-(isopropyl)-6-(4-quinolinylmethyl)thieno[2,3-d]pyrimidine-2,4(1H,3H)-dione Prepared using the procedure described in example 1 part g) from the product of part e) to give the title compound. MS(ESI) 481 [M+H]$^+$. * δ $^1H_{DMSO}$ 1.40-1.44 (6H, m), 3.18 (2H, s), 3.19 (1H, s), 3.54 (1H, d), 3.75 (0.33H, d), 3.81 (0.67H, d), 3.89 (0.67H, dd), 3.89-3.98 (0.33H, m), 3.99-4.05 (0.33H, m), 4.10 (0.67H, dd), 4.22-4.40 (1H, m), 4.50-4.68 (2.33H, m), 4.79 (0.67H, d), 5.50 (0.33H, d), 5.54 (0.67H, d), 7.44 (0.33H, d), 7.48 (0.67H, d), 7.64 (1H, t), 7.78 (1H, t), 8.05 (1H, d), 8.26 (0.33H, d), 8.30 (0.67H, d), 8.87 (1H, d). (* N.B. 2:1 mixture of major rotamers, minor rotamer peaks not quoted)

EXAMPLE 21i (S) 5-[4-Hydroxyisoxazolidin-2-ylcarbonyl]-3-methyl-1-(isobutyl)-6[(2-methyl-1H-pyrrolo[2,3,b]pyridin-3-yl)methyl]thieno[2,3,d]pyrimidine-2,4(1H,31)-dione

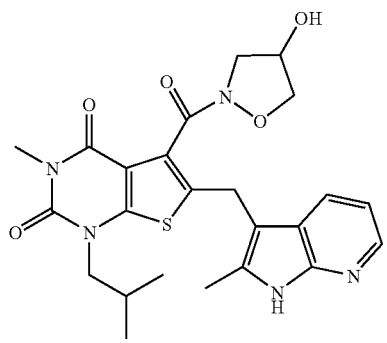

a) 1,2,3,4-Tetrahydro-3-methyl-1-(isobutyl)-2,4-dioxo-6-(1H-pyrrolo[2,3,d]pyridin-3-ylmethyl)thieno[2.3,d]pyrimidine-5-carboxylic acid, methyl ester Prepared by the method of example 6 part a) using the product of example 3 part b) and 2-methyl-7-azaindole. MS(APCI) 427 [M+H]$^+$. δ $^1$H$_{DMSO}$ 0.83 (6H,d), 2.09 (1H, heptet), 3.20 (3H,s), 3.61 (2H,d), 3.86 (3H,s), 4.22 (2H,s), 7.02-7.05 (1H,m), 7.43 (1H,m), 7.88 (1H,d), 8.20 (1H,d), 11.56 (1H,s,br)

b) 1,2,3,4-Tetrahydro-3-methyl-1-(isobutyl)-2,4-dioxo-6-(1H-pyrrolo[2,3,b]pyridin-3-ylmethyl)thieno[2,3,d]pyrimidine-5-carboxylic acid The sub-title compound (1.22 g) was prepared from the product of part a) by the method of example of example 3, step d). MS (ESI) 413 [M+H]$^+$ c) (S) 5-[[4-Hydroxyisoxazolidin-2-yl]carbonyl]-3-methyl-1-(isobutyl)-6-[(2-methyl-1H-pyrrolo[2,3,b]pyridin-3-yl)methyl]thieno[2,3,d]pyrimidine-2,4(1H,3H)-dione The title compound was prepared from the product of step b) by the method of example 1, step g). MS (APCI) 498 [M+H]$^+$. δ $^1$H$_{DMSO}$ 0.87-0.90 (6H,m), 2.09-2.15 (1H,m), 2.46 (3H,m), 3.25-3.27 (3H,m), 3.58-3.72 (3H,m), 3.81-3.93 (2H,m), 4.03-4.22 (3H,m), 4.72-4.86 (1H,m), 5.57-5.82 (1H, m), 7.00-7.03 (1H,m), 7.84-7.89 (1H,m), 8.14-8.15 (1H,m), 11.51 (1H,s)

EXAMPLE 21ii (R) 5-[4-Hydroxyisoxazolidin-2-ylcarbonyl-3-methyl-1-(isobutyl)-6-[(2-methyl-1H-pyrrolo[2,3,b]pyridin-3-yl)methyl]thieno[2,3,d]pyrimidine-2,4(1H,3H)-dione The title compound was prepared from the product of example 21i), step b) by the method of

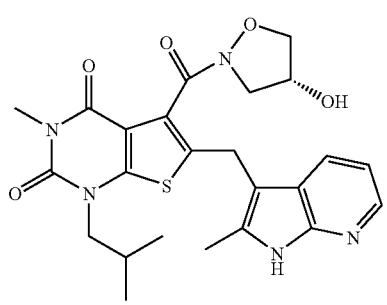

example 1, step g) using (R)-4-hydroxyisoxazolidine, example 2 part b). MS (APCI) 498 [M+H]$^+$. δ $^1$H$_{DMSO}$ 0.81-0.84 (6H,m), 2.03-2.09 (1H,m), 2.39 (3H,s) 3.16-3.19 (3H,m), 3.25-3.66 (3H,m), 3.75-3.89 (2H,m), 3.97-4.16 (3H, m), 4.63-4.80 (1H,m), 5.53-5.55 (1H,m), 6.94-6.98 (1H,m), 7.76-7.83 (1H,m), 8.08-8.09 (1H,m), 11.45 (1H,s).

EXAMPLE 22

(S) 5-[4-Hydroxyisoxazolidin-2-ylcarbonyl]-3-methyl-1-(isopropyl)-6-[2-methyl-1H-pyrrolo[2,3-b]pyridin-3-yl)methyl]thieno[2,3-d]pyrimidine-2,4(1H,3H)-dione

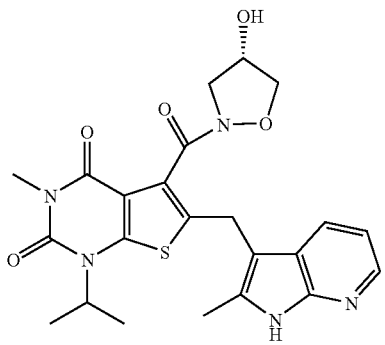

a) Methyl 6-(bromomethyl)-1,2,3,4-tetrahydro-3-methyl-1-(isopropyl)-2,4-dioxothieno[2,3-d]pyrimidine-5-carboxylate A solution of the product of example 8, part b), (1.6 g), N-bromosuccinimide (1 g), and azoisobutyronitrile (10 mg) in ethyl acetate (25 ml) was refluxed for 1 h. The solution was cooled to room temperature, washed successively with dilute sodium hydroxide solution and water, the organic extracts were dried over anhydrous magnesium sulfate, filtered and evaporated under reduced pressure. The residue was purified by column chromatography over silica, eluting with diethyl ether/i-hexane (1:1) to give the sub-title compound as a solid (1.5 g). δ $^1$H$_{CDCl3}$ 1.62 (6H, d), 3.37 (3H, s), 3.99 (3H, s), 3.60-3.70 (3H, m)

b) Methyl 1,2,3,4-tetrahydro-3-methyl-1-(isopropyl)-6-[2-methyl-1H-pyrrolo[2,3-b]pyridin-3-ylmethyl]-2,4-dioxothieno[2,3-d]pyrimidine-5-carboxylate To a stirred suspension of 60% sodium hydride (0.23 g) in THF (10 ml) was added a solution of 2-methylazaindole (0.37 g) in THF (10 ml) dropwise under nitrogen at ambient temperature, and after 5 min. 1M zinc chloride in ether (5.6 ml) was added. After stirring for 5 min. a solution of the product of part a) (0.88 g) in THF (10 ml) was added and the mixture stirred for 3 h. It was quenched with water and extracted with ethyl acetate, the organic extracts were dried over anhydrous magnesium sulfate, filtered and evaporated under reduced pressure. The residue was purified by column chromatography over silica, eluting with ethyl acetate/i-hexane (1:1) to give the sub-title compound as a solid (0.4 g). MS (ESI) 427 [M+H]$^+$. δ $^1$H$_{CDCl3}$ 1.48 (6H, d), 2.49 (3H, s), 3.36 (3H, s), 4.11 (2H, s), 4.20 (1H, s, br), 7.03-7.06 (1H, m), 7.79 (1H, d), 8.23 (1H, d), 9.10 (1H, s)

c) 1,2,3,4-Tetrahydro-3-methyl-1-(isopropyl)-6-[2-methyl-1H-pyrrolo[2,3-b]pyridin-3-yl methyl]-2,4-dioxothieno[2,3-d]pyrimidine-5-carboxylic acid Prepared from the product of part b) following the procedure of example 1, part f) to give the sub-title compound as a solid. MS (ESI) 413 [M+H]+ d) (S) 5-[4-Hydroxyisoxazolidin-2-ylcarbonyl]-3-methyl-1-(isopropyl)-6-[2-methyl-1H-pyrrolo[2,3-b]pyridin-3-ylmethyl]thieno[2,3-d]pyrimidine-2,4(1H,3H)-dione Prepared from the product of part c) and (S)-4-isoxazolidinol hydrochloride [example 1, part b)] following the procedure of example 1, part g) to give the title compound as a solid. MS(APCI) 484 [M+H]$^+$. δ $^1H_{DMSO}$ 1.37-1.40 (6H, m), 2.40 (3H, s), 3.17-3.18 (3H, m), 3.52-4.28 (7H, m), 4.66-4.79 (1H, m), 5.50-5.55 (1H, m), 6.95-6.99 (1H, m), 7.80-7.86 (1H, m), 8.08-8.10 (1H, m), 11.45 (1H, s).

EXAMPLE 23

(S)-6-[4,5-Dichloro-2-(hydroxymethyl)-1H-imidazol-1-yl methyl]-5-[4-hydroxyisoxazolidin-2-ylcarbonyl]-3-methyl-1-(isobutyl)-thieno 2,3-d]pyrimidine-2,4(1H,3H)-dione

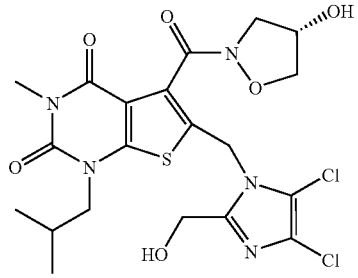

a) 4,5-Dichloro-1H-imidazole-2-methanol

Potassium hydroxide (0.12 g, 2.14 mmol) in water (4 ml) was added to 4,5-dichloromethane, and the suspension was stirred for 35 min. Paraformaldehyde (0.11 g, 3.66 mmol) was added portionwise and the reaction mixture was stirred over night, then acidified with dilute HCl to pH 1 and then concentrated in vacuo to give a white solid, 0.6 g (98%). δ $^1H_{CDCl3}$ 4.36 (2H, s)

b) 6-[4,5-Dichloro-2-(hydroxymethyl)-1H-imidazol-1-ylmethyl]-1,2,3,4-tetrahydro-3-methyl-1-(isobutyl)-2,4-dioxo- thieno[2,3-d]pyrimidine-5-carboxylic acid methyl ester Potassium carbonate (0.14 g, 3.1 mmol) and the product of part a) (0.51 g, 3.09 mmol), were added to a solution of the product of example 3 part b) in DMF, and the reaction mixture was stirred for 16 h. The solid precipitate formed was filtered, and the filtrate was concentrated in vacuo to give an orange solid 0.6 g, contains DMF. δ $^1H_{CDCl3}$ 0.99 (6H, m), 2.19-2.31 (1H,m), 3.4 (3H,s), 3.72 (2H,d), 4.0 (3H,s), 4.68 (2H,s), 5.45 (2H,s).

c) 6-[4,5-Dichloro-2-(hydroxymethyl)-1H-imidazol-1-ylmethyl]-1,2,3,4-tetrahydro-3-methyl-1-(isobutyl)-2,4-dioxo-thieno[2,3-d]pyrimidine-5-carboxylic acid Prepared from the product of step b) following the procedure of example 3, step d). MS(ESI) 484 [M+H]$^+$ d) 6-[4,5-Dichloro-2-(hydroxymethyl)-1H-imidazol-1-ylmethyl]-5-[(4S)-4-hydroxyisoxazolidin-2-ylcarbonyl]-3-methyl-1-(isobutyl)-thieno[2,3-d]pyrimidine-2,4(1H,3H)-dione Prepared form the product of step c) using the procedure of example 3 part e). The product was purified by reverse phase preparative HPLC eluting with ammonium acetate:acetonitrile (70:30) to give the title compound as a white solid. δ $^1H_{CDCl3}$ 0.89 (6H, m), 2.06-2.21 (1H,m), 3.21 (3H,s), 3.62-4.18 (6H,m), 4.44-4.78 (2H,m), 5.41 (2H,m), 5.53 (1H,m) and 5.72-5.75 (1H,m).

EXAMPLE 24

(S)-6[135-Dimethyl-1H-pyrazol-1-yl methyl]-5-[4-hydroxyisoxazolidin-2-ylcarbonyl]-3-methyl-1-(isobutyl)-thieno[2,3-d]pyrimidine-2,4(1H,3H)-dione

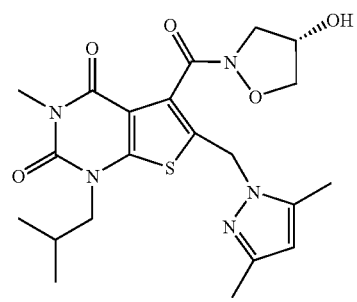

a) 6-[3,5-Dimethyl-1H-pyrazol-1-ylmethyl]-1,2,3,4-tetrahydro-3-methyl-1-(isobutyl)-2,4-dioxo-thieno[2,3-d]pyrimidine-5-carboxylic acid methyl ester The product of example 3 part b) (0.4 g, 1.03 mmol), 2,4-dimethylpyrazole (0.2 g, 2.06 mmol) and dimethyl acetamide (approx. 0.5 ml) were heated in a microwave oven for 5 mins at 100° C. The reaction mixture was concentrated in vacuo and then triturated, 0.34 g (84%). MS (ESI) 405 [M+H]+ b) 6-[3,5-Dimethyl-1H-pyrazol-1-ylmethyl]-12,3,4-tetrahydro-3-methyl-1-(isobutyl)-2,4-dioxo- thieno[2,3-d]pyrimidine-5-carboxylic acid Prepared from the product of step a) following the procedure of example 3, step d). MS (ESI) 391 [M+H]$^+$ c) 6-[3,5-Dimethyl-1H-pyrazol-1-yl methyl]-5-[(4)A-hydroxyisoxazolidin-2-ylcarbonyl]-3-methyl-1-(isobutyl)-thieno[2,3-d]pyrimidine-2,4(1H,3H)-dione Prepared form the product of step b) using the procedure of example 3 part e). The product was purified by reverse phase HPLC eluting with ammonium acetate:acetonitrile (70:30) to give the title compound as a white solid. MS (ESI) 462 [M+H]$^+$. δ $^1H_{CDCl3}$ 0.9 (6H, m), 2.09-2.19 (1H,m), 2.2 (3H,s), 3.2 (3H,s), 3.52-4.1 (6H,m), 4.81-4.77 (1H,m), 5.16-5.23 (2H,m), 5.49-5.57 (1H,m) and 5.82 (1H,s).

EXAMPLE 25

(S)-6-[2,3-Dihydro-2-oxo-1H-benzimidazol-1-ylmethyl]-5-[4-hydroxyisoxazolidin-2-yl carbonyl]-3-methyl-1-(isobutyl)- thieno[2,3-d]pyrimidine-2,4(1H,3H)-dione

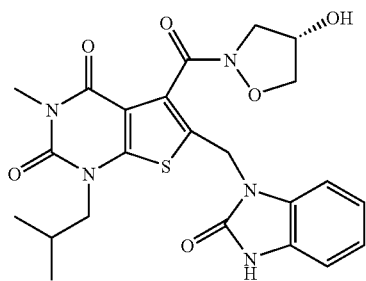

a) 6-[2,3-Dihydro-2-oxo-1H-benzimidazol-1-ylmethyl]-1,2,3,4-tetrahydro-3-methyl-1-(isobutyl)-2,4-dioxo-thieno[2,3-d]pyrimidine-5-carboxylic acid, methyl ester The product of example 3 part b) (0.5 g, 1.28 mmol), 2-chlorobenzimidazole (0.21 g, 1.37 mmol), potassium carbonate (0.36 g, 2.6 mmol) and DMF (10 ml) were stirred for 1.5 h. Ethyl acetate and water were added to the reaction mixture. The two phases were separated, the organic layer was dried (MgSO4) and then concentrated in vacuo. The residue was purified by biotage eluting with dichloromethane to give the sub-title compund as a pale yellow solid, 0.36 g (61%). δ $^1H_{D6DMSO}$ 0.83 and 0.91 (6H, d), 2.1-2.22 (1H,m), 3.38 (3H,s), 3.67 (2H,d), 4.1 (3H,s), 5.58 (2H,s), 7.26-7.38 (2H,m), 7.41-7.48 (1H,m) and 7.7-7.8 (1H,m).

b) 6-[2,3-Dihydro-2-oxo-1H-benzimidazol-1-ylmethyl]-1,2,3,4-tetrahydro-3-methyl-1-(isobutyl)-2,4-dioxo-thieno[2,3-d]pyrimidine-5-carboxylic acid The product of step a) (0.36 g, 0.65 mmol) was added to a solution of THF (10 ml), water (1 ml), and triethylamine (0.05 ml) in a sealed tube, which was heated at 180° C. for 3 days. The reaction mixture was concentrated in vacuo to give the sub-title compound (0.3 g crude yield). MS (ESI) 440 [M+H]$^+$ c) 6-[2,3-Dihydro-2-oxo-1H-benzimidazol-1-ylmethyl]-5-[(4S)-4-hydroxyisoxazolidin-2-yl carbonyl]-3-methyl-1-(isobutyl) thieno[2,3-d]pyrimidine-2,4(1H,3H)-dione Prepared form the product of step b) using the procedure of example 3 part e). The product was purified by reverse phase HPLC eluting with ammonium acetate:acetonitrile (80:20) to give the title compound as a pale yellow foam after trituration with diethyl ether. δ $^1H_{D6-DMSO}$ 0.93 (6H, m), 2.1-2.24 (1H,m), 3. (2H,s), 3.26 (3H,s), 3.52-4.18 (5H, m), 4.62-4.82 (1H,s), 5.02-5.2 (2H,s), 6.96-7.03 (2H,m), 7.17-7.19 (1H,m).

EXAMPLE 26

(S) 6-[3,5-Dimethyl-1H-pyrazol-4-ylmethyl]-5-[4-hydroxyisoxazolidin-2-yl carbonyl]-3-methyl-1-propylthieno[2,3-d]pyrimidine-2,4(1H,3H)-dione

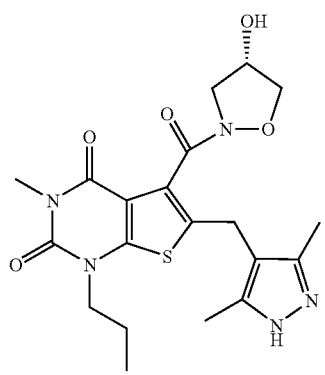

a) 6-[3,5-Dimethyl-1H-pyrazol-4-ylmethyl]-3-methyl-2,4-dioxo-1-propyl-1,2,3,4-tetrahydrothieno[2,3-d]pyrimidine-5-carboxylic acid sodium salt.

Zinc bis(acetylacetonate) (0.405 g) was added to a solution of the product of example 9, part c), (0.56 g) in chloroform (15 ml) and the resulting suspension stirred under reflux for 15 minutes then cooled to room temperature. Saturated sodium bicarbonate solution (10 ml) was added and the mixture stirred vigorously for 5 minutes, filtered then extracted with dichloromethane (2×25 ml). Combined organic extracts were treated with aqueous hydrazine solution (35%, 0.26 ml), stirred for 16 hours, dried over anhydrous magnesium sulphate, filtered and evaporated under reduced pressure. The residue was dissolved in tetrahydrofuran (15 ml) and methanol (3.1 ml) then treated with sodium hydroxide solution (1M, 2.16 ml) and the mixture stirred for 18 hours. The resulting precipitate was collected by filtration, washed with tetrahydrofuran and dried in vacuo to give the sub-title compound (0.42 g).
MS(ESI) 377 [M+2H−Na]$^+$ δ $^1H_{DMSO}$ 0.85 (3H, t), 1.63 (2H, sextet), 2.08 (6H, s), 3.19 (3H, s), 3.74 (4H, m).

b) (S) 6-[3,5-Dimethyl-1H-pyrazol-4-ylmethyl]-5-[4-hydroxyisoxazolidin-2-ylcarbonyl-3-methyl-1-propylthieno[2,3-d]pyrimidine-2,4(1H,3H)-dione Prepared from the product of part a) and (S)-4-isoxazolidinol hydrochloride [example 1, part b)] following the procedure of example 1, part g) to give the title compound as a solid. MS(APCI) 440 [M+H]$^+$. δ $^1H_{DMSO}$ (90° C.*) 0.88 (3H, t), 1.68 (1H, sex), 2.08 (6H, s), 3.21 (3H, s), 3.46 (1H, d), 3.67-4.14 (7H, m), 4.63-4.77 (1H, m), 5.23 (1H, s, br), 11.86 (1H, s, br). (*N.B. Substance exists as a mixture of rotamers therefore NMR complicated at room temperature but simplified at elevated temperature)

EXAMPLE 26i (S) 6-[3,5-Dimethyl-1H-pyrazol-4-ylmethyl]-5-[4-hydroxyisoxazolidin-2-ylcarbonyl]-1-isopropyl-3-methylthieno[2,3-d]pyrimidine-2,4(1H,3H)-dione

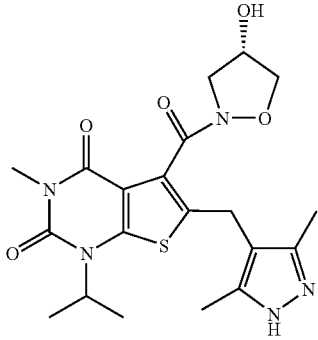

a) 6-[3,5-dimethyl-1H-pyrazol-4-ylmethyl]-1-isopropyl-3-methyl-2,4-dioxo-1,2,3,4-tetrahydrothieno[2,3-d]pyrimidine-5-carboxylic acid sodium salt Prepared from the product of example 8, part b) following the procedure of example 26, part a) to give the sub-title compound as a solid. MS(ESI) 377 [M+2H-Na]+ δ $^1H_{DMSO}$ 1.44 (6H, d), 2.10 (6H, s), 3.17 (3H, s), 3.74 (2H, s), 4.34 (1H, s, br), 12.01 (1H, s, br).

b) (S) 6-[3,5-Dimethyl-1H-pyrazol-4-yl methyl]-5-[4-hydroxyisoxazolidin-2-ylcarbonyl]-1-isopropyl-3-methylthieno[2,3-d]pyrimidine-2,4(1H,3H)-dione Prepared from the product of part a) and (S)-4-isoxazolidinol hydrochloride [example 1, part b)] following the procedure of example 1, part g) to give the title compound as a solid. MS (APCI) 448 [M+H]+. δ $^1H_{DMSO}$ 1.43-1.46 (6H, m), 2.09 (6H, s, br), (1.87H, s), 3.18 (1.13H, s), 3.47 (0.62H, d), 3.58 (0.38H, d), 3.70-3.79 (3H, m), 3.80-3.86 (1H, m), 3.88-4.04 (0.38H, m), 4.10 (0.62H, dd), 4.37 (1H, s, br), 4.58-4.78 (1H, s, br), 5.50 (1H, d), 12.11 (1H, s).

EXAMPLE 27

(S)-6-[3,5-Dimethylisoxazol-4-ylmethyl]-5-[4-hydroxyisoxazolidin-2-ylcarbonyl]-1-(isobutyl)-3-methylthieno[2,3-d]pyrimidine-2,4(1H,3H)-dione

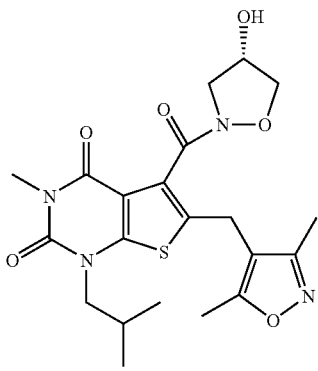

a) Methyl 6-[3,5-dimethylisoxazol-4-ylmethyl]-1-(isobutyl)-3-methyl-2,4-dioxo-1,2,3,4-tetrahydrothieno[2,3-d]pyrimidine-5-carboxylate Zinc bis(acetylacetonate) (0.724 g) was added to a solution of the product of example 3, part b), (1.0 g) in chloroform (20 ml) and the resulting suspension stirred under reflux for 30 minutes then cooled to room temperature. Saturated sodium bicarbonate solution (20 ml) was added and the mixture stirred vigorously for 5 minutes, filtered then extracted with dichloromethane (2×20 ml). Organic extracts were dried over anhydrous magnesium sulphate, filtered and evaporated under reduced pressure. The residue was dissolved in ethanol (10 ml), hydroxylamine hydrochloride (0.54 g) and pyridine (0.62 ml) were added and the mixture stirred for 16 hours. Hydrochloric acid (2M, 5 ml) was added and stirring continued for 24 hours. The mixture was evaporated to low volume then added to saturated sodium bicarbonate solution (25 ml) and extracted with ethyl acetate (2×25 ml). Organic extracts were dried over anhydrous magnesium sulphate, filtered and evaporated under reduced pressure. The residue was purified by column chromatography over silica, eluting with ethyl acetate/iso-hexane (2:1) and the product triturated with ether to give the sub-title compound (0.55 g). MS(ESI) 406 [M+H]+. δ $^1H_{CDCl3}$ 0.95 (6H, d), 2.18 (3H, s), 2.18-2.30 (1H, m), 3.39 (3H, s), 3.70 (2H, d), 3.85 (2H, s), 3.95 (3H, s).

b) 6-[3,5-dimethylisoxazol-4-ylmethyl]-1-(isobutyl)-3-methyl-2,4-dioxo-1,2,3,4-tetrahydrothieno[2,3-d]pyrimidine-5-carboxylic acid Prepared from the product of part a) following the procedure of example 3, part d) to give the sub-title compound as a solid. MS(ESI) 392 [M+H]+. δ $^1H_{DMSO}$ 0.89 (6H, d), 2.09 (3H, s), 2.09-2.20 (1H, m), 2.34 (3H, s), 3.22 (3H, s), 3.70 (2H, d), 4.04 (2H, s).

c) 6-[3,5-dimethylisoxazol-4-yl methyl]-5-[(4S)-4-hydroxyisoxazolidin-2-yl carbonyl]-1-(isobutyl)-3-methylthieno[2,3-d]pyrimidine-2,4(1H,3H)-dione Prepared from the product of part b) and (S)-4-isoxazolidinol hydrochloride [example 1, part b)] following the procedure of example 1, part g) to give the title compound as a foam. MS (APCI) 463 [M+H]+. δ $^1H_{DMSO}$ 0.89 (6H, d), 2.10 (3H, s), 2.13-2.24 (1H, m), 2.30 (3H, s), 3.22 (3H, s), 3.44 (1H, d, br), 3.65-3.78 (3H, m), 3.82 (2H, s), 3.85-4.10 (2H, m), 4.70 (1H, s, br), 5.18 (1H, d).

EXAMPLE 28

6-[4,5-Dichloro-2-methyl-1H-imidazol-1-ylmethyl]-1-ethyl-5-[(4S)-4-hydroxy-2-isoxazolidinylcarbonyl]-3-methyl-thieno[2,3-d]pyrimidine-2,4(1H,3H)-dione

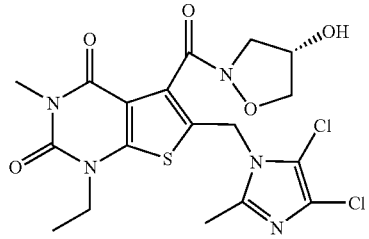

a) 1-Eth 1-3,6-dimethyl-2,4(1H,3H)-pyrimidinedione

To a suspension of 3,6-dimethyl-2,4(1H,3H)-pyrimidinedione (2.0 g) in DMF (15 ml) at room temperature was added potassium carbonate (2.1 g). The mixture was stirred for 5 minutes then ethyl iodide (1.2 ml) was added and the mixture stirred for 3 days. The reaction mixture was partitioned between water (500 ml) and ethyl acetate (3×100 ml). The combined organic phase was dried (MgSO$_4$) and evaporated to give the sub-title compound as a colourless oil (2.0 g) (contains ~30 mole % DMF by NMR). δ $^1H_{CDCl3}$ 1.32 (3H, t), 3.33 (3H, s), 4.15 (2H, q), 5.92 (1H, s)

b) 1-Ethyl-6-mercapto-3-methyl-2,4(1H,3H)-pyrimidinedione

Prepared from the product of step a) following the procedure of example 5, step a). δ $^1H_{CDCl3}$ 1.28 (3H, t), 3.32 (3H, s), 4.14 (2H, s), 4.48 (2H, q)

c) Methyl 1-ethyl-1,2,3,4-tetrahydro-3,6-dimethyl-2,4-dioxo-thieno[2,3-d]pyrimidine-5-carboxylate Prepared from the product of step b) following the procedure of example 3, step a). MS(ESI) 283 [M+H]$^+$ d) Methyl 6-(bromomethyl)-1-ethyl-1,2,3,4-tetrahydro-3-methyl-2,4-dioxo-thieno[2,3-d]pyrimidine-5-carboxylate Prepared from the product of step c) following the procedure of example 22, step a).

e) Methyl 6-[4,5-dichloro-2-methyl-1H-imidazol-1-ylmethyl]-1-ethyl-1,2,3,4-tetrahydro-3-methyl-2,4-dioxo-thieno[2,3-d]pyrimidine-5-carboxylate A mixture of the product of step d) (0.25 g), sodium bicarbonate (0.29 g) and 4,5-dichloro-2-methyl-1H-imidazole (0.115 g) in acetonitrile (10 ml) was heated at reflux for 18 hours. The cooled mixture was partitioned between water (50 ml) and dichloromethane (3×50 ml). The combined organic phase was dried (MgSO$_4$) and evaporated to give the sub-title compound as an oil which was used directly in the next step. MS(ESI) 429/431/433 [M−H$^+$]

f) 6-[4,5-dichloro-2-methyl-1H-imidazol-1-ylmethyl]-1-ethyl-i 2,3,4-tetrahydro-3-methyl-2,4-dioxo-thieno[2,3-d]pyrimidine-5-carboxylic acid, sodium salt Prepared from the product of step e) following the procedure of example 1, step f).
MS(ESI) 417/419/421 [M+H]$^+$ g) 6-[4,5-dichloro-2-methyl-1H-imidazol-1-ylmethyl]-1-ethyl-5-[(4S)$_4$-hydroxy-2-isoxazolidinylcarbonyl]-3-methyl-thieno[2,3-d]pyrimidine-2,4(1H,3H)-dione Prepared from the product of step f) using the amine of example 1, step b) following the procedure of example 1, step g). MS(ESI) 488/490/492 [M+H]$^+$. δ $^1H_{DMSO}$ (90° C.*) 1.25 (3H, t), 2.33 (3H, s), 3.22 (3H, s), 2.99 (1H, s), 3.34-3.55 (1H, m), 3.70-4.14 (5H, m), 4.63-4.87 (1H, m), 5.27 (2H, m). (*N.B. Substance exists as a mixture of rotamers therefore NMR complicated at room temperature but simplified at elevated temperature)

EXAMPLE 28i

1-Ethyl-5-[(4S)-4-hydroxy-2-isoxazolidinylcarbonyl]-3-methyl-6(1H-pyrrolo[2,3-b]pyridin-3-ylmethyl)-thieno[2,3-d]pyrimidine-2,4(1H,3H)-dione

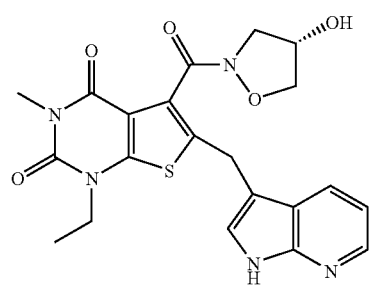

a) 1-Ethyl-1,2,3,4-tetrahydro-3-methyl-2,4-dioxo-6-(1H-pyrrolo[2,3-b]pyridin-3-ylmethyl)-thieno[2,3-d]pyrimidine-5-carboxylic acid, methyl ester The sub-title compound was prepared by the method of example 22 part b, from the product of example 28 part d). δ $^1H_{CDCl3}$ 1.26 (3H, t), 3.49 (3H,s), 3.87 (2H,q), 4.03 (3H,s), 4.28 (2H, s), 7.058 (1H,t), 7.93 (1H,d), 8.32 (1H,d) and 8.89 (1H,s).

b) 1-Ethyl-1,2,3,4-tetrahydro-3-methyl-2,4-dioxo-6-(1H-pyrrolo[2,3-b]pyridin-3-ylmethyl)-thieno[2,3-d]pyrimidine-5-carboxylic acid The sub-title compound was prepared by the method of example 3 part d). MS (ESI) 386 [M+H]+ c) 1-Ethyl-5-[(4S)-4-hydroxy-2-isoxazolidinylcarbonyl]-3-methyl-6-(1H-pyrrolo[2,3-b]pyridin-3-ylmethyl)-thieno[2,3-d]pyrimidine-2,4(1H,3H)-dione Prepared from the product of step b) using the procedure of example 3 part e). The product was purified by reverse phase HPLC eluting with ammonium acetate:acetonitrile (70:30) to give the title compound as an off-white solid. δ $^1H_{D6DMSO}$ 1.12 (3H, m), 3.31 (3H,s), 3.58-4.22 (6H,m), 4.62-4.75 (1H,s), 4.8 (1H,s), 5.5 (1H,s), 6.9-7.03 (1H,m), 7.45 (1H,m), 7.95-8 (1H,m), 8.19 (1H,d), 11.53 (1H,s).

EXAMPLE 28ii

1-Ethyl-5-[(4S)-4-hydroxy-2-isoxazolidinylcarbonyl]-3-methyl-612-propyl-1H-benzimidazol-1-yl methyl]-thieno[2,3-d]pyrimidine-2,4(1H,3H)-dione

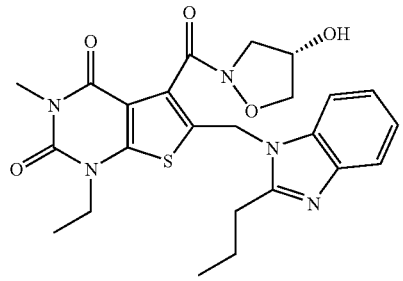

a) Methyl 1-ethyl-1,2,3,4-tetrahydro-3-methyl-2,4-dioxo-6-[2-propyl-1H-benzimidazol-1-yl methyl]-thieno[2,3-d]pyrimidine-5-carboxylate Prepared from the product of example 28 step d) following the procedure of example 13iv, step a). MS(ESI) 441 [M+H]$^+$ b) 1-ethyl-1,2,3,4-tetrahydro-3-methyl-2,4-dioxo-6-[2-propyl-1H-benzimidazol-1-ylmethyl]-thieno[2,3-d]pyrimidine-5-carboxylic acid, sodium salt Prepared from the product of step a) following the procedure of example 1, step f). MS(ESI) 427 [M+H]$^+$(free acid)

c) 1-ethyl-5-[(45-4-hydroxy-2-isoxazolidinylcarbonyl]-3-methyl-6-[2-propyl-1H-benzimidazol-1-ylmethyl]-thieno[2,3-d]pyrimidine-2,4(1H,3H)-dione Prepared from the product of step b) using the amine of example 1, step b) following the procedure of example 1, step g). MS(ESI) 498 [M+H]$^+$. δ $^1H_{DMSO}$ 0.99 (3H, t), 1.12 (3H, t), 1.80 (2H, sextet), 2.88 (2H, t), 3.20 and 3.21 (3H, s), 3.58 (1H, d), 3.70-4.15 (5H, m), 4.63 and 4.81 (1H, t), 5.46-5.70 (3H, m), 7.15-7.22 (2H, m), 7.54-7.69 (2H, m).

EXAMPLE 28iii

1-Ethyl-5-[(4S)-4-hydroxy-2-isoxazolidinylcarbonyl]-3-methyl-6-[2-oxo-3(2H)-benzothiazolylmethyl]-thieno[2,3-d]pyrimidine-2,4(1H,3H)-dione

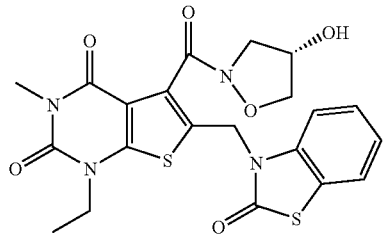

a) Methyl 1-ethyl-1,2,3,4-tetrahydro-3-methyl-2,4-dioxo-6-[2-oxo-3(2H)-benzothiazolylmethyl]-thieno[2,3-d]pyrimidine-5-carboxylate Prepared from the product of example 28 step d) following the procedure of example 13xviii, step a). MS(ESI) 432 [M+H]$^+$ b) 1-ethyl-1,2,3,4-tetrahydro-3-methyl-2,4-dioxo-6-[2-oxo-3(2H)-benzothiazolylmethyl]-thieno[2,3-d]pyrimidine-5-carboxylic acid, sodium salt Prepared from the product of step a) following the procedure of example 1, step 1). MS(ESI) 418 [M+H]$^+$(free acid)

c) 1-ethyl-5-[(4S)-4-hydroxy-2-isoxazolidinylcarbonyl]-3-methyl-6-[2-oxo-3(2H)-benzothiazolylmethyl]thieno[2,3-d]pyrimidine-2,4(1H,3H)-dione Prepared from the product of step b) using the amine of example 1, step b) following the procedure of example 1, step g). MS(ESI) 489 [M+H]$^+$. δ $^1H_{DMSO}$ 1.19 (3H, t), 3.19 and 3.20 (3H, s), 3.52-4.00 (6H, m), 4.56-4.82 (1H, m), 5.09-5.40 (3H, m), 7.19-7.25 (1H, m), 7.33-7.48 (2H, m), 7.67-7.72 (1H, m).

EXAMPLE 28iv

1-Ethyl-5-[(4S)-4-hydroxy-2-isoxazolidinylcarbonyl]-3-methyl-6-[2-methyl-1H-pyrrolo[2,3-b]pyridin-3-ylmethyl]thieno[2,3-d]pyrimidine-2,4(1H,3H)-dione

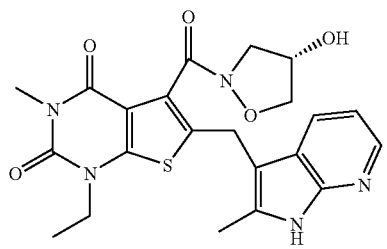

a) Methyl 1-ethyl-1,2,3,4-tetrahydro-3-methyl-6-[2-methyl-1H-pyrrolo[2,3-b]pyridin-3-ylmethyl]-2,4-dioxo-thieno[2,3-d]pyrimidine-5-carboxylate Prepared from the product of example 28 step d) following the procedure of example 14iii, step a). MS(ESI) 399 [M+H]$^+$ b) 1-ethyl-1,2,3,4-tetrahydro-3-methyl-6-[2-methyl-1H-pyrrolo[2,3-b]pyridin-3-ylmethyl]-2,4-dioxo-thieno[2,3-d]pyrimidine-5-carboxylic acid, sodium salt Prepared from the product of step a) following the procedure of example 1, step f). Used directly in next step.

c) 1-ethyl-5-[(4S)-4-hydroxy-2-isoxazolidinylcarbonyl]-3-methyl-6-[2-methyl-1H-pyrrolo[2,3-b]pyridin-3-ylmethyl]-thieno[2,3-d]pyrimidine-2,4(1H,3H)-dione Prepared from the product of step b) using the amine of example 1, step b) following the procedure of example 1, step g). MS(ESI) 470 [M+H]$^+$. δ $^1H_{DMSO}$ 1.10-1.16 (3H, m), 2.40 (3H, s), 3.19-3.20 (3H, m), 3.50-4.83 (10H, m), 6.94-6.99 (1H, m), 7.78-7.86 (1H, m), 8.09 (1H, dd), 11.46 (1H, s).

EXAMPLE 28v

1-Ethyl-5-[(4S)-4-hydroxy-2-isoxazolidinylcarbonyl]-3-methyl-6-[5-cyano-1H-indol-1-ylmethyl]-thieno[2,3-d]pyrimidine-2,4(1H,3H)-dione

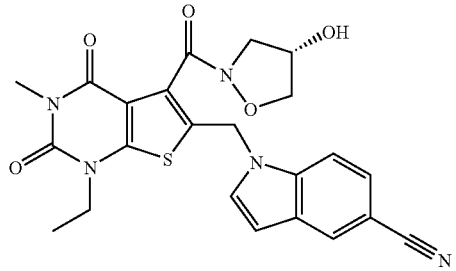

a) 6-[5-cyano-1H-indol-1-ylmethyl]-1-ethyl-1,2,3,4-tetrahydro-3-methyl-24-dioxothieno[2,3-d]pyrimidine-5-carboxylic acid, methyl ester Prepared using the product of example 28 part d) by the method of example 13 xvii) part a) MS(ESI) 421 [M+H]

b) 1-[1-Ethyl-1,2,3,4-tetrahydro-5-[(4S)-4-hydroxy-2-isoxazolidinylcarbonyl]-3-methyl-2,4-dioxothieno[2,3-d]pyrimidin-6-ylmethyl]-1H-indole-5-carbonitrile Prepared using the product of part a) by the methods of example 13 xvii part b) and part c) to give the title compound. δ $^1H_{DMSO}$ 1.10-1.23 (3H, m), 3.2 (3H, s), 3.8-4.12 (6H, m), 4.62-4.81 (1H, m), 5.5-5.64 (3H, m), 6.68 (1H, d), 7.5-7.9 (1H, m), 7.6-7.65 (1H, m), 7.77-7.84 (1H, m) and 8.1 (1H, s).

EXAMPLE 29i

5-[(4S)-4-Hydroxyisoxazolidin-2-ylcarbonyl]-1-(isobutyl)-6-[1-isopropyl-3,5-dimethyl-1H-pyrazol-4-ylmethyl]-3-methylthieno[2,3-d]pyrimidine-2,4(1H,3H)-dione

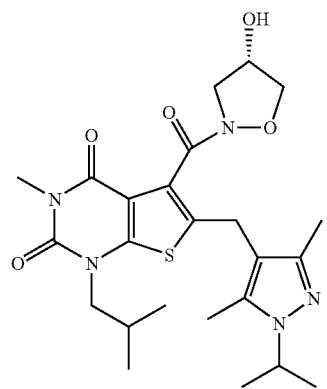

2-Iodopropane (0.1 ml) and potassium carbonate (100 mg) were added to a solution of 6-[(3,5-dimethyl-1H-pyrazol-4-yl)methyl]-5-[(4S)-4-hydroxyisoxazolidin-2-ylcarbonyl]-1-(isobutyl)-3-methylthieno[2,3-d]pyrimidine-2,4(1H,3H)-dione (example 11, 100 mg) in dimethylformamide (1 ml) and the mixture stirred at 100° C. After 2 hours, further 2-iodopropane (0.2 ml) and potassium carbonate (200 mg) were added. After a further 16 hours, the mixture was cooled to room temperature, diluted with water (20 ml) and extracted with ethyl acetate (2×20 ml). Combined organic extracts were treated with pyrrolidine (0.1 ml) and after 1 hour were dried over anhydrous magnesium sulphate, filtered and evaporated under reduced pressure. The residue was purified by reverse-phase HPLC with gradient 0.1% aqueous ammonium acetate/acetonitrile elution to give the title compound (58 mg) as a foam. MS (APCI) 504 [M+H]$^+$. δ $^1H_{DMSO}$ 0.87 (6H, d), 1.31 (6H, d), 1.99-2.14 (7H, m), 3.19-3.21 (3H, m), 3.45-4.13 (8H, m), 4.40 (1H, sept), 4.56-4.79 (1H, m), 5.48-5.55 (1H, m).

EXAMPLE 29ii

5-[(4S)-4-Hydroxyisoxazolidin-2-ylcarbonyl]-1-(isobutyl)-3-methyl-6-[5-methyl-3-phenyl-1H-pyrazol-4-ylmethyl]thieno[2,3-d]pyrimidine-2,4(1H,3H)-dione

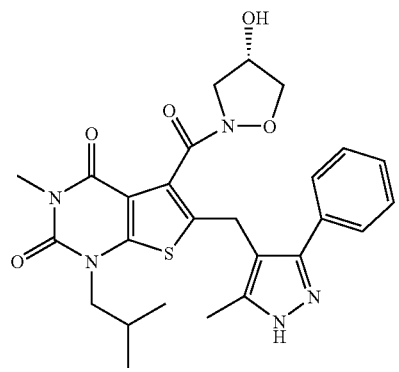

a) Methyl 1-isobutyl-3-methyl-6-[5-methyl-3-phenyl-1H-pyrazol-4-ylmethyl]-2,4-dioxo-1,2,3,4-tetrahydrothieno[2,3-d]pyrimidine-5-carboxylate Zinc (II) acetate (88 mg) was added to a stirred solution of methyl 6-(bromomethyl)-1-isobutyl-3-methyl-2,4-dioxo-1,2,3,4-tetrahydrothieno[2,3-d]pyrimidine-5-carboxylate (185 mg) and 1-benzoylacetone (154 mg) in chloroform (10 ml) and the mixture heated at reflux for 1 hour then cooled to room temperature. Saturated sodium bicarbonate solution (20 ml) was added and the mixture stirred for 30 minutes then filtered and the phases separated. The aqueous phase was extracted with dichloromethane (10 ml). Combined organic extracts were treated with hydrazine hydrate (0.046 ml) and methanol. After 20 hours, the solution was dried over anhydrous magnesium sulphate, filtered and evaporated under reduced pressure to give the sub-title compound (300 mg) contaminated with 5-methyl-3-phenyl-1H-pyrazole. MS(ESI) 467 [M+H]$^+$. δ $^1H_{CDCl_3}$ 0.90 (6H, d), 2.17 (1H, non), 2.27 (3H, s), 3.38 (3H, s), 3.65 (2H, d), 3.94 (3H, s), 4.10 (2H, s), 7.35 (1H, t), 7.40 (2H, t), 7.46 (2H, d).

b) 1-Isobutyl-3-methyl-6-[5-methyl-3-phenyl-1H-pyrazol-4-ylmethyl]-2,4-dioxo-1,2,3,4-tetrahydrothieno[2,3-d]pyrimidine-5-carboxylic acid Sodium hydroxide solution (1M, 0.58 ml) was added to a stirred solution of the product of part a) (300 mg) in tetrahydrofuran (10 ml) and methanol (1 ml). After 48 hours, water (20 ml) was added and the mixture extracted with ether (20 ml). The aqueous phase was acidified to pH 5 by addition of hydrochloric acid (2M) and extracted with ethyl acetate (2×20 ml). Organic extracts were dried over anhydrous magnesium sulphate, filtered and evaporated under reduced pressure to give the sub-title compound (205 mg) as a solid. MS(ESI) 453 [M+H]$^+$. δ $^1H_{DMSO}$ 0.81 (6H, d), 2.03 (1H, non), 2.20 (3H, s), 3.25 (3H, s), 3.62 (2H, d), 4.23 (2H, s), 7.32 (1H, t), 7.39 (2H, t), 7.49 (2H, d).

c) 5-[(4S)-4-Hydroxyisoxazolidin-2-ylcarbonyl]-1-isobutyl-3-methyl-6-[5-methyl-3-phenyl-1H-pyrazol-4-ylmethyl]thieno[2,3-d]pyrimidine-2,4(1H,3H)-dione Diethyl chloridophosphate (0.076 ml) was added to a stirred solution of the product of part b) (200 mg), 1-hydroxybenzotriazole hydrate (81 mg) and triethylamine (0.215 ml) in acetonitrile (2 ml). After 15 minutes, (S)-4-isoxazolidinol hydrochloride [example 1, part b], 61 mg] was added. After a further 24 hours, the mixture was diluted with saturated aqueous sodium bicarbonate solution (10 ml) and extracted with ethyl acetate (2×20 ml). Organic extracts were dried over anhydrous magnesium sulfate, filtered and evaporated under reduced pressure. The residue was purified by column chromatography over silica gel, eluting with ethyl acetate/methanol (25:1) followed by recrystallisation from ethyl acetate/iso-hexane to give the title compound (138 mg). MS (APCI) 524 [M+H]$^+$. δ $^1H_{DMSO}$ 0.82 (6H, d), 2.04 (1H, non), 2.20 (3H, s, br), 3.30 (3H, s), 3.45-4.15 (8H, m), 4.57-4.80 (1H, m), 5.35-5.55 (1H, m), 7.33 (1H, s, br), 7.40 (2H, s, br), 7.54 (2H, s, br), 12.73 (0.5H, s, br) 12.86 (0.5H, s, br).

EXAMPLE 29iii

5-[(4S)-4-Hydroxyisoxazolidin-2-ylcarbonyl]-1-isobutyl-3-methyl-6-[5-methyl-3-(trifluoromethyl)-1H-pyrazol-4-ylmethyl]thieno[2,3-d]pyrimidine-2,4(1H,3H)-dione

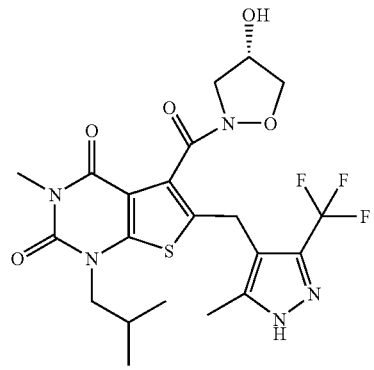

a) Methyl 1-isobutyl-3-methyl-6-[5-methyl-3-(trifluoromethyl)-1H-pyrazol-4-ylmethyl]-2,4-dioxo-1,2,3,4-tetrahydrothieno[2,3-d]pyrimidine-5-carboxylate Prepared from methyl 6-(bromomethyl)-1-isobutyl-3-methyl-2,4-dioxo-1,2,3,4-tetrahydrothieno[2,3-d]pyrimidine-5-carboxylate (300 mg) and 1,1,1-trifluoroacetylacetonate following the procedure of example 29(ii), part a). Crude product was purified by column chromatography over silica, eluting with ethyl acetate/iso-hexane (2:3) to give the sub-title compound (130 mg). MS(ES) 459 [M+H]$^+$. δ $^1H_{DMSO}$ 0.94 (6H, d), 2.22 (1H, non), 2.26 (3H, s), 3.39 (3H, s), 3.69 (2H, d), 3.96 (3H, s), 4.08 (2H, s), 10.29 (1H, s, br).

b) 1-Isobutyl-3-methyl-6-[5-methyl-3-(trifluoromethyl)-1H-pyrazol-4-ylmethyl]-2,4-dioxo-1,2,3,4-tetrahydrothieno[2,3-d]pyrimidine-5-carboxylic acid Prepared from the product of part a) following the procedure of example 29(ii), part b) to give the sub-title compound as a solid. MS(ESI) 445 [M+H]$^+$. δ $^1H_{DMSO}$ 0.86 (6H, d), 2.09 (1H, non), 2.21 (3H, s), 3.26 (3H, s), 3.67 (2H, d), 4.20 (2H, s), 13.43 (1H, s), 14.20 (1H, s, br).

c) 5-[(4S)-4-Hydroxyisoxazolidin-2-ylcarbonyl]-1-isobutyl-3-methyl-6-[5-methyl-3-(trifluoromethyl)-1H-pyrazol-4-ylmethyl]thieno[2,3-d]pyrimidine-2,4(1H,3H)-dione Prepared from the product of part b) following the procedure of example 29(ii), part c) to give the title compound as a solid. MS (APCI) 516 [M+H]$^+$. δ $^1H_{DMSO}$ 0.87 (6H, d), 2.11 (1H, non), 2.18 (3H, s), 3.20 (3H, s), 3.50-4.10 (8H, m), 4.55-4.78 (1H, m).

EXAMPLE 29iv

5-[(4S)-4-Hydroxyisoxazolidin-2-ylcarbonyl]-1-isobutyl-6-[3-isopropyl-5-methyl-1H-pyrazol-4-ylmethyl]-3-methylthieno[2,3-d]pyrimidine-2,4(1H,3H)-dione.

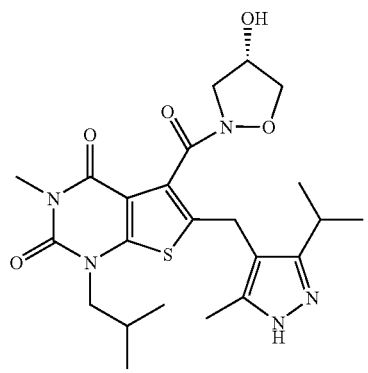

a) 1-Isobutyl-6-[3-isopropyl-5-methyl-1H-pyrazol-4-ylmethyl]-3-methyl-2,4-dioxo-1,2,3,4-tetrahydrothieno[2,3-d]pyrimidine-5-carboxylic acid Prepared from methyl 6-(bromomethyl)-1-isobutyl-3-methyl-2,4-dioxo-1,2,3,4-tetrahydrothieno[2,3-d]pyrimidine-5-carboxylate (450 mg) and 5-methylhexane-2,4-dione following the procedure of example 29(iii), part a), followed by ester hydrolysis following the procedure of example 29(ii) part b) to give the sub-title compound (285 mg) as a solid. MS(ESI) 419 [M+H]⁺. δ ¹H$_{DMSO}$ 0.85 (6H, d), 1.13 (6H, d), 2.07 (3H, s), 2.09 (1H, non.), 2.88 (1H, sept.), 3.26 (3H, s), 3.66 (2H, d), 4.04 (2H, s).

b) 5-[(4S)-4-hydroxyisoxazolidin-2-ylcarbonyl]-1-isobutyl-6-[3-isopropyl-5-methyl-1H-pyrazol-4-ylmethyl]-3-methylthieno[2,3-d]pyrimidine-2,4(1H,3H)-dione Prepared from the product of part a) (281 mg) following the procedure of example 29(ii), part c). Crude product was purified by reverse-phase HPLC with gradient 0.1% aqueous ammonium acetate/acetonitrile elution, then by trituration with ether to give the title compound (170 mg) as a solid. MS (APCI) 490 [M+H]⁺. δ ¹H$_{DMSO}$ 0.86 (6H, d), 1.08-1.18 (6H, m), 2.02-2.17 (4H, m), 2.80-2.98 (1H, m), 3.19-3.21 (3H, m), 3.48-4.12 (8H, m), 4.58-4.78 (1H, d), 5.51 (1H, d), 12.15 (1H, s, br).

EXAMPLE 29(v)

6-[3,5-Dimethyl-1-phenyl-1H-pyrazol-4-ylmethyl]-5-(4)hydroxyisoxazolidin-2-ylcarbonyl-1-isobutyl-3-methylthieno[2,3-d]pyrimidine-2,4(1H,3H)-dione.

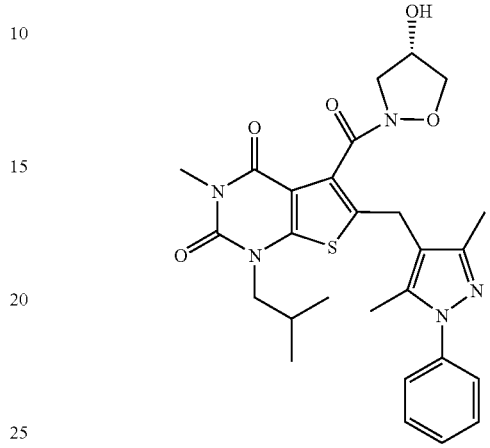

a) Methyl 6-[3,5-dimethyl-1-phenyl-1H-pyrazol-4-ylmethyl]-1-isobutyl-3-methyl-2,4-dioxo-1,2,3,4-tetrahydrothieno[2,3-d]pyrimidine-5-carboxylate Prepared from methyl 6-(bromomethyl)-1-isobutyl-3-methyl-2,4-dioxo-1,2,3,4-tetrahydrothieno[2,3-d]pyrimidine-5-carboxylate (500 mg), zinc acetylacetonate hydrate and phenyl hydrazine following the procedure of example 26, part a). Crude product was purified by column chromatography over silica, eluting with ethyl acetate/iso-hexane (2:3) to give the sub-title compound (555 mg) as a solid. MS(ESI) 481 [M+H]⁺. δ ¹H$_{DMSO}$ 0.95 (6H, d), 2.24 (3H, s), 2.27 (3H, s), 2.20-2.30 (1H, m), 3.39 (3H, s), 3.71 (2H, d), 3.95 (3H, s), 3.96 (2H, s), 7.36-7.50 (5H, m).

b) 6-[3,5-Dimethyl-1-phenyl-1H-pyrazol-4-ylmethyl]-1-isobutyl-3-methyl-2,4-dioxo-1,2,3,4-tetrahydrothieno[23-d]pyrimidine-5-carboxylic acid sodium salt Prepared from the product of part a) following the procedure of example 1 part f) to give the sub-title compound as a solid. MS(ESI) 467 [M+H-Na]⁺. δ ¹H DMSO 0.87 (6H, d), 2.17 (3H, s), 2.10-2.22 (1H, m), 2.17 (3H, s), 3.20 (3H, s), 3.65 (2H, d), 3.84 (2H, s), 7.34-7.39 (1H, m), 7.46-7.51 (4H, m).

c) 6-[3,5-Dimethyl-1-phenyl-1H-pyrazol-4-ylmethyl]-5-[(4S)-4-hydroxyisoxazolidin-2-ylcarbonyl]-1-1-isobutyl-3-methylthieno[2,3-d]pyrimidine-2,4(1H,3H)-dione Prepared from the product of part b) following the procedure of example 29(ii), part c) to give the title compound as a solid. MS (APCI) 538 [M+H]⁺ δ ¹H$_{DMSO}$ 0.89 (6H, d), 0.21-0.22 (4H, m), 2.25 (3H, s), 3.20-3.22 (3H, m), 3.45-4.15 (8H, m), 4.55-4.80 (1H, m), 5.35-5.55 (1H, m), 7.37-7.40 (1H, m), 7.44-7.54 (4H, m).

EXAMPLE 29(vi)

6-[3,5-Dimethyl-1-phenyl-1H-pyrazol-4-ylmethyl]-5-[(4S)-4-hydroxyisoxazolidin-2-ylcarbonyl]-3-methyl-1-propylthieno[2,3-d]pyrimidine-2,4(1H,3H)-dione

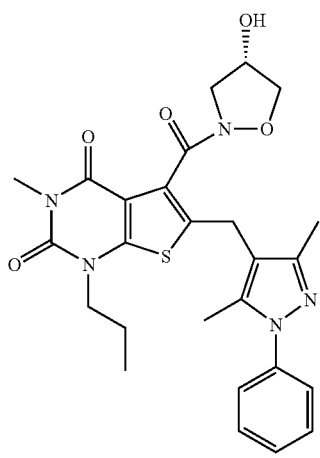

A solution of 6-(bromomethyl)-3-methyl-1-propyl-2,4-dioxo-1,2,3,4-tetrahydrothieno[2,3-d]pyrimidine-5-carboxylic acid (500 mg) and zinc acetylacetonate hydrate (389 mg) in chloroform (10 ml) was stirred at reflux for 1 hour then cooled to room temperature. Water (10 ml) and phenyl hydrazine (0.27 ml) were added, the mixture stirred for 3 days and the phases separated. The aqueous phase was extracted with dichloromethane (2×10 ml). Organic extracts were dried over anhydrous magnesium sulphate, filtered and evaporated under reduced pressure. The residue was dissolved in acetonitrile (5 ml) and treated with 1-hydroxybenzotriazole (173 mg), triethylamine (0.63 ml) and diethyl chloridophosphate (0.22 ml). The mixture was stirred for 1 hour then (S)-4-isoxazolidinol hydrochloride [example 1, part b), 173 mg], was added. After a farther 24 hours, the mixture was evaporated under reduced pressure and the residue purified by reverse-phase HPLC with gradient 0.1% aqueous ammonium acetate/acetonitrile elution. The product was further purified by column chromatography over silica, eluting with ethyl acetate/methanol (49:1) to give the title compound (150 mg) as a foam. MS (APCI) 524 [M+H]$^+$. δ $^1H_{DMSO}$ 0.89 (3H, t), 1.67 (2H, sex), 2.16 (3H, s), 2.26 (3H, s), 3.20-3.22 (3H, m), 3.45-3.60 (1H, m), 3.71-4.15 (7H, m), 4.57-4.80 (1H, m), 5.46-5.57 (1H, m), 7.37-7.40 (1H, m), 7.44-7.54 (4H, m).

EXAMPLE 30

6-(1H-1,2,3-Benzotriazol-1-ylmethyl)-5-[(4S)-4-hydroxyisoxazolidinylcarbonyl]-3-methyl-1-(isopropyl-thieno[2,3-d]pyrimidine-2,4(1H,3H)dione

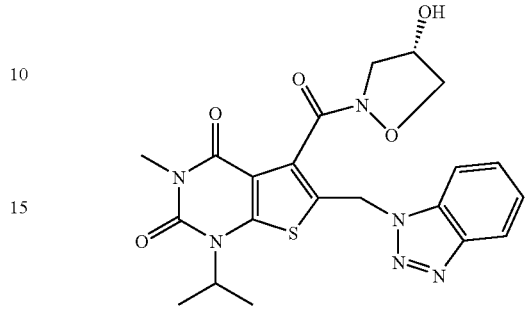

a) 6-(1H-1,2,3-benzotriazol-1-ylmethyl)-1,2,3,4-tetrahydro-3-methyl-1-(isopropyl)-2,4-dioxothieno[2,3-d]pyrimidine-5-carboxylic acid, methyl ester To a solution of benzotriazole (0.19 g) in dry tetrahydrofuran under nitrogen, sodium hydride (0.06 g, 60% suspension) was added. After 10 minutes, the product from example 8 part c) (0.6 g) in dry tetrahydrofuran was added dropwise. The reaction mixture was stirred at room temperature overnight. Water was added and the reaction mixture was extracted with ethyl acetate. The organics were washed with brine, dried over magnesium sulfate then concentrated in vacuo. The residue obtained was purified by silica chromatography eluting with 30% then 40% isohexane in ethyl acetate to give the title compound as a white foam (0.32 g). δ $^1H_{CDCl3}$ 1.50-1.52 (6H, d), 3.35 (3H, s), 4.05 (3H, s), 4.6 (1H, bs), 6.01 (2H, s), 7.4 (1H, m), 7.51 (1H, m), 7.75 (1H, m), 8.07 (1H, m).

b) 6-(1H-1,2,3-benzotriazol-1-ylmethyl)-1,2,3,4-tetrahydro-3-methyl-1-(isopropyl)-2,4-dioxothieno[2,3-d]pyrimidine-5-carboxylic acid Sodium hydroxide (1.5 ml, 1M) was added to a solution of the productd of example 30 a) in tetrahydrofuran under nitrogen. Then about 1 ml of methanol were added to solubilize the reaction mixture. The reaction mixture was stirred at room temperature for 5 h. Hydrochloric acid (0.7 ml, 2M) was added and the reaction mixture was vacuued down to dryness to give the title compound.

c) 6-(1H-1,2,3-benzotriazol-1-ylmethyl)-5-[(40-4-hydroxyisoxazolidinylcarbonyl]-3-methyl-1-(isopropyl)-thieno[2,3-d]pyrimidine-2,4(1H,3H)-dione Hydroxybenzotriazole (0.23 g), (4S)-4-hydroxyisoxazolidine hydrochloride (described in example 1 part b)) (0.16 g) and triethylamine (0.22 ml) were added to a solution of the product of example 30 b) in dichloromethane under nitrogen. After 10 min, EDCI (0.29 g) was added. The reaction mixture was stirred at room temperature overnight. Water was added and the reaction mixture was extracted with dichloromethane. The organics were washed with brine, dried over magnesium sulphate and concentrated in vacuo. The residue was first purified by silica chromatography eluting with ethyl acetate then by reverse phase HPLC to give the title compound as a white foam. MS (APCI) (M$^+$+H) 471.1450. δ $^1H_{DMSO}$ 1.41-1.45 (6H, m), 3.17 (3H, s), 3.36-4.13 (4H, range of m), 4.4 (1H, bs), 4.8 (1H, 2m), 5.5 (1H, m), 6.02-6.15 (2H, m), 7.4-7.44 (1H, m), 7.54-7.59 (1H, m), 7.91-7.95 (1H, m), 8.05-8.07 (1H, d).

EXAMPLE 31

5-[(4S)-4-Hydroxyisoxazolidinylcarbonyl]-3-methyl-1-(isopropyl)-6-[(2-oxothiazolo[5,4 b]pyridin-1(2H)-yl)methyl]-thieno[2,3-d]pyrimidine-2,4(1H 3H)-dione

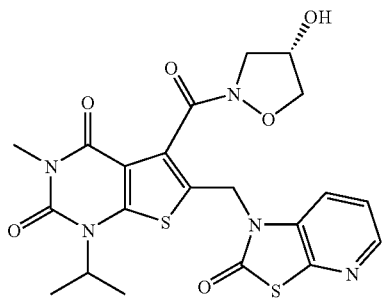

a) 1,2,3,4-tetrahydro-3-methyl-1-(isopropyl)-2,4-dioxo-6-[2-oxothiazolo[5,4-b]pyridin-1(2H)-ylmethyl]-thieno[2,3-d]pyrimidine-5-carboxylic acid, methyl ester Prepared using the procedure described in example 30 a) from [1,3]thiazolo[5,4-b]pyridine-2(1H)-one (0.24 g) (described in example 13xiii) part c)) and the product from example 8 part c) (0.6 g). The residue was triturated with ether then filtered to give the sub-title compound. δ $^1H_{CDCl3}$ 1.57-1.59 (6H, d), 3.36 (3H, s), 4 (3H, s), 4.5 (1H, bs), 5.3 (2H, s), 7.24-7.28 (1H, m), 7.73-7.76 (1H, d), 8.30-8.32 (1H, d).

b) 1,2,3,4-tetrahydro-3-methyl-1-(isopropyl)-2,4-dioxo-6-[2-oxothiazolo[5,4-b]pyridin-1(2H)-ylmethyl]-thieno[2,3-d]pyrimidine-5-carboxylic Sodium hydroxide (0.78 ml, 1M) was added to a solution of the product of example 31 part a) (0.35 g) in tetrahydrofuran under nitrogen. Then 1 ml of methanol was added to solubilize the mixture and the reaction mixture was stirred at room temperature for 48 h. The precipitate formed was filtered, washed with tetrahydrofuran then ether to give the sub-title compound (0.18 g). MS (ES)(M$^+$+H) 433 c) 5-[(4S)$_4$—Hydroxyisoxazolidinylcarbonyl]-3-methyl-1-(isopropyl)-6-[2-oxothiazolo[5.4-b]pyridin-1(2H)-ylmethyl]-thieno[2,3-d]pyrimidine-2,4(1H,3H)-dione Hydroxybenzotriazole (0.12 g) was added to a suspension of the product of example 31 b) in tetrahydrofuran under nitrogen. After 10 min, EDCI (0.15 g) was added and after another 40 min, (4S)-4-hydroxyisoxazolidine hydrochloride (0.06 g) and triethylamine (0.07 ml) were added. The reaction mixture was stirred at room temperature overnight. Water was added and the mixture was extracted with dichloromethane. The organics were washed with brine, dried over magnesium sulfate then concentrated in vacuo. The residue was purified by silica chromatography eluting with 5% methanol in dichloromethane to give the title compound as a white foam. MS (APCI) (M$^+$+H) 504.0914.δ $^1H_{D6DMSO}$ 1.45-1.48 (6H, m), 3.16 (3H, s), 3.52-4.1 (4H, range of m), 4.4 (1H, bs), 4.6-4.8 (1H, range of m), 5.11-5.57 (3H, m), 7.4-7.47 (1H, m), 7.79-7.81 (1H, d), 8.30-8.31 (1H, d).

EXAMPLE 32

6-[2,3-Dihydro-2-oxo-1H-benzimidazol-1-ylmethyl]-5-[(4S)-4-hydroxyisoxazolidinylcarbonyl]-3-methyl-1-(isopropyl)-thieno[2,3-d]pyrimidine-2,4(1H,3H)-dione

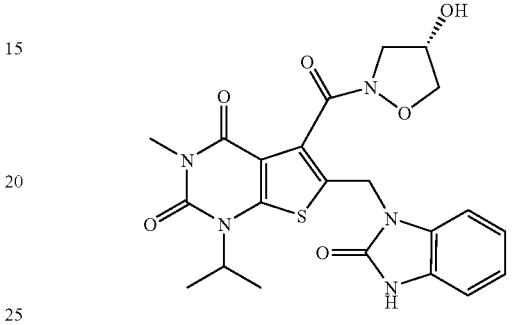

a) 1,2,3,4-Tetrahydro-3-methyl-1-(isopropyl)-6-[2-(methylthio-1H-benzimidazol-1-ylmethyl]-2,4-dioxo-thieno[2,3-d]pyrimidine-5-carboxylic acid, methyl ester Prepared using the procedure described in example 3 part c) from the product of example 8 part c) and 2-methylmercaptobenzimidazole to give the title compound as a pale yellow solid after purification by silica chromatography eluting with isohexane/ethyl acetate (1/1).

MS (ES)(M$^+$+H) 459.δ $^1H_{D6DMSO}$ 1.40-1.42 (6H, d), 2.73 (3H, s), 3.16 (3H, s), 3.80 (3H, s), 4.3 (1H, bs), 5.56 (2H, s), 7.15-7.23 (2H.m), 7.54-7.58 (2H, m).

b) 1,2,3,4-Tetrahydro-3-methyl-1-(isopropyl)-6-[2-(methylsulfonyl)-1H-benzimidazol-1-ylmethyl]-2,4-dioxo-thieno[2,3-d]pyrimidine-5-carboxylic acid methyl ester mCPBA (1.2 g) was added to a solution of the product of example 31 part a)(0.64 g) in dichloromethane. The reaction mixture was stirred at room temperature for 2 h. The reaction mixture was washed with 10% sodium metabisulphite solution (40 ml), sodium hydrogenocarbonate then brine. The organics were dried over magnesium sulfate then concentrated under vacuum to give the sub-title compound. MS(ES)(M$^+$+H) 490.8 c) 6-[2,3-Dihydro-2-oxo-1H-benzimidazol-1-ylmethyl]-1,2,3,4-tetrahydro-3-methyl-1-(isopropyl)-2,4-dioxo-thieno[2,3-d]pyrimidine-5-carboxylic acid Sodium hydrogenocarbonate (0.55 g) was added to a suspension of the product from example 32 part b) (0.54 g) in water. The reaction mixture was heated at reflux for 17 h. The reaction mixture was washed with ethyl acetate and the aqueous layer was freezed dried to give the sub-title compound (0.7 g). MS(ES)(M$^+$+H) 415 d) 6-[2,3-Dihydro-2-oxo-1H-benzimidazol-1-ylm-ethyl]-5-[(4-4-hydroxyisoxazolidinylcarbonyl]-3-methyl-1-(isopropyl)-thieno[2,3-d]pyrimidine-2,4(1H,3H)-dione Prepared using the procedure described in example 31 part c) from the product of example 32 part c) to give the title compound after purification by silica chromatography eluting with 0% then 1% methanol in ethyl acetate followed by a reverse phase HPLC purification eluting with 0.1% ammonium acetate aqueous:acetonitrile (95:5 to 5:95). MS(APCI) (M$^+$+H) (486.1469) δ $^1$H$_{D6DMSO}$ 300 Mhz) 1.44-1.45 (6H, m), 3.16 (3H, s), 3.5-4.5 (5H, range of m), 4.6-5.2 (3H, range of m), 5.5-5.57 (1H, 2m), 6.99 (3H, s), 7.2 (1H,m).

EXAMPLE 33

6-[5,6-Difluoro-2,3-dihydro-2-oxo-1H-benzimidazol-1-ylmethyl]-5-[(4S)-4-hydroxy-2-isoxazolidinylcarbonyl]-3-methyl-1-(isobutyl)thieno[2,3-d]pyrimidine-2,4(1H,3H)-dione

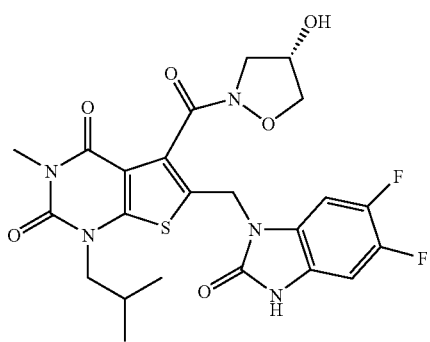

a) 5,6-Difluoro-2-mercaptobenzimiazole

A stirred suspension of 3,4-difluoro-6-nitroaniline(2 g) and 5% palladium on charcoal (100 mg) in ethanol (30 ml) was hydrogenated at 5 bar for 24 h. The mixture was filtered through celite and concentrated in vacuo to give a solid which was dissolved in DMF (20 ml) and treated with carbon disulfide (10 ml). The solution was stirred for 5 h at ambient temperature. The solution was poured onto water and the resultant mixture was extracted with ethyl acetate (×3). The combined organic extracts were dried (MgSO4) and concentrated in vacuo to give a dark red solid (2.45 g). δ $^1$H$_{D6DMSO}$ 7.6-7.62 (2H, m), 8.3 (1H, s, br), 13 (s, 1H).

b) 5,6-Difluoro-2-(methylthio)benzimidazole

A stirred suspension of 5,6-Difluoro-2-mercaptobenzimiazole (2.4 g) and potassium carbonate (1.78 g) in acetone was treated with methyl iodide (0.8 ml) and stirred for 2 h. The reaction was evaporated to dryness and the residue suspended in water (300 ml). The mixture was extracted with ethyl acetate(×3). The combined organic extracts were dried (MgSO4) and evaporated. The residue was chromatographed (SiO$_2$/2:8 ethyl acetate-isohexane) to afford the sub-title compound (1.95 g). MS (APCI) 215 [M+H]$^+$ c) 6-[5,6-Difluoro-2-oxo-2,3-dihydro-1H-benzimi-dazol-1-ylmethyl-5-F(4S)-4-hydroxyisoxazolidin-2-ylcarbonyl]-1-isobutyl-3-methylthieno[2,3-d]pyrimi-dine-2,4(1H,3H)-dione m-CPBA was added to dichloromethane and the reaction mixture was stirred for 1 h. The reaction mixture was poured onto a solution of 10% sodium metabisulfite (160 ml). The two phases were separated and the organic washed with sodium hydrogencarbonate, brine then dried (MgSO4) and concentrated in vacuo to give a yellow foam. The foam was treated with water (5 ml), THF (5 ml) and sodium hydrogencarbonate (0.37 g). The reaction mixture was stirred at reflux for 48 h. A precipitate was formed which was filtered and washed with water to give a white solid. The solid was treated with THF (7 ml), HOBT (0.2 g) and EDCI (0.28 g). The reaction mixture was stirred at reflux for 35 min and then triethylamine (0.24 ml) and (S)-Hydroxyisoxizolidine-.HCl (0.18 g) were added. The reaction mixture was stirred at reflux for 2 days. The residue was chromatographed (SiO$_2$/98:2 ethyl acetate-methanol) to give a yellow solid. This was recrytallised from methanol to afford the title compound as a white crystalline solid (0.18 g). δ $^1$H$_{D6DMSO}$ 0.84 (6H, m), 2.02-2.19 (1H,m), 3.19 (1H,s), 3.74-4.17 (5H,m), 4.6-4.81 (1H,m), 4.97-5.18 (2H,m), 5.7-5.61 (1H, m), 7.02-7.17 (m,1H) and 7.35-7.41 (m,1H).

EXAMPLE 34

5-[(4S)-4-Hydroxyisoxazolidin-2-ylcarbonyl]-6-(imidazo[1,2-a]pyridin-3-ylmethyl)-1-isobutyl-3-methylthieno[2,3-d]pyrimidine-2,4(1H,3H)-dione

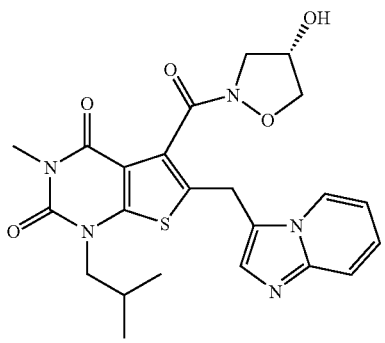

a) Methyl 6-(imidazo[1,2-a]pyridin-3-ylmethyl-1-isobutyl-3-methyl-2,4-dioxo-1,2,3,4-tetrahy-drothieno[2,3-d]pyrimidine-5-carboxylate The product of example 3 part b (1 g), imidazolo[1,2-a]pyridine (0.4 ml), potassium carbonate (0.35 g) and THF (20 ml) were stirred under nitrogen for 1 h. Warer was added to the reaction and extracted with ethyl acetate (×2). The combined organic extracts were dried (MgSO4) and concentrated in vacuo. The residue was chromatographed (SiO$_2$/9:1 ethyl acetate-hexane and the ethyl acetate) to give the sub-title compound as a colourless oil. LCMS(ESI) 4275 [M+H]$^+$ b) 6-(Imidazo[1,2-a]pyridin-3-ylmethyl)-1-isobutyl-3-methyl-2,4-dioxo-1,2,3,4-tetrahydrothieno[2,3-d]pyrimidine-5-carboxylic acid The product of part a was treated with sodium hydroxide (0.75 ml), THF (5 ml) and methanol (0.05 ml) and the resulting solution was stirred for 2 h under nitrogen. The reaction mixture was washed with ethyl acetate. The aqueous phase was concentrated in vacuo to give the subtitle compound (0.13 g).

c) 5-[(4S)-4-Hydroxyisoxazolidin-2-ylcarbonyl]-6-(imidazo[112-a]pyridin-3-ylmethyl)-1-isobutyl-3-methylthieno[2,3-d]pyrimidine-2,4(1H,3H)-dione The product of step b (0.13 g), was dissolved in THF (3 ml). HOBT (0.09 g) was added, followed by EDCI (0.12 g). After stirring for 10 min triethylamine (0.05 ml) and (S)-Hydroxyisoxizolidine.HCl (0.08 g) were added and the reaction mixture was stirred for 16 h. Water (10 ml) and ethylacetate (10 ml) were added. The two phases were separated and the aq layer was re-extracted with ethyl acetate. The combined organic extracts were dried (MgSO4) and concentrated in vacuo. The compound was purified by RPHPLC eluting with ammonium acetate:acetonitrile (80: 20) to afford the title compound as a white solid. LCMS (APCI) 485 [M+H]+

EXAMPLE 35

3-Methyl-6-[2-methylindol-3-ylmethyl]-1-(isobutyl)-5-(tetrahydroisoxazin-2-ylcarbonyl)-thieno [23-d]pyrimidine-2,4(1H,3H)-dione

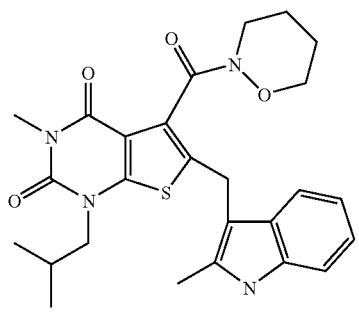

3-Methyl-6-[2-methylindol-3-ylmethyl]-1-(isobutyl)-5-(tetrahydroisoxazin-2-ylcarbonyl)-thieno[2,3-d]pyrimidine-2,4(1H,3H)-dione The title compound was prepared by the method of Example 1 part g) using the product of Example 5 part b) and tetrahydro-1,2-oxazine hydrochloride.
MS (APCI) 495 [M+H]+
δ $^1H_{DMSO, 130°C}$ 0.82 (6H,d); 1.72 (4H,br s); 2.11 (1H, septet); 2.35 (3H,s); 3.25 (3H,s); 3.6 (2H,br d); 3.70 (2H,br s); 3.85 (2H,br s); 4.1 (2H,s); 6.9 (1H,t); 6.95 (1H,t); 7.25 (1H,d); 7.35 (1H,d); 10.4 (1H,br s).

EXAMPLE 36

6-[2-Bromo-4,5-dichloro-1H-imidazol-1-ylmethyl]-5-[(4S)-4-hydroxyisoxazolidinylcarbonyl]-3-methyl-1-(isobutyl)thieno[2,3-d]pyrimidine-2,4(1H,3H)-dione

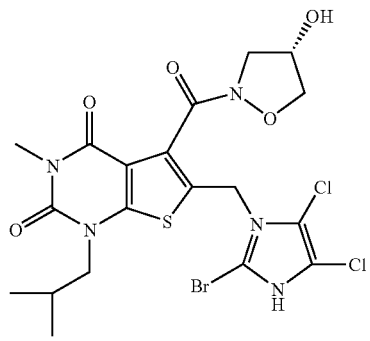

a) 6-[2-bromo-4,5-dichloro-1H-imidazol-1-ylmethyl-1,2,3,4-tetrahydro-3-methyl-1-(isobutyl)-2,4-dioxo-thieno[2,3-d]pyrimidine-5-carboxylic acid, methyl ester The product from example 3 part b) (1 g) was added to a solution of 2-bromo-4,5-dichloroimidazole (0.73 g) and potassium carbonate (1 g) in anhydrous dimethylformamide.

The reaction was stirred at room temperature for 2 days then diluted into water and extracted with ethyl acetate (twice). The organics were dried over magnesium sulfate and concentrated under reduced pressure. The residue was purified by flash silica chromatography eluting with 20% ethyl acetate in isohexane to give the subtitle compound (0.84 g). MS (APCI) 524.9 [M+H]. δ $^1H_{CDCL3}$ 0.96-0.98 (6H,d), 2.2-2.3 (1H,m), 3.39 (3H,s), 3.73-3.75 (2H,d), 4 (3H, s), 5.36 (2H,s)

b) 6-[2-bromo-4,5-dichloro-1H-imidazol-1-ylmethyl]-1,2,3,4-tetrahydro-3-methyl-1-(isobutyl)-2,4-dioxo-thieno[2,3-d]pyrimidine-5-carboxylic acid Sodium hydroxide (2 ml of 1M aqueous solution) followed by methanol (0.5 ml) were added to a solution of the product of step a) (0.85 g) in tetrahydrofuran (7 ml) and stirred at room temperature for 2 hours. The precipitate formed was filtered and washed witl tetrahydrofuran to give the subtitle compound as a white solid (0.81 g). MS (APCI) 510.8 [M+H]

c) 6-[2-Bromo-4,5-dichloro-1H-imidazol-1-ylmethyl]-5-[(4M)-4-hydroxyisoxazolidinylcarbonyl]-3-methyl-1-(isobutyl)-thieno[2,3-d]pyrimidine-2,4(1H,3H)-dione Prepared using the procedure described in example 1 part g) from the product of step b) in example 10 and (4S)-4-hydroxyisoxalidine hydrochloride (product of example 1b) to give the subtitle compound after purification by flash silica chromatography eluting with 2% methanol in dichloromethane. MS (APCI) 581.8 [M+H]. δ $^1H_{DMSO}$ 0.89-0.91 (6H,d), 2.1-2.2 (1H, m), 3.2 (3H, s), 3.64 (5H, m), 4-4.1 (1H, m), 4.6-4.8 (1H, 2m), 5.34 (2H, s), 5.51-5.53 (1H, d)

EXAMPLE 37

5-[(4S)-4-Hydroxyisoxazolidin-2-ylcarbonyl]-3-methyl-1-(isobutyl)-6-[2-(methylthio)-1H-imidazo[4,5-b]pyridin-1-ylmethyl]-thieno[2,3-d]pyrimidine-2,4(1H,3H)-dione

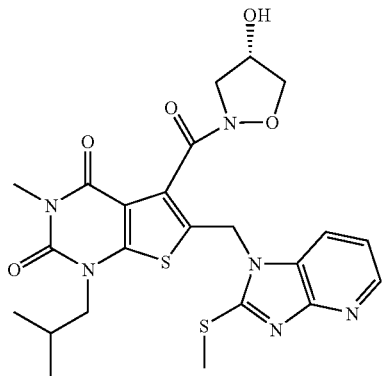

a) 2-(methylthio)-1H-imidazo[4,5-b]pyridine

Potassium ethylxanthate (4.51 g) was added to 2,3-diaminipyridine (2.51 g) in ethanol (25 ml) and water (5 ml). The reaction mixture was refluxed for 24 h then cooled. A precipitate was formed which was filtered, washed with ethanol then ether to give a pale pink solid (3.16 g). Potassium hydroxide (23 ml, 1M) was added to this solid and after 5 min, iodomethane (1.3 ml) was added. The reaction mixture was stirred at room temperature overnight, then extracted with ethyl acetate. The aqueous layer was concentrated in vacuo. The residue was triturated with methanol and the insoluble solid was filtrated. The filtrate was concentrated under vacuum then the residue was triturated with dichloromethane and filtered to give the title-compound as a beige solid (440 mg). MS(ES) 166 [M+H]$^+$. δ $^1H_{DMSO}$ 2.56 (3H, s), 6.68-6.73 (1H, m), 7.44-7.47 (1H, d), 7.84-7.86 (1H, d).

b) 1,2,3,4-tetrahydro-3-methyl-1-(isobutyl)-6-[2-(methylthio)-1H-imidazo[4,5-b]pyridin-1-ylmethyl]-2,4-dioxo-thieno[2,3-d]pyrimidine-5-carboxylic acid, methyl ester Prepared from the product of example 3b (815 mg) and 2-(methylthio)-1H-imidazo[4,5-b]pyridine (example 37 part a)) (342 mg) by the method of example 13vii part a). The crude material was purified by flash silica chromatography eluting with 50% ethyl acetate in isohexane then 3% methanol in dichloromethane to give the title-compound (190 mg) as well as the product of example 22i part a) (40 mg). MS(ES) 474 [M+H]$^+$. δ $^1H_{CDCl3}$ 0.89-0.90 (6H, d), 2.1-2.2 (1H, m), 2.8 (3H, s), 3.4 (3H, s), 3.6 (2H, d), 4.1 (3H, s), 5.82 (2H, s), 6.95-7 (1H, t), 7.85-7.91 (2H, m).

c) Sodium 1,2,3,4-tetrahydro-3-methyl-1-(isobutyl)-6-[2-(methylthio)-1H-imidazo[4,5-b]pyridin-1-ylmethyl]-2,4-dioxo-thieno[2,3-d]pyrimidine-5-carboxylate Sodium hydroxide (0.8 ml, 1M) was added to a solution of the product of example 37 part b) (190 mg) in tetrahydrofuran under nitrogen. Methanol was added to solubilise the solution and the reaction mixture was stirred at room temperature for 3 hours. HCl (0.4 ml, 2M) was added to neutralise the solution and the mixture was concentrated in vacuo to give the title-compound. MS(ES) 460 [M+H]$^+$ d) 5-[(4S)-4-Hydroxyisoxazolidin-2-ylcarbonyl]-3-methyl-1-(isobutyl-6-[2-(methylthio)-1H-imidazo[4,5-b]pyridin-1-ylmethyl]-thieno[2,3-d]pyrimidine-2,4(1H,3H)-dione Prepared from product of example 37 part c) by the method of example 1 part g). The crude material was purified by reverse-phase preparative HPLC eluting with acetonitrile in 0.1% ammonium acetate aqueous from 25% to 95% to give the title-compound as a colourless oil (47 mg). MS(LS) 531.1494 [M+H]$^+$. δ $^1H_{DMSO}$ 0.88-0.90 (6H, m), 2.1-2.2 (1H, m), 2.70 (3H, s), 3.18 (3H, s), 3.6-3.9 (5H, 3m), 4-4.1 (1H, m), 4.6-4.8 (1H, 3m), 5.5-5.9 (3H, m), 7.1 (1H, m), 7.9 (2H, m).

EXAMPLE 37i

5-[(4S)-4-Hydroxyisoxazolidinylcarbonyl]-3-methyl-1-(isobutyl)-6-[2-(methylthio)-3H imidazo[4,5-b]pyridin-3-ylmethyl]-thieno[2,3-d]pyrimidine-2,4(1H,3H)-dione

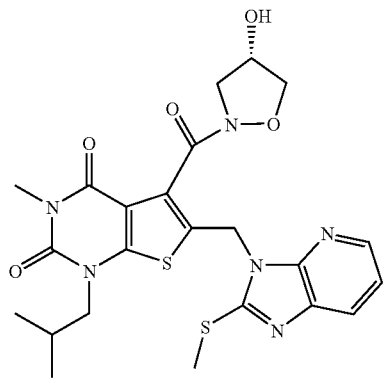

a) 1,2,3,4-tetrahydro-3-methyl-1-(isobutyl)-6-[2-(methylthio)-3H-imidazo[4,5-b]pyridin-3-ylmethyl]-2,4-dioxo- thieno[2,3-d]pyrimidine-5-carboxylic acid, methyl ester Obtained from the reaction of example 37 part b). MS(ES) 474 [M+H]$^+$. δ $^1H_{CDCl3}$ 0.88-0.90 (6H, d), 2.1-2.2 (1H, m), 2.8 (3H, s), 3.38 (3H, s), 3.66-3.68 (2H, d), 4 (3H, s), 5.6 (2H, s), 7.19-7.23 (1H, m), 7.90-7.93 (1H, d), 8.28-8.29 (1H, d).

b) 1,2,3,4-tetrahydro-3-methyl-1-(isobutyl)-6-[2-(methylthio)-3H-imidazo[4,5-b]pyridin-3-ylmethyl]-2,4-dioxo- thieno[2,3-d]pyrimidine-5-carboxylic acid Prepared from the product of example 37i part a) (40 mg) by the method of example 22 part c) to give the title-compound. MS(ES) 460 [M+H]$^+$ c) 5-[(4S)₄-hydroxyisoxazolidinylcarbonyl]-3-methyl-1-(isobutyl)-6-[2-(methylthio)-3H-imidazo[4,5-b]pyridin-3-ylmethyl]-thieno[2,3-d]pyrimidine-2,4(1H,3H)-dione Prepared from product of example 37i part b) by the method of example 1 part g). The crude material was purified by flash silica chromatography eluting with 3% methanol in dichloromethane, followed by trituration with isohexane to give the title-compound as a pale yellow solid (10 mg). MS(ES) 531.1583 [M+H]⁺. δ ¹H$_{CDCl_3}$ 0.91-0.93 (6H, d), 2.17-2.26 (1H, m), 2.78-2.8 (3H, d), 3.36 (3H, s), 3.5-4.2 (6H, 3m), 4.6-5 (2H, 3d), 5.43-5.74 (2H, m), 7.19-7.26 (1H, m), 7.9-7.93 (1H, d), 8.26-8.28 (1H, d).

EXAMPLE 38

6-[3,5-Dimethyl-1H-pyrazol-4-ylmethyl]-3-ethyl-5-[(4S)-4-hydroxy-2-isoxazolidinylcarbonyl]-1-(isopropyl)-thieno[2,3-d]pyrimidine-2,4(1H,3H)-dione

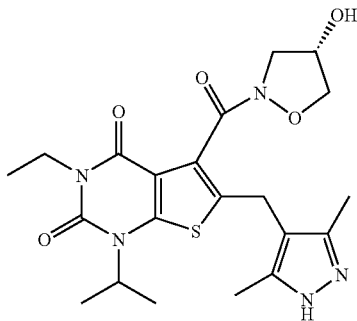

a) 1,2,3,4-tetrahydro-6-methyl-1-(isopropyl)-2,4-dioxo-thieno[2,3-d]pyrimidine-5-carboxylic acid, methyl ester Silver cyanate (13.5 g) suspended in anhydrous toluene (90 ml) under nitrogen was treated dropwise with acetyl chloride (5.34 ml) and stirred vigorously for 30 min. The product of example 8 step a) (23 g) dissolved in anhydrous toluene (15 ml) was added and the mixture was stirred for 72 h. Ether (360 ml) was added and the insoluble material was filtered off and washed with a small volume of ether. The combined organic solutions were washed with saturated sodium bicarbonate solution, dried and evaporated. The residue was treated with a solution of sodium methoxide in methanol (25 wt %, 64 ml) at room temperature for 72 h. The reaction was cooled in ice and treated with trimethylsilyl chloride (50.8 ml) and stirred at room temperature overnight. All volatiles were removed in vacuo and the residue partitioned between water and ethyl acetate. Drying and evaporation of the organic solution left a residue, which was chromatographed (SiO₂/2:1 isohexane-ethyl acetate then 3:2 isohexane-ethyl acetate) to isolate the sub-title compound (12.2 g). MS(ES) 283 [M+H]⁺ b) 3-Ethyl-1,2,3,4-tetrahydro-6-methyl-1-(isopropyl)-2,4-dioxo-thieno[2,3-d]pyrimidine-5-carboxylic acid, methyl ester The product of part a) (0.5 g), potassium carbonate (0.34 g), ethyl iodide (0.17 ml), DMF (5 ml) and acetone (5 ml) were heated at 50 C for 16 h. The reaction mixture was quenched with water (5 ml) and then extracted with ethyl acetate. The organic extracts were dried (MgSO4) and concentrated in vacuo. The residue was chromatographed chromatographed (SiO₂/8:1:1 isohexane-ethyl acetate-dichloromethane to give the sub-title compound as a pale yellow oil.

δ ¹H$_{CDCl_3}$ 1.23 (3H,t), 1.59 (6H,m), 2.4 (3H,s), 3.95 (3H,t), 4.01-4.06 (2H,q), 4.6-4.8 (1H, m).

c) 6-(Bromomethyl-3-ethyl-1,2,3,4-tetrahydro-1-(isopropyl)-2,4-dioxo-thieno[2,3-d]pyrimidine-5-carboxylic acid, methyl ester The subtitle compound was prepared by the method of example 22 part a) using the product of part b). MS(ES) 327 [M+OH–Br]⁺ d) 6-[3,5-Dimethyl-1H-pyrazol-4-ylmethyl]-3-ethyl-1,2,3,4-tetrahydro-1-(isopropyl)-2,4-dioxo-thieno[2,3-d]pyrimidine-5-carboxylic acid, methyl ester The subtitle compound was prepared by the method of example 26 part a) using the product of part c). MS(ES) 334 [M+H]⁺ e) 6-[3,5-Dimethyl-1H-pyrazol-4-ylmethyl]-3-ethyl-5-[(45-4-hydroxy-2-isoxazolidinylcarbonyl]-1-(isopropyl)-thieno[2,3-d]pyrimidine-2,4(1H,3H)-dione The product of part d) (0.6 mmol), diethyl chlorophosphate(0.09 ml), 1-hydroxybenzotriazole(0.08 g), triethylamine(0.1 ml) and acetonitrile (6 ml) were stirred for 30 min. The prodcut of example 1 part b) (0.08 g) was added and the mixture was stirred for 16 h. The reaction was quenched with the addition of potassium carbonate. The reaction mixture was purified SiO₂ chromatography eluting THF:methanol (98:2) to give the a yellow foam, which was furhter purified by reverse phase HPLC to give the sub-title compound as a white solid (30 mg). δ ¹H$_{DMSO}$ 1.06-1.18 (3H,m), 1.41-1.53 (6H,m), 2.1 (6H,s), 3.42-4.18 (7H,m), 4.3-4.47 (1H,s), 4.63-4.8 (1H,m) and 5.5 (1H,m).

EXAMPLE 39

5-[(4S)-4-Hydroxy-2-isoxazolidinylcarbonyl-3-methyl-1-(isobutyl)-6-[2-(trifluoromethyl)phenylmethyl]-thieno[2,3-d]pyrimidine-2,4(1H,3H)-dione

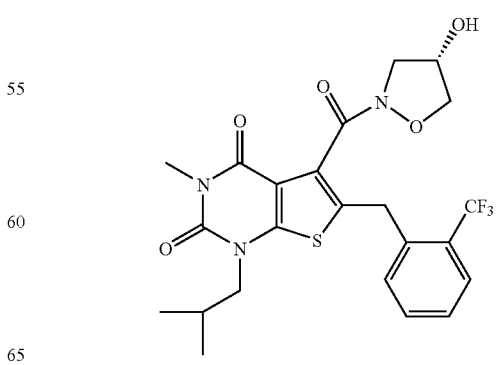

a) 1,2,3,4-Tetrahydro-3-methyl-1-(isobutyl-2,4-di-oxo-6-[2-(trifluoromethyl)phenylmethyl]-thieno[2,3-d]pyrimidine-5-carboxylic acid To a solution of 5-Bromo-3-methyl-1-(isobutyl)-6-[2-(trifluoromethyl)phenylmethyl]-thieno[2,3-d]pyrimidine-2,4(1H,3H)-dione (WO 0183489) in THF (60 ml) was added isopropylmagnesiumcholride(2M solution in THF, 3.35 ml) dropwise at 0 C under nitrogen. After 5 min the mixture was treated with a stram of carbon dioxide for 10 min. The reaction mixture was quenched with water, acidified 2N HCl and extracted into ethyl acetate (×3). The combined organic extracts were washed with dilute HCl, brine, dried ($MgSO_4$) and concentrated in vacuo to give the subtitle compound as a yellow solid (2.48 g). MS(ES) 441 $[M+H]^+$ b) 5-[(4S)-4-Hydroxy-2-isoxazolidinylcarbonyl]-3-methyl-1-(isobutyl)-6-[2-(trifluoromethyl)phenylmethyl]-thieno[2,3-d]pyrimidine-2,4(1H,3H)-dione Prepared by the method of example 1 part g) using the product of part a). MS(APCI) 512 $[M+H]^+$. $\delta\ ^1H_{DMSO}$ 0.8 (6H,m), 2.1 (1H,pentet), 3.2 (3H,m), 3.5-3.8 (4H,m), 4.2 (2H,m), 4.6-4.7 (1H,m), 5.5 (1H,m), 7.5 (2H,m), 7.6 (1H,t) and 7.8 (1H,d).

EXAMPLE 40

5-T(4S)-4-Hydroxy-2-isoxazolidinylcarbonyl]-3-methyl-1-(isobutyl)-6-[2-(methylthio)-1H-imidazol-1-ylmethyl]-thieno[2,3-d]pyrimidine-2,4(1H,3H)-dione

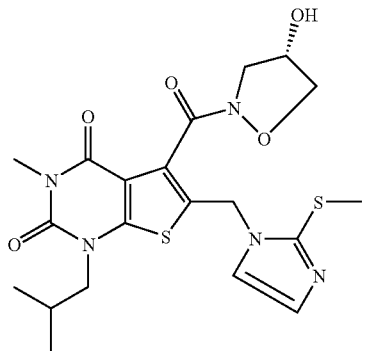

a) 1,2,3,4-tetrahydro-3-methyl-1-(isobutyl)-6-[2-(methylthio)-1H-imidazol-1-ylmethyl]-2,4-dioxo-thieno[2,3-d]pyrimidine-5-carboxylic acid, methyl ester The subtitle compound was prepared by the method of example 13vi part a) using the product of example 3 part b) and 2-methylthioimidazole. MS(ESI) 423 $[M+H]^+$ b) 1,2,3,4-tetrahydro-3-methyl-1-(isobutyl)-6-[2-(methylthio)-1H-imidazol-1-ylmethyl]-2,4-dioxo-thieno[2,3-d]pyrimidine-5-carboxylic acid Prepared by the method of example 3 part d) using the product of part a). MS(ESI) 409 [M+H]+ c) 5-[(45-4 hydroxy-2-isoxazolidinylcarbonyl]-3-methyl-1-(isobutyl)-6-[2-(methylthio)-1H-imidazol-1-ylmethyl]-thieno[2,3-d]pyrimidine-2,4(1H,3H)-dione Prepared by the method of example 3 part e) using the product of part b). MS(APCI) 480 $\delta\ ^1H_{DMSO}$ 0.89-0.91 (6H,m), 2.11-2.18 (1H,m), 2.49-2.52 (3H,m), 3.2-3.21 (3H, m), 3.52-4.1 (6H,m), 4.62-4.78 (1H,m), 5.23-5.25 (2H, m), 5.5-5.58 (1H,m), 6.97 (1H,d) and 7.21-7.23 (1H,m).

The invention claimed is:

1. A compound of formula (1):

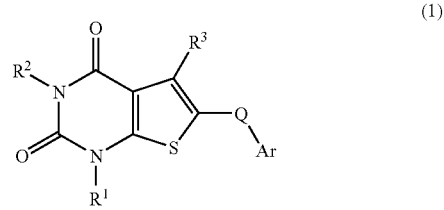

wherein:

$R^1$ and $R^2$ each independently represent a $C_{1-6}$alkyl, $C_{3-6}$alkenyl, $C_{3-6}$cycloalkyl$C_{1-3}$alkyl or $C_{3-6}$cycloalkyl; each of which may be optionally substituted by 1 to 3 halogen atoms;

$R^3$ is isoxazolidin-2-ylcarbonyl or tetrahydroisoxazin-2-ylcarbonyl wherein each ring is optionally substituted by one hydroxy group;

Q is —CO— or —C($R^4$)($R^5$)— (wherein $R^4$ is a hydrogen atom or $C_{1-4}$alkyl and $R^5$ a hydrogen atom or hydroxy group);

Ar is a 5- to 10-membered aromatic ring system wherein up to 4 ring atoms may be heteroatoms independently selected from nitrogen, oxygen and sulphur, the ring system being optionally substituted by one or more substitutes independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —($CH_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from nitrogen, oxygen and sulphur;

p is 1 to 4;

$R^6$ and $R^7$ each independently represent a hydrogen atom, $C_{1-4}$alkanoyl or $C_{1-4}$alkyl, or together with the nitrogen atom to which they are attached form a 5- to 7-membered saturated heterocyclic ring;

$R^8$ and $R^9$ each independently represent a hydrogen atom, $C_{1-4}$alkanoyl or $C_{1-4}$alkyl, or together with the nitrogen atom to which they are attached form a 5- to 7-membered saturated heterocyclic ring;

or a pharmaceutically acceptable salt thereof.

2. A compound according to claim 1 wherein $R^2$ is methyl or ethyl.

3. A compound according to claim 1 wherein $R^1$ is ethyl, n-propyl, 1-methylethyl, 2-methylpropyl, 2,2-dimethylpropyl, cyclopropylmethyl, -trifluoromethyl 2,2,2-trifluoroethyl, 2-chloroethyl, 2-chloropropyl or 3,3,3-trifluoropropyl.

4. A compound according to claim 1 wherein Q is —CO— or —CH$_2$—.

5. A compound according to claim 1 wherein Ar contains at least 1 ring nitrogen.

6. A compound according to claim 1 wherein Ar contains at least 2 ring nitrogens.

7. A compound according to claim 1 wherein Ar is selected from imidazolyl, pyrazolyl, pyrrolyl, isoxazolyl, phenyl, quinolyl, indolyl, benzimidazolyl, indazolyl, benztriazolyl, 2,3-dihydrothiazolyl, 2,3-dihydrobenzoxazolyl, pyrrolo[2,3-b]pyridyl, imidazo[1,2-a]pyridyl, imidazo[4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl, each ring system being optionally substituted according to claim 1.

8. A compound according to claim 1 wherein Ar is substituted by 1, 2 or 3 substituents independently selected from $C_{1-4}$alkyl (optionally substituted by 1 or 2 hydroxy groups), $C_{1-4}$alkoxy, halogen, trihaloalkyl, $C_{1-4}$alkylthio, $C_{2-4}$alkanoyl, oxo, thioxo, cyano and —(CH$_2$)pN(R$^8$)R$^9$ (wherein p is 1 or 2), hydroxy, $C_{1-4}$alkylsulphonyl, carbamoyl, $C_{1-4}$alkylcarbamoyl, di-($C_{1-4}$alkyl)carbamoyl, carboxy, and a 5 or 6 membered aromatic ring containing up to 4 heteroatoms independently selected from nitrogen, oxygen and sulphur.

9. A compound according to claim 1 which is:

(S)-5-[4-hydroxyisoxazolidin-2-ylcarbonyl]-3-methyl-1-(2-methylpropyl)-6-(4-quinolinylmethyl)thieno[2,3-d]pyrimidine-2,4(1H,3H)-dione;

(R) 5-[4-hydroxyisoxazolidin-2-ylcarbonyl]-3-methyl-1-(2-methylpropyl)-6-(4-quinolinylmethyl)thieno[2,3-d]pyrimidine-2,4(1H,3H)-dione;

(S) 6-[4,5-dichloro-2-methyl-1H-imidazol-1-ylmethyl]-5-[4-hydroxy-2-isoxazolidinylcarbonyl]-3-methyl-1-(2-methylpropyl)thieno[2,3-d]pyrimidine-2,4(1H,3H)-dione;

(S) 5-[4-hydroxyisoxazolidin-2-ylcarbonyl]-3-methyl-1-(2-methylpropyl)-6-(4-quinolinylcarbonyl)thieno[2,3-d]pyrimidine-2,4(1H,3H)-dione;

(S) 5-[4-hydroxyisoxazolidin-2-ylcarbonyl]-3-methyl-6-[(2-methyl-1H-indol-3-yl)methyl]-1-(2-methylpropyl)thieno[2,3-d]pyrimidine-2,4(1H,3H)-dione;

(S) 5-[4-hydroxyisoxazolidin-2-ylcarbonyl]-3-methyl-1-(2-methylpropyl)-6-[(1H-pyrrolo[2,3-b]pyridin-3-yl)methyl]thieno[2,3,d]pyrimidine-2,4(1H,3H)-dione;

(S) 5-[4-hydroxyisoxazolidin-2-ylcarbonyl]-3-methyl-6-[(2-methyl-1H-indol-3-yl)carbonyl]-1-(2-methylpropyl)thieno[2,3-d]pyrimidine-2,4(1H,3H)-dione;

(S) 5-[4-hydroxyisoxazolidin-2-ylcarbonyl]-3-methyl-1-(1-methylethyl)-6-(1H-pyrrolo[2,3-b]pyridin-3-ylmethyl)thieno[2,3-d]pyrimidine-2,4(1H,3H)-dione;

(S) 5-[4-hydroxyisoxazolidin-2-ylcarbonyl]-3-methyl-1-propyl-6-(1H-pyrrolo[2,3-b]pyridin-3-ylmethyl)thieno[2,3-d]pyrimidine-2,4(1H,3H)-dione;

(S) 6-[4,5-dichloro-2-oxo-3(2H)-thiazolylmethyl]-5-[4-hydroxyisoxazolidin-2-ylcarbonyl]-3-methyl-1-(2-methylpropyl)-thieno[2,3-d]pyrimidine-2,4(1H,3H)-dione;

(S) 6-[(3,5-dimethyl-1H-pyrazol-4-yl)methyl]-5-{4-hydroxyisoxazolidin-2-ylcarbonyl}-1-isobutyl-3-methylthieno[2,3-d]pyrimidine-2,4(1H,3H)-dione;

(S) 5-{4-hydroxyisoxazolidin-2-ylcarbonyl}-1-isobutyl-3-methyl-6-[1,3,5-trimethyl-1H-pyrazol-4-ylmethyl]thieno[2,3-d]pyrimidine-2,4(1H,3H)-dione;

(R) 6-[(4,5-dichloro-2-methyl-1H-imidazol-1-yl)methyl]-5-[4-hydroxy-isoxazolidin-2-ylcarbonyl]-3-methyl-1-(2-methylpropyl)thieno[2,3-d]pyrimidine-2,4(1H,3H)-dione;

(S) 5-[4-hydroxyisoxazolidin-2-ylcarbonyl]-3-methyl-6-[(2-methyl-1H-benzimidazol-1-yl)methyl]-1-(2-methylpropyl)thieno[2,3-d]pyrimidine-2,4(1H,3H)-dione;

(S) 6-[(2-ethyl-1H-benzimidazol-1-yl)methyl]-5-[4-hydroxyisoxazolidin-2-ylcarbonyl]-3-methyl-1-(2-methylpropyl)thieno[2,3-d]pyrimidine-2,4(1H,3H)-dione;

(S) 5-[4-hydroxyisoxazolidin-2-ylcarbonyl]-3-methyl-1-(2-methylpropyl)-6-[(2-propyl-1H-benzimidazol-1-yl)methyl]thieno[2,3-d]pyrimidine-2,4(1H,3H)-dione;

(S) 5-[4-hydroxyisoxazolidin-2-ylcarbonyl]-3-methyl-1-(2-methylpropyl)-6-[2-(methylthio)-1H-beuzimidazol-1-ylmethyl]thieno[2,3-d]pyrimidine-2,4(1H,3H)-dione;

(S) 5-[4-hydroxyisoxazolidin-2-ylcarbonyl]-6-[2-(hydroxymethyl)-1H-benzimidazol-1-ylmethyl]-3-methyl-1-(2-methylpropyl)thieno[2,3-d]pyrimidine-2,4(1H,3H)-dione;

(S) 5-[4-hydroxyisoxazolidin-2-ylcarbonyl]-3-methyl-6-[2-(methylamino)-1H-benzimidazol-1-ylmethyl]-1-(2-methylpropyl)thieno[2,3-d]pyrimidine-2,4(1H,3H)-dione;

(S) 5-[4-hydroxyisoxazolidin-2-ylcarbonyl]-3-methyl-6-[2-amino-1H-benzimidazol-1-ylmethyl]-1-(2-methylpropyl)thieno[2,3-d]pyrimidine-2,4(1H,3H)-dione;

(S)-5-[4-hydroxy-2-isoxazolidinylcarbonyl]-3-methyl-1-(2-methylpropyl)-6-[2,4,5-trichloro-1H-imidazol-1-ylmethyl]thieno[2,3-d]pyrimidine-2,4(1H,3H)-dione;

(S) 5-[4-hydroxyisoxazolidin-2-ylcarbonyl]-3-methyl-1-(2-methylpropyl)-6-[2-thioxo-3(2H)-benzothiazolymethyl]thieno[2,3-d]pyrimidine-2,4(1H,3H)-dione;

(S) 5-[4-hydroxyisoxazolidin-2-ylcarbonyl]-3-methyl-1-(2-methylpropyl)-6-]4-chloro-2-oxo-3(2H)-thiazolylmethyl]-thieno[2,3-d]pyrimidine-2,4(1H,3H)-dione;

(S) 5-{4-hydroxyisoxazolidin-2-ylcarbonyl}-3-methyl-1-(2-methylpropyl)-6-[2-oxo-1,3-benzoxazol-3(2H)-ylmethyl]thieno[2,3-d]pyrimidine-2,4(1H,3H)-dione;

(S) 5-{4-hydroxyisoxazolidin-2-ylcarbonyl}-3-methyl-1-(2-methylpropyl)-6-[(2-oxo[1,3]thiazolo[5,4-b]pyridin-1-(2H)-yl)methyl]thieno[2,3-d]pyrimidine-2,4(1H,3H)-dione;

(S) 5-[4-hydroxyisoxazolidin-2-ylcarbonyl]-3-methyl-1-(2-methylpropyl)-6-(1H-1,2,3-benzotriazol-1-ylmethyl)-thieno[2,3-d]pyrimidine-2,4(1H,3H)-dione;

(S) 5-[4-hydroxyisoxazolidin-2-ylcarbonyl]-3-methyl-1-(2-methylpropyl)-6-(1H-pyrrolo[2,3-b]pyridin-1-ylmethyl)thieno[2,3-d]pyrimidine-2,4(1H,3H)-dione;

(S) 5-[4-hydroxyisoxazolidin-2-ylcarbonyl]-3-methyl-1-(2-methylpropyl)-6-[2-methyl-1H-pyrrolo[2,3-b]pyridin-1-ylmethyl]thieno[2,3-d]pyrimidine-2,4(1H,3H)-dione;

(S) 1-[1,2,3,4-tetrahydro-5-[4-hydroxyisoxazolidin-2-ylcarbonyl]-3-methyl-1-(2-methylpropyl)-2,4-dioxothieno[2,3-d]pyrimidin-6-ylmethyl]-1H-indole-5-carbonitrile;

(S) 5-{4-hydroxyisoxazolidin-2-ylcarbonyl}-3-methyl-1-(2-methylpropyl)-6-[2-oxo-1,3-benzothiazol-3(2H)-ylmethyl]thieno[2,3-d]pyrimidine-2,4(1H,3H)-dione;

(R) 5-[4-hydroxyisoxazolidin-2-ylcarbonyl]-3-methyl-6-[2-methyl-1H-indol-3-ylmethyl]-1-(2-methylpropyl)thieno[2,3-d]pyrimidine-2,4(1H,3H)-dione;

(S) 5-[4-hydroxyisoxazolidin-2-ylcarbonyl]-3-methyl-6-[7-methyl-1H-indol-3-ylmethyl]-1-(2-methylpropyl)thieno[2,3-d]pyrimidine-2,4(1H,3H)-dione;

(S) 5-[4-hydroxyisoxazolidin-2-ylcarbonyl]-3-methyl-6-[2-(methylamino)-3H-imidazo[4,5-b]pyridin-3-ylmethyl]-1-propyl-thieno[2,3-d]pyrimidine-2,4(1H,3H)-dione;

(S) 6-[4,5-dichloro-2-methyl-1H-imidazol-1-ylmethyl]-5-[4-hydroxy-2-isoxazolidinylcarbonyl]-3-methyl-1-propyl-thieno[2,3-d]pyrimidine-2,4(1H,3H)-dione;

(S) 5-[4-hydroxyisoxazolidin-2-ylcarbonyl]-3-methyl-6-[2-(methylamino)-1H-benzimidazol-1-ylmethyl]-1-(1-methylethyl)thieno[2,3-d]pyrimidine-2,4(1H,3H)-dione;

(S) 6-[4,5-dichloro-2-methyl-1H-imidazol-1-ylmethyl]-5-[4-hydroxy-2-isoxazolidinylcarbonyl]-3-methyl-1-(1-methylethyl)thieno[2,3-d]pyrimidine-5-carboxamide;

(S) 6-[3,5-diethyl-1H-pyrazol-4-ylmethyl]-5-{4-hydroxyisoxazolidin-2-ylcarbonyl}-3-methyl-1-(2-methylpropyl)thieno[2,3-d]pyrimidine-2,4(1H,3H)-dione;

(S) 6-[3-(1,1-dimethylethyl)-5-methyl-1H-pyrazol-4-ylmethyl]-5-{4-hydroxyisoxazolidin-2-ylcarbonyl}-3-methyl-1-(2-methylpropyl)thieno[2,3-d]pyrimidine-2,4(1H,3H)-dione;

(S) 5-[4-hydroxyisoxazolidin-2-ylcarbonyl]-3-methyl-1-(2-methylpropyl)-6-[2-methyl-4-quinolinylmethyl]thieno[2,3-d]pyrimidine-2,4(1H,3H)-dione;

(S) 6-[6-fluoro-4-quinolinylmethyl]-5-{4-hydroxyisoxazolidin-2-ylcarbonyl}-3-methyl-1-(2-methylpropyl)thieno[2,3-d]pyrimidine-2,4(1H,3H)-dione;

(S) 6-[8-fluoro-4-quinolinylmethyl]-5-{4-hydroxyisoxazolidin-2-ylcarbonyl}-3-methyl-1-(2-methylpropyl)-thieno[2,3-d]pyrimidine-2,4(1H,3H)-dione;

(S) 5-{4-hydroxyisoxazolidin-2-ylcarbonyl}-3-methyl-1-(2-methylpropyl)-6-(5-quinolinylmethyl)thieno[2,3-d]pyrimidine-2,4(1H,3H)-dione;

(S) 5-{4-hydroxyisoxazolidin-2-ylcarbonyl}-3-methyl-1-propyl-6-(quinolin-4-ylmethyl)thieno[2,3-d]pyrimidine-2,4(1H,3H)-dione;

(S) 5-{4-hydroxyisoxazolidin-2-ylcarbonyl}-3-methyl-1-(1-methylethyl)-6-(4-quinolinylmethyl)thieno[2,3-d]pyrimidine-2,4(1H,3H)-dione;

(S) 5-[4-hydroxyisoxazolidin-2-ylcarbonyl]-3-methyl-1-(2-methylpropyl)-6-[(2-methyl-1H-pyrrolo[2,3,b]pyridin-3-yl)methyl]thieno[2,3,d]pyrimidine-2,4(1H,3H)-dione;

(R) 5-[4-hydroxyisoxazolidin-2-ylcarbonyl]-3-methyl-1-(2-methylpropyl)-6-[(2-methyl-1H-pyrrolo[2,3,b]pyridin-3-yl)methyl]thieno[2,3,d]pyrimidine-2,4(1H,3H)-dione;

(S)-5-[4-hydroxyisoxazolidin-2-ylcarbonyl]-3-methyl-1-(isobutyl)-6-[2,3-dihydro-6-methyl-3-oxo-pyrazin-2-ylmethyl]-thieno[2,3-d]pyrimidine-2,4(1H,3H)-dione;

(S) 5-[4-hydroxyisoxazolidin-2-ylcarbonyl]-3-methyl-6-[(2-methyl)-1H-pyrrolo[2,3-b]pyridin-3-ylmethyl]-1-propyl-thieno[2,3-d]pyrimidine-2,4(1H,3H)-dione;

5-[(4S)-4-hydroxyisoxazolidin-2-ylcarbonyl]-6-[2-(hydroxymethyl)-1H-benzimidazol-1-ylmethyl]-3-methyl-1-propyl-thieno[2,3-d]pyrimidine-2,4(1H,3H)-dione;

5-[(4S)-4-hydroxyisoxazolidin-2-ylcarbonyl]-3-methyl-1-propyl-6-[2-amino-1H-benzimidazol-1-ylmethyl]-thieno[2,3-d]pyrimidine-2,4(1H,3H)-dione;

(S)-5-[4-hydroxyisoxazolidin-2-ylcarbonyl]-6-[2-(hydroxymethyl)-1H-benzimidazol-1-yl methyl]-3-methyl-1-(isopropyl)thieno[2,3-d]pyrimidine-2,4(1H,3H)-dione;

(S)-5-[4-hydroxyisoxazolidin-2-ylcarbonyl]-3-methyl-1-(isopropyl)-6-[2-amino-1H-benzimidazol-1-ylmethyl]thieno[2,3-d]pyrimidine-2,4(1H,3H)-dione;

(S)-5-[4-hydroxyisoxazolidin-2-ylcarbonyl]-3-methyl-1-(isopropyl)-6-[2-methyl-1H-pyrrolo]2,3-b]pyridin-1-ylmethyl]thieno[2,3-d]pyrimidine-2,4(1H,3H)-dione;

(S) 5-[4-hydroxyisoxazolidin-2-ylcarbonyl]-3-methyl-1-(isopropyl)-6-[2-methyl-1H-pyrrolo[2,3-b]pyridin-3-ylmethyl]thieno[2,3-d]pyrimidine-2,4(1H,3H)-dione;

(S)-6-[4,5-dichloro-2-(hydroxymethyl)-1H-imidazol-1-yl methyl]-5-[4-hydroxyisoxazolidin-2-ylcarbonyl]-3-methyl-1-(isobutyl)-thieno[2,3-d]pyrimidine-2,4(1H,3H)-dione;

(S)-6-[3,5-dimethyl-1H-pyrazol-1-yl methyl]-5-[4-hydroxyisoxazolidin-2-ylcarbonyl]-3-methyl-1-(isobutyl)-thieno[2,3-d]pyrimidine-2,4(1H,3H)-dione;

(S)-6-[2,3-dihydro-2-oxo-1H-benzimidazol-1-ylmethyl]-5-[4-hydroxyisoxazolidin-2-yl carbonyl]-3-methyl-1-(isobutyl)-thieno[2,3-d]pyrimidine-2,4(1H,3H)-dione;

(S) 6-[3,5-dimethyl-1H-pyrazol-4-ylmethyl]-5-[4-hydroxyisoxazolidin-2-ylcarbonyl]-3-methyl-1-propylthieno[2,3-d]pyrimidine-2,4(1H,3H)-dione;

(S) 6-[3,5-dimethyl-1H-pyrazol-4-ylmethyl]-5-[4-hydroxyisoxazolidin-2-ylcarbonyl]-1-isopropyl-3-methylthieno[2,3-d]pyrimidine-2,4(1H,3H)-dione;

(S)-6-[3,5-dimethylisoxazol-4-ylmethyl]-5-[4-hydroxyisoxazolidin-2-ylcarbonyl]-1-(isobutyl)-3-methylthieno[2,3-d]pyrimidine-2,4(1H,3H)-dione;

6-[4,5-dichloro-2-methyl-1H-imidazol-1-ylmethyl]-1-ethyl-5-[(4S)-4-hydroxy-2-isoxazolidinylcarbonyl]-3-methyl-thieno[2,3-d]pyrimidine-2,4(1H,3H)-dione;

1-ethyl-5-[(4S)-4-hydroxy-2-isoxazolidinylcarbonyl]-3-methyl-6-(1H-pyrrolo[2,3-b]pyridin-3-ylmethyl)-thieno[2,3-d]pyrimidine-2,4(1H,3H)-dione;

1-ethyl-5-[(4S)-4-hydroxy-2-isoxazolidinylcarbonyl]-3-methyl-6-[2-propyl-1H-benzimidazol-1-yl methyl]-thieno[2,3-d]pyrimidine-2,4(1H,3H)-dione;

1-ethyl-5-[(4S)-4-hydroxy-2-isoxazolidinylcarbonyl]-3-methyl-6-[2-oxo-3(2H)-benzothiazolymethyl]-thieno[2,3-d]pyrimidine-2,4(1H,3H)-dione;

1-ethyl-5-[(4S)-4-hydroxy-2-isoxazolidinylcarbonyl]-3-methyl-6-[2-methyl-1H-pyrrolo[2,3-b]pyridin-3-ylmethyl]thieno[2,3-d]pyrimidine-2,4(1H,3H)-dione;

1-ethyl-5-[(4S)-4-hydroxy-2-isoxazolidinylcarbonyl]-3-methyl-6-[5-cyano-1H-indol-1-ylmethyl]-thieno[2,3-d]pyrimidine-2,4(1H,3H)-dione;

5-[(4S)-4-hydroxyisoxazolidin-2-ylcarbonyl]-1-(isobutyl)-6-[1-isopropyl-3,5-dimethyl-1H-pyrazol-4-ylmethyl]-3-methylthieno[2,3-d]pyrimidine-2,4(1H,3H)-dione;

5-[(4S)-4-hydroxyisoxazolidin-2-ylcarbonyl]-1-(isobutyl)-3-methyl-6-[5-methyl-3-phenyl-1H-pyrazol-4-ylmethyl]thieno[2,3-d]pyrimidine-2,4(1H,3H)-dione;

5-[(4S)-4-hydroxyisoxazolidin-2-ylcarbonyl]-1-isobutyl-3-methyl-6-[5-methyl-3-(trifluoromethyl)-1H-pyrazol-4-ylmethyl]thieno[2,3-d]pyrimidine-2,4(1H,3H)-dione;

5-[(4S)-4-hydroxyisoxazolidin-2-ylcarbonyl]-1-isobutyl-6-[3-isopropyl-5-methyl-1H-pyrazol-4-ylmethyl]-3-methylthieno[2,3-d]pyrimidine-2,4(1H,3H)-dione;

6-[3,5-dimethyl-1-phenyl-1H-pyrazol-4-ylmethyl]-5-[(4S)-4-hydroxyisoxazolidin-2-ylcarbonyl]-1-isobutyl-3-methylthieno[2,3-d]pyrimidine-2,4(1H,3H)-dione;

6-[3,5-dimethyl-1-phenyl-1H-pyrazol-4-ylmethyl]-5-[(4S)-4-hydroxyisoxazolidin-2-ylcarbonyl]-3-methyl-1-propylthieno[2,3-d]pyrimidine-2,4(1H,3H)-dione;

6-(1H-1,2,3-benzotriazol-1-ylmethyl)-5-[(4S)-4-hydroxyisoxazolidinylcarbonyl]-3-methyl-1-(isopropyl)-thieno[2,3-d]pyrimidine-2,4(1H,3H)-dione;

5-[(4H)-4-hydroxyisoxazolidinylcarbonyl]-3-methyl-1-(isopropyl)-6-[(2-oxothiazolo[5,4-b]pyridin-1(2H)-yl)methyl]-thieno[2,3-d]pyrimidine-2,4(1H, 3H)-dione;

6-[2,3-dihydro-2-oxo-1H-benzimidazol-1-ylmethyl]-5-[(S)-4-hydroxyisoxazolidinylcarbonyl]-3-methyl-1-(isopropyl)-thieno[2,3-d]pyrimidine-2,4(1H,3H)-dione;

6-[5,6-difluoro-2,3-dihydro-2-oxo-1H-benzimidazol-1-ylmethyl]-5-[(4S)-4-hydroxy-2-isoxazolidinylcarbonyl]-3-methyl-1-(isobutyl)-thieno[2,3-d]pyrimidine-2,4(1H,3H)-dione;

5-[(4S)-4-hydroxyisoxazolidin-2-ylcarbonyl]-6-(imidazo[1,2-a]pyridin-3-ylmethyl)-1-isobutyl-3-methylthieno[2,3-d]pyrimidine-2,4(1H,3H)-dione;

3-methyl-6-[2-methylindol-3-ylmethyl]-1-(isobutyl)-5-(tetrahydroisoxazin-2-ylcarbonyl)-thieno[2,3-d]pyrimidine-2,4(1H,3H)-dione;

6-[2-bromo-4,5-dichloro-1H-imidazol-1-ylmethyl]-5-[(4S)-4-hydroxyisoxazolidinylcarbonyl]-3-methyl-1-(isobutyl)thieno[2,3-d]pyrimidine-2,4(1H,3H)-dione;

5-[(4S)-4-hydroxyisoxazolidin-2-ylcarbonyl]-3-methyl-1-(isobutyl)-6-[2-(methylthio)-1H-imidazo[4,5-b]pyridin-1-ylmethyl]-thieno[2,3-d]pyrimidine-2,4(1H,3H)-dione;

5-[(4S)-4-hydroxyisoxazolidinylcarbonyl]-3-methyl-1-(isobutyl)-6-[2-(methylthio)-3H-imidazo[4,5-b]pyridin-3-ylmethyl]-thieno[2,3-d]pyrimidine-2,4(1H,3H)-dione;

6-[3,5-dimethyl-1H-pyrazol-4-ylmethyl]-3-ethyl-5-[(4S)-4-hydroxy-2-isoxazolidinylcarbonyl]-1-(isopropyl)-thieno[2,3-d]pyrimidine-2,4(1H,3H)-dione;

5-[(4S)-4-hydroxy-2-isoxazolidinylcarbonyl]-3-methyl-1-(isobutyl)-6-[2-(trifluoromethyl)phenylmethyl]-thieno[2,3-d]pyrimidine-2,4(1H,3H)-dione;

5-[(4S)-4-hydroxy-2-isoxazolidinylcarbonyl]-3-methyl-1-(isobutyl)-6-[2-(methylthio)-1H-imidazol-1-ylmethyl]-thieno[2,3-d]pyrimidine-2,4(1H,3H)-dione; or S 5-[4-hydroxylisoxazolidin-2-ylcarbonyl]-3-methyl-1-(isopropyl)-6-[2-methyl-1H-pyrrolo[2,3-b]pyridine-3-ylmethyl]thieno[2,3-d]pyrimidine-2,4(1H,3H)-dione;

or a pharmaceutically acceptable salt thereof.

10. A process for the preparation of a compound of the formula (1) as defined in claim 1, using one of the following processes a) reacting a compound of the formula (10):

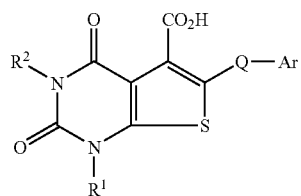

(10)

with isoxazolidine or tetrahydroisoxazine (each being optionally substituted by a hydroxy group);

b) when Q is methylene, reacting a compound of the formula (11):

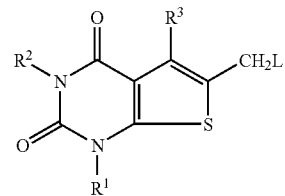

(11)

with a compound of the formula Ar;

c) when Q is methylene, reducing a compound of the formula (12):

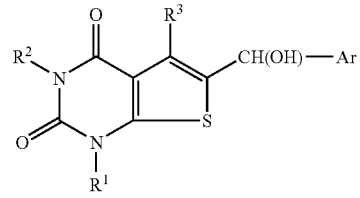

(12)

d) reacting a compound of the formula (11) or (13) to form Ar by primary ring synthesis:

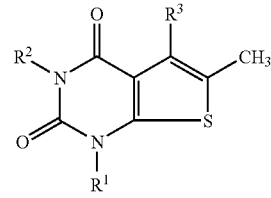

(13)

e) reacting a compound of the formula (14) with $R^1$-$L^2$:

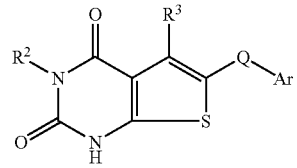

(14)

wherein L and $L^2$ are leaving groups and $R^1$, $R^2$, $R^3$, Q and Ar are defined in claim 1, the process optionally comprises the steps of protecting and deprotecting $R^1$, $R^2$, $R^3$, Q or Ar, and optionally after a), b), c) or d), the process comprises the step of converting the compound of the formula (1) into a further compound of formula (1) and/or forming a pharmaceutically acceptable salt thereof.

11. A pharmaceutical composition comprising a compound according to claim 1 and a pharmaceutically acceptable adjuvant, diluent or carrier.

12. A method of treating asthma in a patient suffering from asthma, which comprises administering to the patient a therapeutically effective amount of a compound according to claim 1.

* * * * *

UNITED STATES PATENT AND TRADEMARK OFFICE
CERTIFICATE OF CORRECTION

PATENT NO. : 7,384,950 B2
APPLICATION NO. : 10/483162
DATED : June 10, 2008
INVENTOR(S) : Rachel Heulwen Reynolds et al.

It is certified that error appears in the above-identified patent and that said Letters Patent is hereby corrected as shown below:

Title Page, Column 1
ABSTRACT (57)
Line 5, delete "isoxyzolidin" insert -- isoxazolidin --

Column 110
Line 35, after "$R^5$" insert -- is --
Line 66 delete "-trifluoromethyl" insert -- trifluoromethyl, --

Column 111
Line 47, delete "[2,3,d]" insert -- [2,3-d] --

Column 112
Line 15, delete "beuzimidazol" insert -- benzimidazol --
Line 29, delete "(S)-5-" insert -- (S) 5- --
Lines 33-34, delete "benzothiazolymethyl" insert -- benzothiazolylmethyl --
Line 36, delete "6-]4" insert -- 6-[4 --

Column 113
Line 12, delete "dichioro" insert -- dichloro --
Line 43, delete "[2,3,b]" insert -- [2,3-b] --
Line 44, delete "[2,3 ,d]" insert -- [2,3-d] --
Line 47, delete "[2,3,b]" insert -- [2,3,-b] --
Line 48, delete "[2,3 ,d]" insert -- [2,3-d] --
Line 50, delete "(S)-5-" insert -- (S) 5- --
Line 64, delete "(S)-5-" insert -- (S) 5- --
Line 65, delete "yl methyl" insert -- ylmethyl --

Column 114
Line 1, delete "(S)-5-" insert -- (S) 5- --
Line 4, delete "(S)-5-" insert -- (S) 5- --
Line 5, delete "pyrrolo]2" insert -- pyrrolo[2 --
Line 10, delete "(S)-6-" insert -- (S) 6- --
Line 11, delete "yl methyl" insert -- ylmethyl --
Line 14, delete "(S)-6-" insert -- (S) 6- --
Line 14, delete "yl methyl" insert -- ylmethyl --
Line 17, delete "(S)-6-" insert -- (S) 6- --
Line 18, delete "yl carbonyl" insert -- "ylcarbonyl" --
Line 26, delete "(S)-6-" insert -- (S) 6- --
Line 37, delete "yl methyl" insert -- ylmethyl --
Line 40, delete "benzothiazolymethyl" insert -- benzothiazolylmethyl --

UNITED STATES PATENT AND TRADEMARK OFFICE
CERTIFICATE OF CORRECTION

PATENT NO. : 7,384,950 B2
APPLICATION NO. : 10/483162
DATED : June 10, 2008
INVENTOR(S) : Rachel Heulwen Reynolds et al.

It is certified that error appears in the above-identified patent and that said Letters Patent is hereby corrected as shown below:

Column 115
Line 6, delete "1H, 3H" insert -- 1H,3H --
Line 43, delete "hydroxylisoxazolidin" insert -- hydroxyisoxazolidin --
Line 44, delete "pyridine" insert -- pyridin --

Signed and Sealed this

Twelfth Day of August, 2008

JON W. DUDAS
*Director of the United States Patent and Trademark Office*